US007572798B2

(12) United States Patent
Jean-Claude et al.

(10) Patent No.: US 7,572,798 B2
(45) Date of Patent: Aug. 11, 2009

(54) COMBI-MOLECULES HAVING SIGNAL TRANSDUCTION INHIBITORY PROPERTIES AND DNA DAMAGING PROPERTIES

(75) Inventors: Bertrand J. Jean-Claude, Dollard-des-Ormeaux (CA); Fabienne Dudouit, Bessens (FR); Stephanie Matheson, Montreal (CA)

(73) Assignee: McGill University, Montreal, Quebec (CA)

( * ) Notice: Subject to any disclaimer, the term of this patent is extended or adjusted under 35 U.S.C. 154(b) by 282 days.

(21) Appl. No.: 10/469,368

(22) PCT Filed: Feb. 26, 2002

(86) PCT No.: PCT/CA02/00253

§ 371 (c)(1),
(2), (4) Date: Dec. 31, 2003

(87) PCT Pub. No.: WO02/068396

PCT Pub. Date: Sep. 6, 2002

(65) Prior Publication Data

US 2004/0086907 A1 May 6, 2004

Related U.S. Application Data

(60) Provisional application No. 60/270,868, filed on Feb. 26, 2001.

(51) Int. Cl.
*A01N 43/90* (2006.01)
*A01N 43/48* (2006.01)

(52) U.S. Cl. .................. 514/259; 514/183; 514/247; 514/279; 514/299; 514/576; 514/577; 514/588; 514/611; 514/740; 514/741; 514/743; 544/283; 544/284; 544/293

(58) Field of Classification Search ............. 514/183, 514/228.2, 231.5, 245, 259, 266.21, 266.22, 514/266.4, 266.6, 247, 279, 576, 577, 588, 514/611, 740, 741, 743; 544/283, 284, 293
See application file for complete search history.

(56) References Cited

OTHER PUBLICATIONS

Reilly, R.M. et al. J. Nucl. Med. 41(3): 429-438, 2000.*
Matheson, S. and B. J. Jean-Claude, Proceedings of the American Association for Cancer Research, 41: 423-424, Mar. 2000.*
Brahimi, F. et al., Journal of Pharmacology and Experimental Therapeutics, 303(1): 238-246, 2002.*
Sinha et al., 1995; Sherwood et al., 1999; Kondapaka and Reddy, 1996; Alaoui-Jamali et al., 1997; Tsai et al., 1993.
Carroll et al., 1997; Deininger et al., 1997; Levitzki and Gazit, 1999. Xie et al., 1999; Turner et al., 1996; Modjtahedi and Dean, 1998; Moyer et al., 1997.
Levitzki and Gazit, 1999; Rewcastle et al., 1997; Lanzi et al., 1997; Moyer et al., 1997; Rewcastle et al., 1995; Rewcastle et al., 1988.

Smaill et al., 1999.
Moyer, J.D., Barbacci, E.G., Iwata, K., Arnold, L., Boman, B., Cunningham, A., DiOrio, C., Doty, J., Morin, M.J., Moyer, M.J., Neveu, M., Pollak, V.A. Pustilnik, L.R., Reynolds, M.M., Sloan, D., Teleman, A., and Miller, P. Induction of apoptosis and cell cycle arrest by CP-358, 774, an inhibitor of epidermal growth factor receptor tyrosine kinase. Cancer Res. 57: 4838-4848, 1997.
Rewcastle, G.W., Denny, W.A. Bridges, A.J., Hairong, Z., Cody, D.R., McMichael, A., and Fry, D.W. Tyrosine kinase inhibitor. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J. Med. Chem. 38: 3482-3487, 1995.
Rewcastle, G.W., Murray, D.K., Elliott, W.L., Fry, D.W., Howard, C.T., Nelson, J.M., Roberts, B.J., Vincent, P.W., Showalter, H.D., Winters, R.T., and Denny, W.A. Tyrosine kinase inhibitors. 14. Structure-activity relationships for methylamino-substituted derivatives of 4-[(3-bromophenyl)amino]-6-(methylamino)-pyrido[3,4-d]pyridine (PD 158780), a potent and specific inhibitor of the tyrosine kinase activity of receptors for the EGF family of growth factors. J. Med. Chem. 41: 742-751, 1998.
Caliaro, M.J., Vitaux, P., Lafon, C., Lochon, I., Nehme, A., Valette, A., Canal, P., Bugat, R., and Jozan, S. Multifactorial mechanism for the potentiation of cisplatin (CDDP) cytotoxicity by all-trans retinoic acid (ATRA) in human ovarian carcinoma cell lines. Br. J. Cancer, 75: 333-340, 1997.
Modjtahedi, H. and Dean, C. The receptor for EGF and its ligands: expression, prognostic value and target for tumour therapy. Int. J. Oncol. 4: 277-296, 1998.
Fry, D.W. (1999): Inhibition of the epidermal growth factor receptor family of tyrosine kinases as an approach to cancer chemotherapy: progression from reversible to irreversible inhibitors. Pharmacol Ther 82: 207-218.; Smalll et all., 2000.
Ciardiello, F.; Caputo, R.; Bianco, R.; Damiano, V.; Pomatico, G.; De Placido, S.; Bianco, A.R.; Tortora, G. (2000): Antitumor effect and potentiation of cytotoxic drugs activity in human cancer cells by ZD-1839 (Iressa), an epidermal growth factor receptor-sensitive tyrosine kinase inhibitor. Clin Cancer Res 6: 2053-2063.
Rewcastle et al., 1997; Rewcastle et al., 1995.
Rewcastle et al., 1997; Rewcastle et al., 1998; Rewcastle et al., 1995.

(Continued)

*Primary Examiner*—Alana M. Harris
*Assistant Examiner*—Anne L Holleran
(74) *Attorney, Agent, or Firm*—Fulbright & Jaworski L.L.P.

(57) ABSTRACT

The present invention relates to a series of new chemical agents that demonstrate anti-tumor activity. More particularly, the present invention relates to molecules, referred to as "combi-molecules", that combine two major mechanisms of anti-tumor action. A combi-molecule is capable of degrading to a ligand involved in cell signaling pathways and to an agent capable of damaging DNA. More specifically, the present invention relates to molecules capable of blocking epidermal growth factor receptor (EGFR) mediated signal transduction and capable of damaging DNA. The present invention also relates to a general method of synthesis of these combi-molecules.

30 Claims, 25 Drawing Sheets

OTHER PUBLICATIONS

Rewcastle, G.W., Bridges, A., Fry, D.W., Rubin, R.R., and Denny, W.A. Tyrosine kinase inhibitors. 12. Synthesis and structure-activity relationships for 6-substituted 4-(phenylamino)pyrimidino[5,4d]pyrimidines designed as inhibitors of the epidermal growth factor receptor. J. Med. Chem. 40: 1820-1826, 1997.

Rewcastle et al., 1995.

Walker, M.D. Nitrosoureas in central nervous system tumors. Cancer Chemother. Rep. 4: 21-26, 1973.

Walker M.D. and Hurwitz, B.S. BCNU (1,3-bis(2-nitrosourea; NSC-409962) in the treatment of malignant brain tumor—a preliminary report. Cancer Chemother. Rep. 54:273-281, 1970.

Wilson, C.B., Boldrey, E.B., and Enot, K.J. 1,3-bis (2-chloroethyl)-1-nitrosourea (NSC-409962) in the treatment of brain tumors. Cancer Chemother. Rep. 54: 273-281, 1970.

Yarosh, D.B., Hurst-Calderone, S., Babich, M.A., and Day, R.S. Inactivation of O6-methylguanine-DNA methyltransferase and sensitization of human tumor cells to killing by chloroethylnitrosourea by O6-methylguanine as a free base. Cancer Res. 46: 1663-1668, 1986.

Gibson, N.W., Hartley, J.A., LaFrance, R.J., and Vaughan, K. Differential cytotoxicity and DNA-damage effects produced in human cells of the Mer+ and Mer- phenotypes by a series of 1-aryl-3-alkyltriazenes. Cancer Res. 46: 4999-5003, 1986.

Pegg et al., 1995; Tisdale, 1987; Bodell et al., 1985; Baer et al., 1993. Ching et al., 1993b; Moyer et al., 1997b.

Tisdale, 1987; Mitchel and Dolan, 1993; Lee et al., 1991; Chen et al., 1993.

Matheson, S.L.M.; McNamee, J.P.; Jean-Claude, B.J. (2001): Design of a chimeric 3-methyl-1,2,3-triazene with mixed receptor tyrosine kinase and DNA damaging properties: a novel tumour targeting strategy. J Pharm Exp Ther 296: 832-840.

Baig, G.U., Stevens, M.F.G. (1987): Antitumor imidazotetrazines. Part 12. Reactions of mitozolomide and its 3-alkyl congeners with oxygen, nitrogen, halogen, and carbon nucleophiles. J Chem Soc Perkin Trans 1, 1665-667. Cameron, L.M.; LaFrance, R.J.; Hemens, C.M.; Vaughan, K.; Rajaraman, R.; Chubb, D.C.; Goddard, P.M. ;(1985): Triazene metabolism. IV. Derivatives of hydroxymethyltriazenes: potential prodrugs for the active metabolites of the anti-tumour triazene, DTIC. Anti-Cancer Drug Des 1: 27-36.

Stevens, M.F.G.; Hickman, J.A.; Stone, R.; Gibson, N.W.; Baig, G.U.; Lunt, E., Newton, C.G.; (1984): Antitumor imidazotetrazines. 1. Synthesis and chemistry of 8-carbamoyl-3-(2-chloroethyl)midazo[5,1,-d]-1,2,3,5-tetrazin-4(3H)-one, a novel broad-spectrum antitumor agent. *J Med. Chem* 27: 196-201. Stevens, M.F.G.; Hickman, J.A.; Langdon, S.P.; Chubb, D.; Vickers, L.; Stone, R.; Baig, G.; Goddard, C.; Gibson, N.W.; Slack, J.A.; (1987): Antitumor activity and pharmacokinetics in mice of 8-carbamoyl-3-methyl-imidazo[5,1-d]-1,2,3,5-tetrazin-4(3H)-one (CCRG 81045; M&B 39831), a novel drug with potential as an alternative to dacarbazine. Cancer Res 47: 5846-5852.

Tsai, C.M., Levitzki, A., Wu, L.H., Chang, K.T., Cheng, C., Gazit, A., and Perng, R.P. Enhancement of chemosensitivity by tyrphostin AG825 in High-p185 expressing non-small cell lung cancer cells. Cancer Res. 56: 1068-1074, 1996.

Moyer, J.D.; Barbacci, E.G.; Iwata, K.K.; Arnold, L.; Boman, B.; Cunningham, A.; DiOrio, C.; Doty, J.; Morin, M.J.; Moyer, M.P.; (1997): Induction of apoptosis and cell cycle arrest by CP-358,774, an inhibitor of epidermal growth factor receptor tyrosine kinase. Cancer Res 57: 4838-4848.; Vincent, P.W.; Bridges, A.J.; Dykes, D.J.; Fry, D.W.; Leopold, W.R.; Patmore, S.J.; Roberts, B.J.; Rose, S.; Sherwood, V.; Zhou, H. (2000): Anticancer efficacy of the irreversible EGFr tyrosine kinase inhibitor PD 0169414 against human tumor xenografts. Cancer Chem Pharmacol 45: 231-238.

Singh et al., 1994.

McNamee, J.P.; Mclean, J.R.; Ferrarotto, C.L.; Bellier, P.V. (2000): Comet assay: rapid processing of multiple samples. Mutation Res 466: 63-69.

Skehan, P.; Storeng, R.; Scudiero, D.; Monks, A.; McMahon, J.; Vistica, D.; Warren, J.T.; Bokesch, H.; Kenney, S.; Boyd, M.R. (1990): New colorimetric cytotoxicity assay for anti-cancer drug screening. *J* Natl Cancer Inst 82: 1107-1112.

Cameron et al., 1985; Manning, H.W.; Cameron, L.M.; LaFrance, R.J.; Vaughan, K.; Rajaman, R. (1985): Triazene metabolism. V. Chemical and biological properties of N,N-bis-[1-aryl-3-methyltriazen-3-yl)-methyl]-methylamines: potential prodrugs for the cytotoxic monomethyltriazenes. *Anti-cancer Drug Des* 1: 37-43.;

Rewcastle, G.W.; Denny, W.A.; Bridges, A.J.; Zhou, H.; Cody, D.R.; McMichael, A.; Fry, D.W. (1995): Tyrosine kinase inhibitors. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J Med Chem 38: 3482-3487.

Lanzi, C.; Pensa, T.; Cassinis, M.; Corti, C.; Gambetta, A.R.; Pratesi, G.; Menta, E.; Ardini, E.; Zunino, F. (1997): A cell and mechanicm-based approach for the selection of EGF receptor inhibitors. Anti-cancer Drug Des. 12: 515-524.

Fornace et al., 1990.

Jean-Claude et al., 1999.

Chou et al., 1984.

Tari, A.M.; Lopez-Berestein, G.; (2000): Serum predominantly activates MAPK and kinases in EGFR- and ErbB2-overexpressing cells, respectively. Intl J Cancer 86: 295-297.

Smaill, J.B.; Rewcastle, G.W.; Loo, J.A.; Greis, K.D.; Chan, O.H.; Reyner, E.L.; Lipka, L; Showalter, H.D.; Vincent, P.W.; Elliott, W.L.; (2000): Tyrosine kinase inhibitors 17. Irreversible inhibitors of the epidermal growth factor receptor: 4-(phenylamino)quinazoline and 4-(phenylamino)pyrido[3-2-d]pyrimidine-6-acrylaminde bearing additional solubilizing functions. J Med Chem 43: 1380-1397.

Fry, D.W.; Bridges, A.J.; Denny, W.A.; Doherty, A.; Greis, K.D.; Hicks, J.L.; Hook, K.E.; Keller, P.R.; Leopold, W.R.; Loo, J.A.; (1998): Specific irreversible inactivation of the epidermal growth factor receptor and erbB2, by a new class of tyrosine kinase inhibitor. Proc Natl Acad Science 95: 12022-12027.

Vistica, D.T.; Skehan, P.; Scudiero, D.; Monks, A.; Pittman, A.; Boyd, M.R. (1991): Tetrazolium-based assays for cellular viability: a critical examination of parameters affecting formazan production. Cancer Res 51: 2515-2520.

Mitchel, R.B.; Dolan, M.E. (1993): Effect of temozolomide and dacarbazine on O6-alkylguanine-DNA alkyltransferase activity and sensitivity of human tumor cells and xenografts.to 1,3-bis(2-chloroethyl)-1-nitorsourea. Cancer Chemother. Pharmacol. 32:59-63.

Lanzi et al., 1997; Modjtahedi and Dean, 1998; Yaish et al., 1988; Modjtahedi and Dean, 1998.

Yaish et al., 1988.

Hill et al., 1989; Carter et al., 1976; Lee et al., 1992; Carter et al., 1994.

Kolar et al., 1980; Foedstad et al., 1985; Cameron et al., 1985; Manning et al., 1985.

Catapano et al., 1987.

Hartley et al., 1986; Pera et al., 1981.

Hammet, 1940; Andrejus, 1988; Jean-Claude and Williams, 1988.

Jeff et al., 2000.

Palmer, B.D.; Trumpp-Kallmeyer, S.; Fry, D.W.; Nelson, J.M.; Showalter, H.; Denny, W.A. (1997): Tyrosine kinase inhibitors. 11. Soluble analogues of pyrrolo- and pyrazoloquinazolines as epidermal growth factor receptor inhibitors: synthesis, biological evaluation and modeling of the mode of binding. J Med Chem 40: 1519-1529.

Denny, B.J.; Wheelhouse, R.T.; Stevens, M.F.; Tsang, L.L.; Slack, J.A. (1994): NMR and molecular modeling investigation of the mechanism of activation of the antitumor drug temozolomide and its interaction with DNA. Biochemistry 33: 9045-9051.

Davis, R.J. (1993): The mitogen-activated protein kinase signal transduction pathway. J Biol Chem 268: 14553-14556.

* cited by examiner

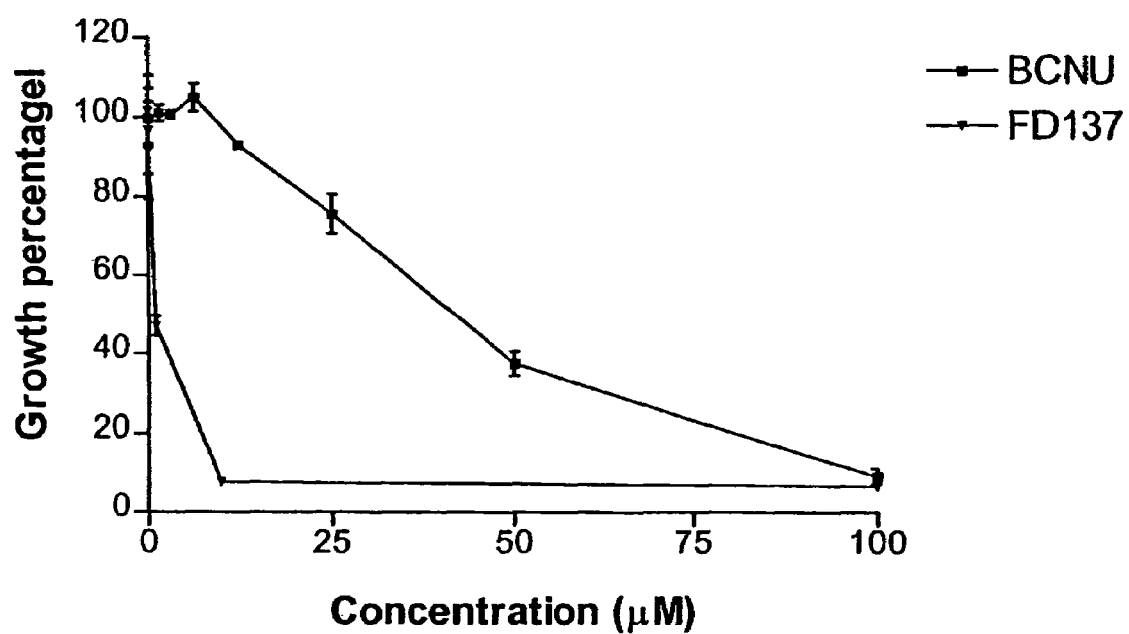
FIG_4

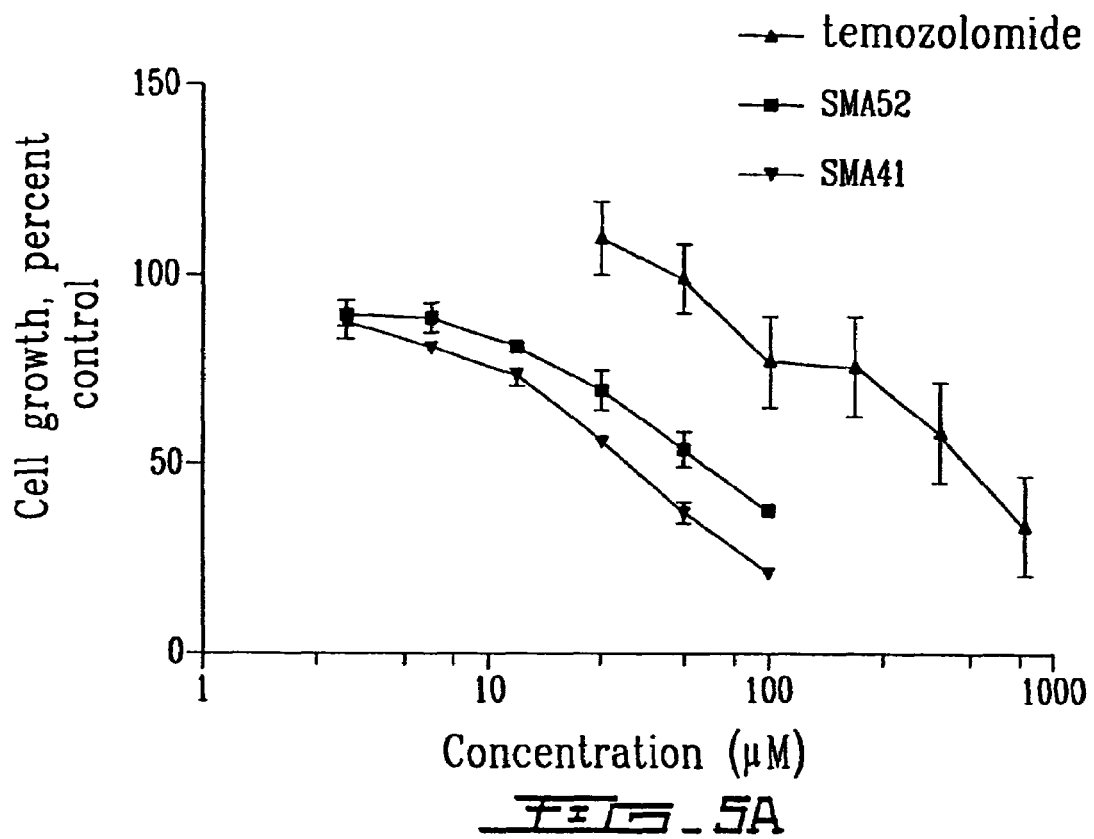
FIG_5A
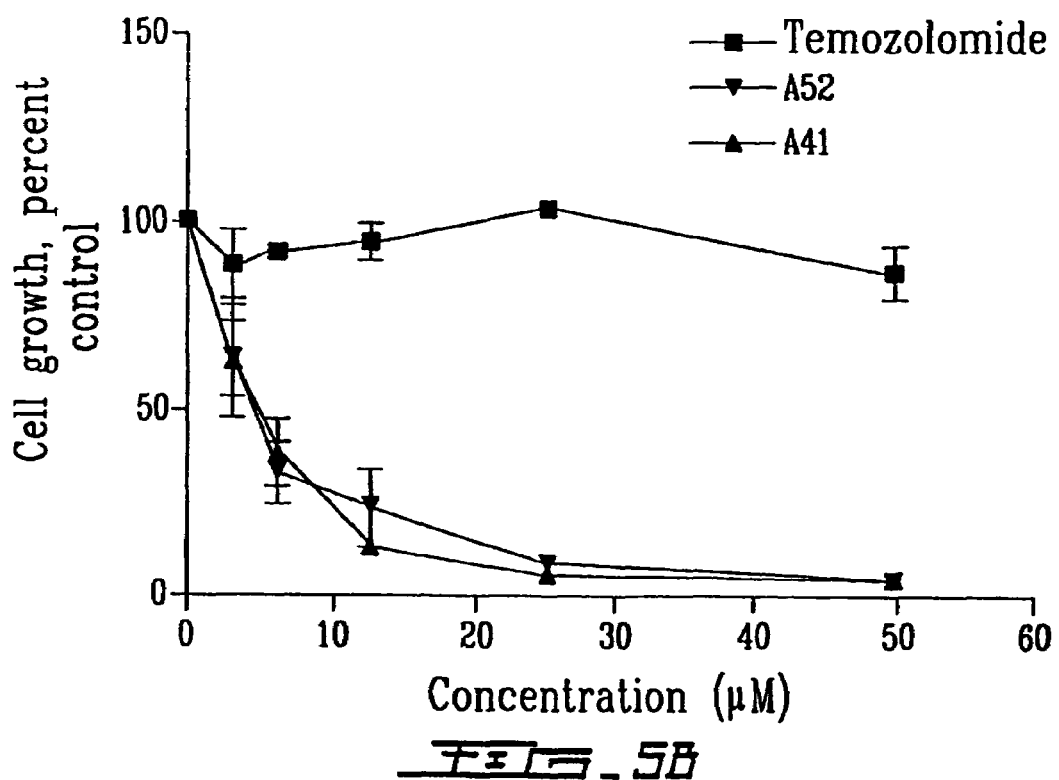
FIG_5B

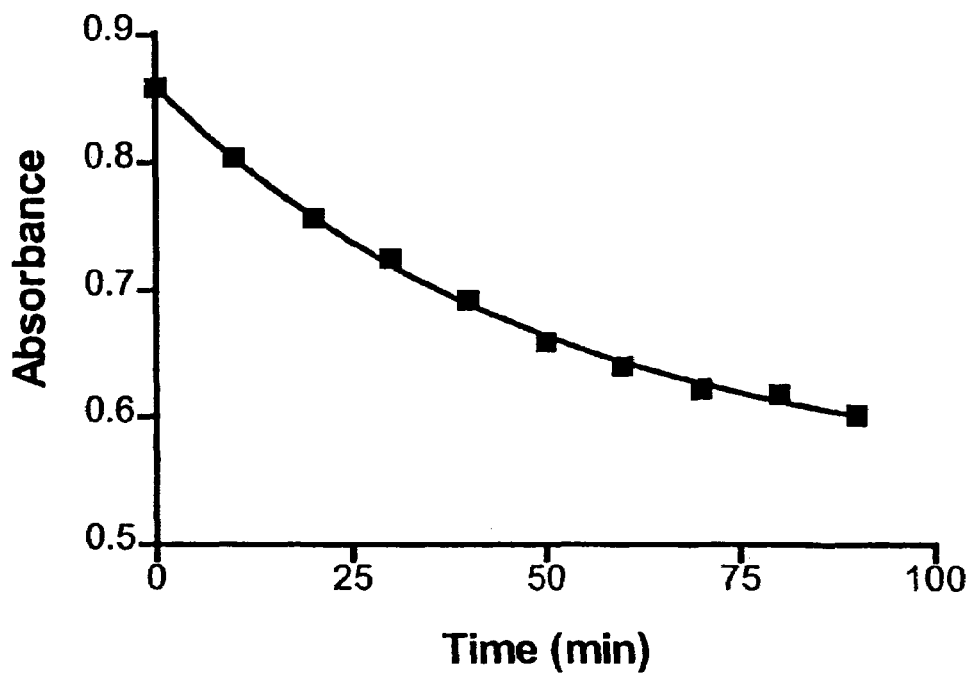
FIG_12A
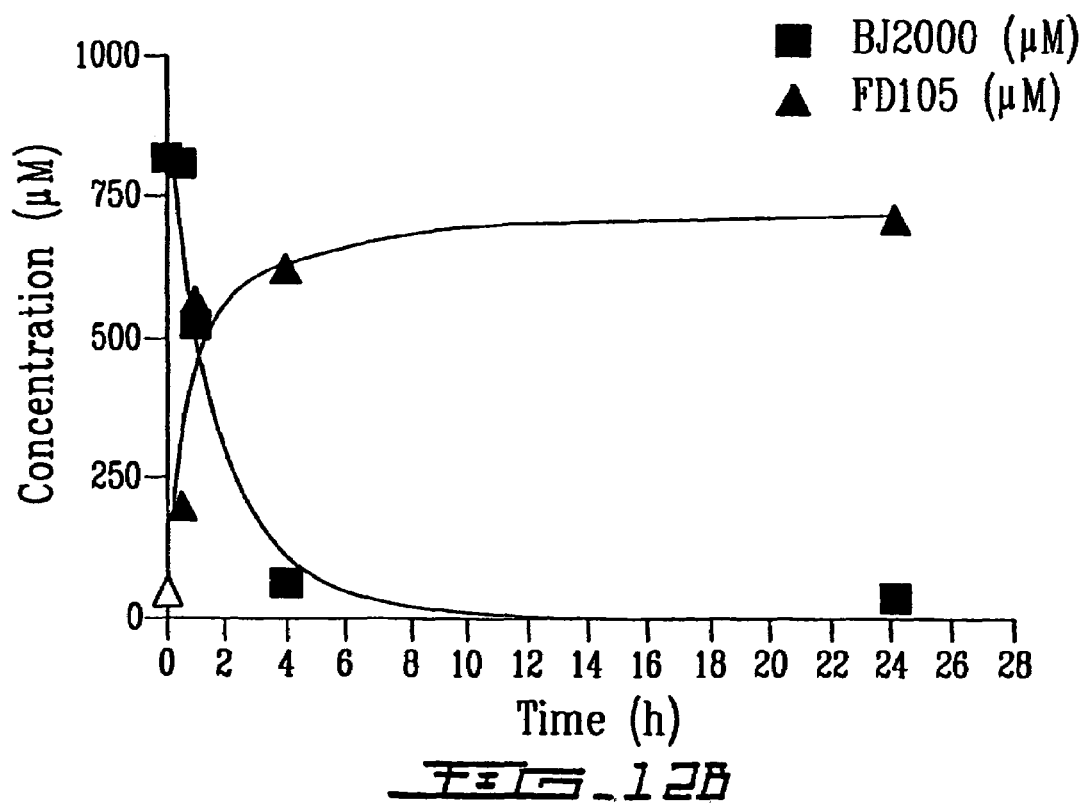
FIG_12B

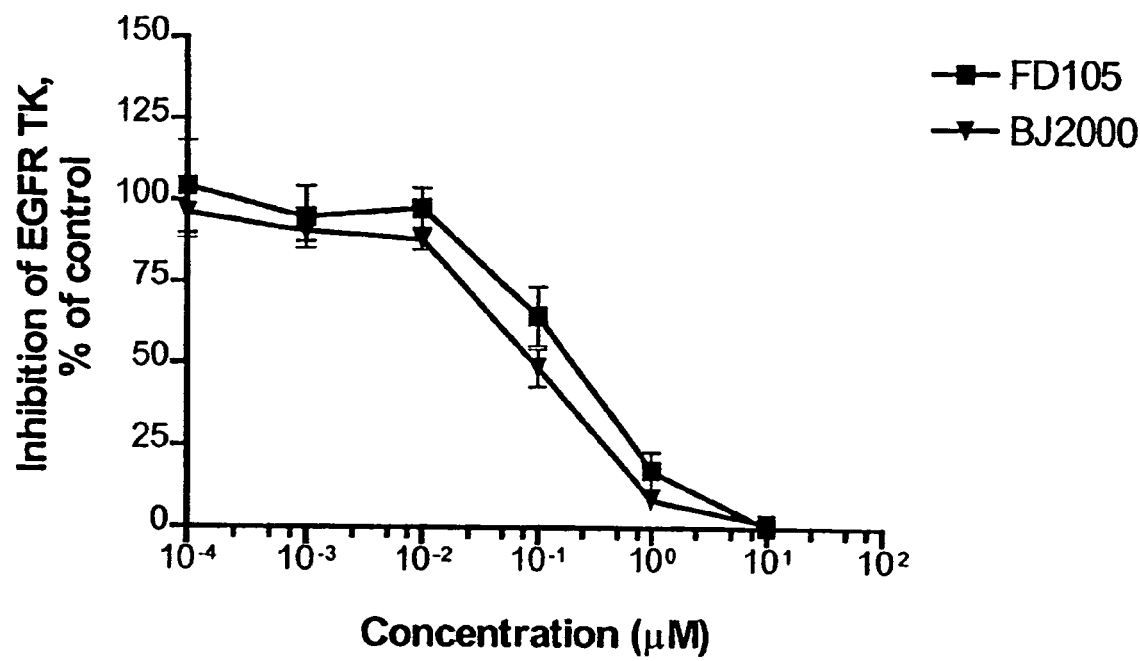
FIG_13A
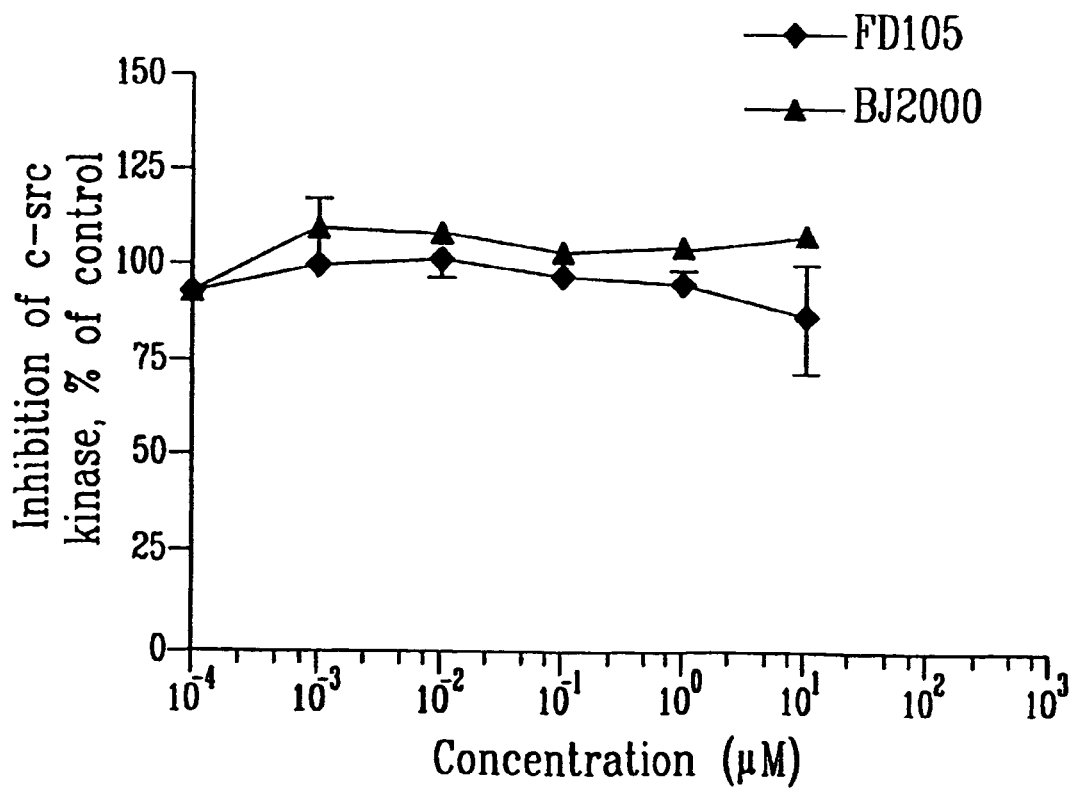
FIG_13B

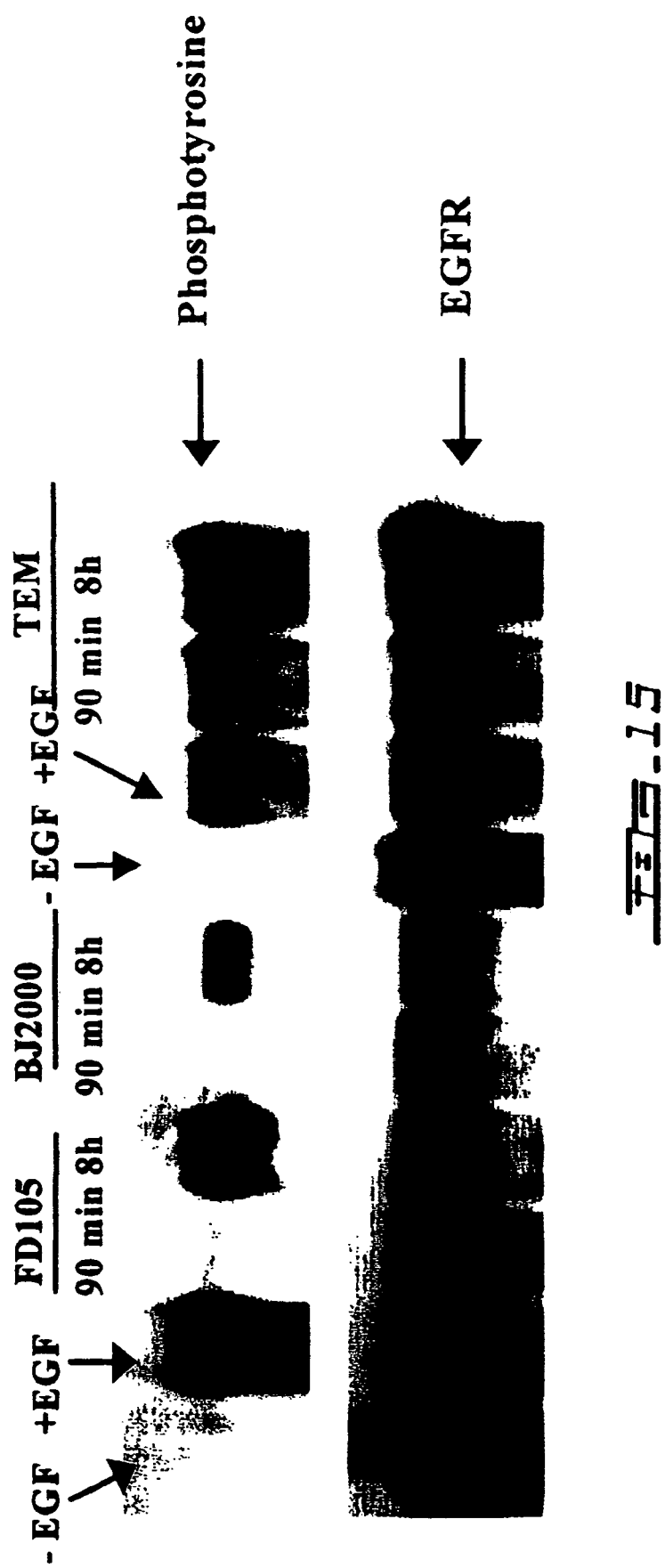

COMBI-MOLECULES HAVING SIGNAL TRANSDUCTION INHIBITORY PROPERTIES AND DNA DAMAGING PROPERTIES

This application is a U.S. National Phase Application under 35 U.S.C. § 371 of International Application No. PCT/CA02/00253 filed 26 Feb. 2002, which claims priority to U.S. Provisional Application No. 60/270,868 filed 26 Feb. 2001.

FIELD OF THE INVENTION

The present invention relates to a series of new chemical agents that demonstrate anti-tumor activity. More particularly, the present invention relates to molecules, referred to as "combi-molecules", that combine two major mechanisms of anti-tumor action. More specifically, the present invention relates to molecules capable of blocking epidermal growth factor receptor (EGFR) mediated signal transduction and capable of damaging DNA. The present invention also relates to a general method of synthesis of these combi-molecules.

BACKGROUND OF THE INVENTION

Cancer is a disease state characterized by the uncontrolled proliferation of genetically altered tissue cells. There have been several chemotherapeutic approaches developed to target cancer. These include alkylating and anti-mitotic agents, anti-metabolites and anti-tumor antibiotics. Such therapeutic agents act preferentially on rapidly proliferating cells such as cancer cells.

Acquired resistance mediated by DNA repair enzymes has often imposed severe limitations on the use of DNA-interactive agents and, in many cases, useful clinical anti-tumor activity could not be observed with the administration of multiple anti-tumor drugs having different mechanisms of action.

In the last 10 years there has been a considerable increase in our understanding of the molecular basis of cellular resistance via DNA repair processes, as well as of the spontaneous repair of naturally occurring errors in DNA polymerization. However, to date this has not translated into an increase in the efficacy of DNA-reactive drugs targeting cancers, including breast, lung and ovarian carcinomas.

The selection of many DNA reactive drugs for further in vivo testing was primarily based upon their high reactivity with DNA bases, their DNA binding affinity and on the significant cytotoxicity that they induce in tumor cells. Structure-activity relationship studies were often directed at cell growth and/or in vivo activity in murine models.

The over-expression and dysfunction of tyrosine kinases (TKs), directly or indirectly implicated in mitogenic signaling in tumor cells, have been extensively studied and are now considered the major functional differences between normal and tumor cells (1). Because of their significant involvement in tumor progression, over-expressed receptor TKs have now become the targets for drug design and selective chemotherapeutic interventions (2). One such target is the epidermal growth factor receptor (EGFR) which, in many patients, is associated with aggressive tumor progression and invasion (3). It has already been demonstrated that blocking signal transduction through the mediation of the TK activity of the EGFR translates into significant anti-tumor activity both in vitro and in vivo, and two novel agents are now in Phase II clinical trials (4). Despite being significantly less toxic than previous cytotoxic agents, most TK inhibitors currently in clinical trials have the disadvantage of being cytostatic agents that induce reversible inhibitory growth activity (5).

Many human tumors, including lung, breast and brain tumors, express high levels of the EGFR (6). It has already been shown that blockade of the EGFR pathway by several methods inhibits the proliferation of a variety of tumor cell lines both in vitro and in vivo (7-10). Although EGFR antibodies have recently been shown to trigger apoptosis in tumor cells (11), the anti-proliferative activity of EGFR tyrosine kinase inhibitors is often cytostatic and not cytotoxic.

The anti-tumor efficacy of EGFR TK inhibitors has already been demonstrated in vivo. However, one major limitation of current EGFR tyrosine kinase inhibitors is the high intracellular concentration of ATP which represents a major barrier to sustained inhibition of EGF-stimulated signal transduction in tumor cells. Where they cannot induce apoptosis, EGFR TK inhibitors are cytostatic agents that induce reversible antitumor effects. Considerable attention is now being turned towards the synthesis of irreversible inhibitors. Recently, irreversible inhibitors of the EGFR family have been synthesized showing greater potency than their reversible predecessors (12, 40, 41). The irreversible inhibition of TKs may nonetheless be insufficient to induce cell death. Unfortunately, irreversible inhibition of EGFR may not suffice to induce sustained antitumor activity if the cells possess alternative growth mechanisms. The combination with cytotoxic drugs, to potentiate the action EGFR TK inhibition, is now being considered a useful alternative (13).

Anilinoquinazolines are a novel class of highly specific receptor compounds that were shown to inhibit EGFR-related signal transduction by competitive binding in the ATP site of the EGFR (14). Blockade of EGFR-mediated signal transduction by anilinoquinazolines of types A and B has already been shown to translate into significant antitumor activity (7,8). The significant number of structure-activity-relationship (SAR) studies on 4-anilinoquinazolines and pyrido[d]pyrimidines as EGFR TK inhibitors is consistent with the compounds binding to the ATP site of the EGFR (7-10, 15).

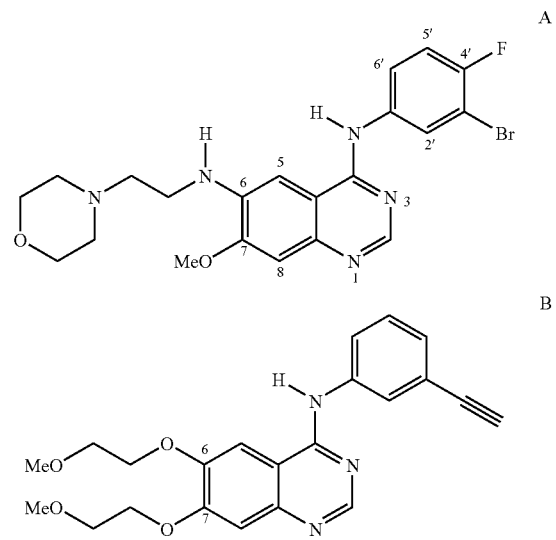

Molecular modeling suggests that the N-1 atom accepts a H-bond from Met-769, whereas the N-3 atom accepts a H-bond from the side chain of Thr-766 located on strand 5 deep in the binding cleft (8,9,16). The anilino moiety binds in an adjacent hydrophobic pocket. Molecular modeling further suggests that the only positions on the inhibitors where substituents could be altered without affecting their binding affinity are the 6- and 7-positions located at the entrance of the binding cleft (17). A variety of compounds with bulky side chains on the 6- and 7-positions have been synthesized and were found to retain significant binding affinity for the EGFR ATP binding site. The tolerance of bulky substituents in the SAR of anilinoquinazolines was illustrated by the significant activities of structures A and B, which are now in Phase II clinical trials.

Nitrosoureas remain among the oldest drugs used in the clinical management of leukemias and many solid tumors (18-20). The lead compound of this class, bis-chloroethyl-N-nitrosourea (BCNU) has been one of the most potent agents used in the treatment of brain tumors (19,20) for over 30 years. Its mechanism of action is based on the induction of cytotoxic DNA single-strand breaks and DNA cross-links that ultimately lead to cancer cell death (21,22).

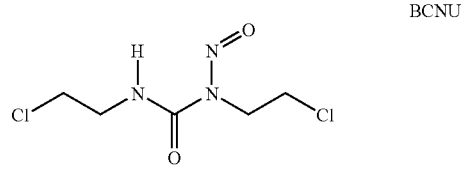

BCNU

Alkyldiazonium compounds and precursors such as dacarbazine and TEM (Scheme 1) are cytotoxic agents whose mechanism of action is primarily based on the alkylation of DNA at the 6- or 7-position of guanine (23). TEM is now approved for the treatment of melanoma and brain tumors.

There exist many biochemical differences between normal cells and tumor cells. Our knowledge of these differences has significantly increased. One such difference is the over-expression and mutation of several signal transduction proteins. The dysfunction of the EGFR and related receptors occurs in many tumors, including lung, breast and ovarian cancers. Compounds with multiple intracellular targets would be expected to be more effective against resistant tumors. More specifically, the development of chemical agents that demonstrate the potential to simultaneously target one such protein, here the EGFR, as well as genomic DNA would be greatly desired. Compounds with multiple intracellular targets would fight cancer more aggressively and would consequently be more effective. This mixed targeting strategy is termed the "Combi-Targeting Concept" and its development provides an alternative to classical therapies involving the non-selective cisplatin and many other alkylating agents. In other words, combining such non-selective DNA damaging agents with an oncogenic tyrosine kinase targeting molecule would result in new molecules being more selective and effective towards tumors expressing these oncogenes.

There thus remains a need for cytotoxic agents that can synergize with ligands that inhibit cell proliferation or oncogenesis. More specifically, there remains a need for chemical agents that are capable of simultaneously targeting a specific molecule, such as the epidermal growth factor receptor (EGFR), and genomic DNA.

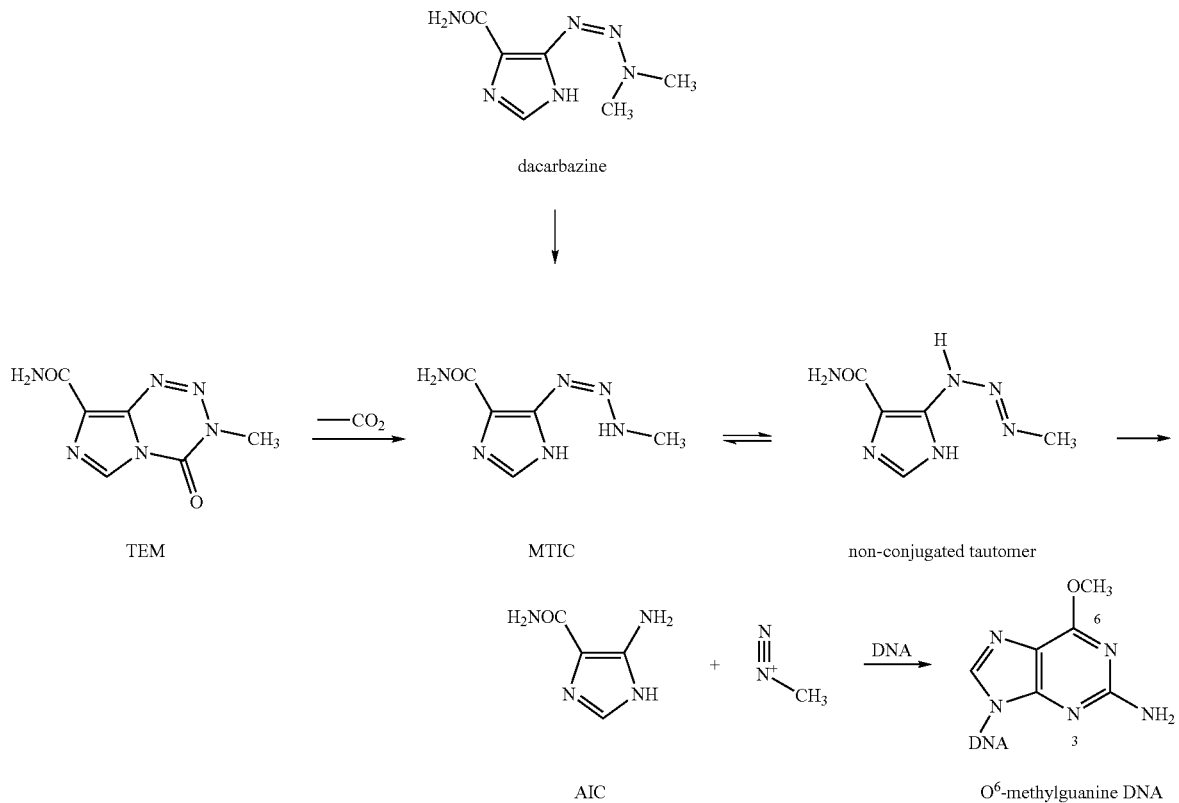

The present invention seeks to meet these and other needs.

SUMMARY OF THE INVENTION

The present invention relates to a series of new molecules that embody both a cytotoxic moiety and a cytostatic moiety.

The present invention relates to a series of molecules useful in the treatment of refractory solid tumors such as breast, lung, epithelial ovarian, vulva, prostatic or head and neck carcinomas.

The present invention relates to a series of new molecules referred to as "combi-molecules" having a high affinity for proteins involved in cell proliferation signaling pathways and that are also capable of damaging DNA.

The present invention relates to a series of new molecules that combine two major mechanisms of anti-tumor action, namely, blocking of signal transduction mediated by the EGFR (inhibiting the EGFR TK) and inducing DNA damage.

As well, the present invention relates to the synthesis of novel compounds designed to simultaneously target the EGFR TK and genomic DNA, thus demonstrating the potential to treat a variety of disease states more efficiently than a separate administration of each targeting compound.

The "combi-targeting" concept postulates that; a molecule termed "combi-molecule" (C-molecule) having binary epidermal growth factor receptor (EGFR) targeting properties and DNA damaging properties, and additionally having the ability to be hydrolyzed into another EGFR inhibitor, should induce sustained anti-proliferative activity in cells overexpressing EGFR.

Unless defined otherwise, the scientific and technological terms and nomenclature used herein have the same meaning as commonly understood by a person of ordinary skill.

As used herein, the terminology "cytotoxic moiety" refers to a molecule inducing cell death.

As used herein, the terminology "cytostatic moiety" refers to a molecule blocking cell growth without causing cell death.

As used herein, the terminology "combi-molecule" refers to a biologically active molecule having mixed or multiple targets. It is capable of multiple targeting by degrading into substances that are also bio-active.

The combi-targeting strategy seeks to combine the signal transduction inhibitory mechanisms of receptor TK inhibitors with the cytotoxic effects of DNA damaging fragments in one single agent termed combimolecule. This combi-molecule is designed to: (a) inhibit the receptor TK on its own and (b) be converted, upon hydrolysis, into another inhibitor of the same receptor TK and a DNA damaging species. This principle simply leads to a receptor-affine TZ-I capable of generating another inhibitor I+a cytotoxic molecule (TZ) (Scheme 2).

Scheme 2

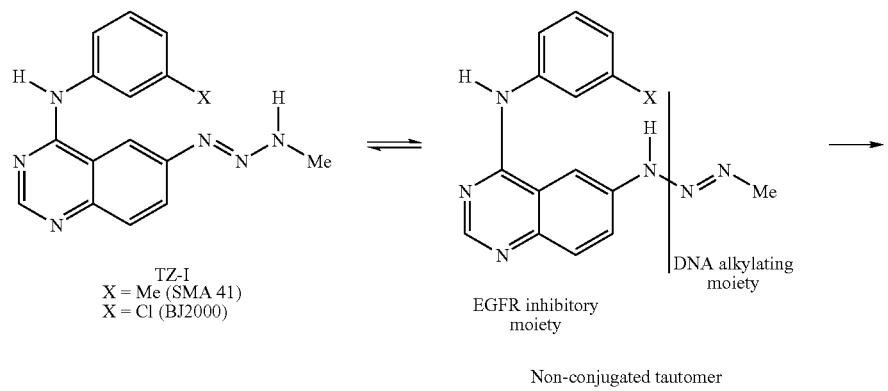

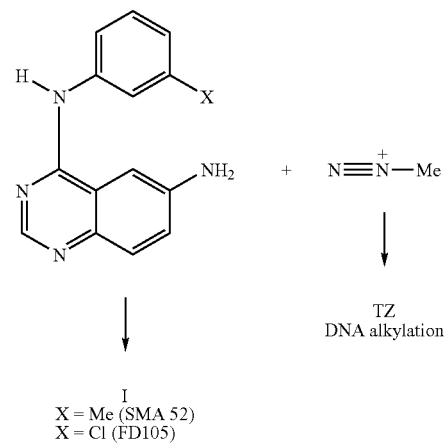

A compound such as SMA41 exhibits two distinct structural characteristics: (a) a 1,2,3-triazene linkage, the pharmacophore of the active metabolites of dacarbazine or TEM (a DNA damaging agent) and (b) a 4-anilinoquinazoline moiety, the pharmacophore of the potent quinazoline class of EGFR TK inhibitors now in clinical trial (24).

As previously shown in Scheme 1, 3-alkyl-1,2,3-triazenes such as TEM (shown to have clinical activity in the treatment of solid tumors such as gliomas and malignant melanoma and shown to be significantly inactive in Mer⁺ cells), or its metabolite MTIC, are known to heterolyze to an aromatic amine (see AIC, Scheme 1) and an alkyldiazonium species (e.g. methyldiazonium) under hydrolytic conditions. Substantial evidence suggests that alkylation of DNA at the O-6 position of guanine corresponds to the cytotoxic lesion induced by 3-methyl or 3-(2-chloroethyl)-1,2,3-triazenes (23).

Mer⁺ cells expressing elevated levels of MGMT, an enzyme capable of repairing the $O^6$-alkylguanine lesion, show significant resistance to the action of alkylating agents such as TEM or its metabolite MTIC (25).

The current invention describes molecules generated by appending the alkyltriazene moiety to the 6-position of the quinazoline heterocycle. Based upon the mechanism of hydrolytic cleavage of 1,2,3-triazenes and upon the SAR of quinazolines, SMA41 was synthesized to release (a) a known competitive inhibitor of the ATP binding site of EGFR, henceforth referred to as SMA52, and (b) the DNA damaging methyldiazonium species (Scheme 2).

Preliminary evidence on the feasibility of a mixed EGFR/DNA directed molecule containing a 3-methyl-1,2,3-triazene moiety appended to the 6-position of a 4-anilinoquinazoline moiety was recently reported (26). The compound (SMA41) was shown to possess mixed EGFR/DNA targeting properties on its own ($IC_{50}$ competitive binding=0.2 μM), and was illustrated to degrade to another inhibitor (SMA52) ($IC_{50}$ competitive binding=1.0 μM). The choice of 3-alkyl-1,2,3-triazenes as a DNA alkylating moiety was largely inspired by its small size, and its ability to heterolyze to an aromatic amine and an alkyldiazonium species able to kill cells by alkylating DNA at the 6-position of guanine (27). In comparison to temozolomide (TEM), a cyclic prodrug of the monoalkyltriazene 5-(3-methyltriazen-1-yl)imidazole-4-carboxamide (MTIC) (28), the potency of SMA41 was demonstrated to be superior to that of a classical combination of SMA52 and TEM at equitoxic doses. While SMA41 possessed significant EGFR TK inhibitory activity, the stable molecule that it released (SMA52) possesses weak EGFR TK inhibitory activity ($IC_{50}$=1.0 μM).

Since the degradation of TZ-I leads to a stable inhibitor I that will remain longer in the cell medium, it is assumed that the potency of the latter may play a critical role in the overall antiproliferative activity. In an attempt to generate a TZ-I capable of generating an I having a stronger affinity than SMA52, the anilino methyl group was substituted for a less bulky chloro substituent, producing a TZ-I termed BJ2000 (Scheme 2). This combi-molecule (BJ2000) was observed as possessing a 2-fold stronger affinity than SMA41 and is capable of producing an I possessing a 5-fold stronger affinity than SMA52.

The combi-molecule BJ2000 was demonstrated to be capable of releasing an I termed FD05 (yield: 87%) in a cell culture medium supplemented with serum. This model exhibited: 1) mixed DNA damaging and EGFR phosphotyrosine inhibitory activity, 2) preferential inhibition of EGF-induced growth over PDGF and serum, and 3) significantly more potent DNA damage and cytotoxicity in an EGFR-transfectant as compared to its parental line. More importantly, it was demonstrated that BJ2000 irreversibly induced the inhibition of autophosphorylation, confirming path 4 of Scheme 2, and partially irreversibly inhibited cell growth 5 days after treatment.

The "combi-Targeting" approach is based on the equilibria outlined in Scheme 3.

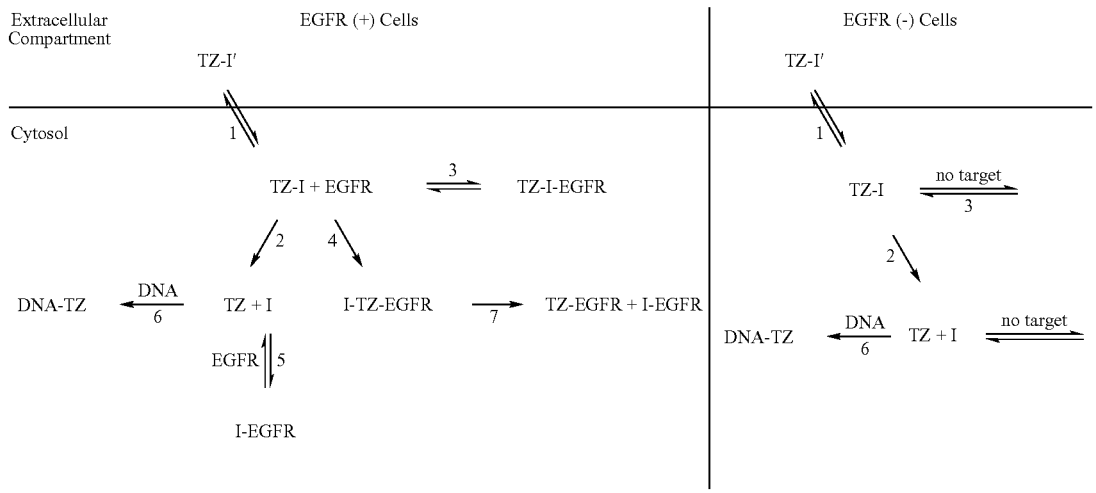

Scheme 3

As depicted in Scheme 3, the extracellular combi-molecules (TZ-I') diffuse across the cell membrane to the cytosol (see TZ-I). As previously mentioned, combi-molecules comprise a cytotoxic component (TZ) and an EGFR inhibitory component (I' or I). Once in the cytosol, the combi-molecules can either directly bind to the EGFR ATP-binding site to provide a TZ-I-EGFR complex (path 3), they can degrade to a cytotoxic molecule (TZ) and an EGFR TK inhibitor molecule (I) (path 2) or more importantly, they may directly alkylate EGFR (path 4). In the latter case, an inactivated covalently modified, irreversibly inhibited receptor (I-TZ-EGFR) is formed. If I loses its affinity for the damaged receptor, it is surmised that it is released so that it can subsequently bind to another undamaged EGFR ATP binding site to provide I-EGFR (path 7). While the TZ will exert cytotoxic activity by damaging DNA (see DNA-TZ), the generated inhibitor I is designed to inhibit EGFR-induced growth by binding to the EGFR ATP binding site to provide I-EGFR (see path 5). Blockade of signal transduction mediated by EGFR also down-regulates DNA repair enzymes (29). The combined cytostatic and cytotoxic effects lead to enhanced antiproliferative activity of the TZ-I combi-molecule in high EGFR-positive cells. In contrast, in EGFR-deficient cells (see EGFR (−)), no EGFR-directed growth inhibitory effects are expected because of the absence of an inhibitory target for TZ-I and I. These cells will therefore be less sensitive to the overall additive or synergistic dual mechanisms of action of the TZ-I molecules. Three critical parameters appear to contribute to the selectivity of a TZ-I conjugate: (a) the conjugate's stability, (b) the conjugate's affinity for the receptor, and (c) the potency of the released cytotoxic I.

The current invention is based on molecules having affinity for the EGFR and having the ability to target DNA. These novel compounds possess the ability to trigger a variety of events, the combination of which translate into irreversible growth inhibitory effects. The first event represents the interaction of the bulky conjugate with the receptor, whereas the second event constitutes the hydrolytic conversion of the conjugate into a less bulky inhibitor with the concomitant generation of a potent DNA damaging species.

The compounds of the present invention incorporate an anilinoquinazoline head to which is appended an alkylnitrosourea tail at the 6-position. The compounds were designed to be converted to their free aminoquinazoline precursors (which are potent inhibitors of EGFR) and a DNA damaging alkyldiazonium moiety upon hydrolysis. In addition, these compounds were designed to confer enhanced activity in tumor cells which may be resistant to agents containing the same pharmacophores.

The same principles will presumably apply to any combined compounds made up of a ligand to a protein involved in a cell proliferation signaling pathway and a DNA damaging agent. The ligand appears to not only facilitate the internalization of the combi-molecule, but also to block signal proliferation mediated by the oncoprotein and to increase the intracellular concentration of the DNA damaging fragments. In addition, blockade of signal transduction may down regulate DNA repair enzymes, thereby enhancing the cytotoxic effects of the DNA damaging moiety. Molecules other than EGFR [e.g. Her2 gene product p185, Her3, Her4 gene products, platelet-derived growth factor (PDGFR), bcr-abl tyrosine kinase, fibroblast growth factor (FGFR), angiogenic vascular endothelial growth factor (VEGF), receptor family members Flk1 or KDR, src family members and ligands other than SMA52 (e.g. quinazolines, tyrphostins, phenylaminopyrimidines, pyridopyrimidines, pyrrolopyrimidine derivatives)] are within the scope of the invention.

The terms and descriptions used herein are preferred embodiments set forth by way of illustration only, and are not intended as limitations on the many variations which those of skill in the art will recognize as possible in practicing the present invention.

Other objects, advantages and features of the present invention will become more apparent upon reading the following non-restrictive description of preferred embodiments with reference to the accompanying drawings.

BRIEF DESCRIPTION OF THE DRAWINGS

FIG. 4 shows a comparison between the anti-proliferative activities of FD-137 and the clinical drug BCNU in the AGT-expressing carcinoma of the vulva cell line A431 using a 4-day SRB assay.

FIG. 5a shows a comparison between the effects of SMA41, SMA52, and TEM on the growth of A431 cells using a 3-day SRB assay.

FIG. 5b shows a comparison between the effects of SMA41, SMA52, and TEM on the growth of A431 using a colony forming assay.

FIG. 12 shows the degradation of BJ2000 to FD105 by UV-spectroscopy (A) and by reverse phase HPLC analysis (B).

FIG. 15 illustrates reverse EGFR autophosphorylation in the presence of BJ2000, FD105 or TEM in A431 cells.

DESCRIPTION OF THE PREFERRED EMBODIMENTS

Figure 1:
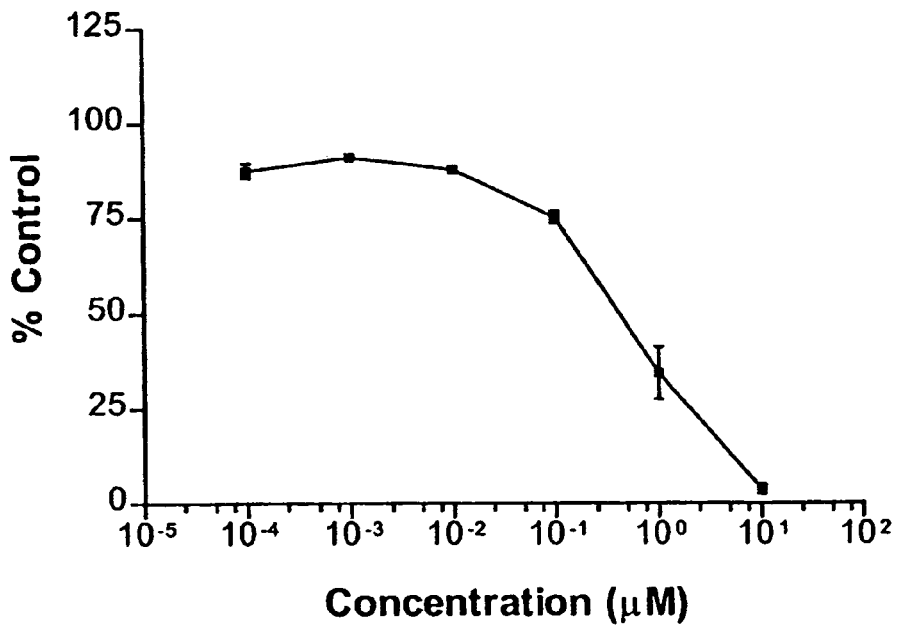
FIG. 1 shows a dose-response curve of the inhibition of poly(L-glutamic acid-L-tyrosine, 4:1) by FD137 using an ELISA to measure competitive binding at the ATP site.

The present invention comprises a series of new chemical agents that are capable of blocking EGFR-mediated signal transduction and that are capable of damaging DNA, thus demonstrating the potential to treat a variety of disease states involving EGFR and family members such as HER2, HER3 and HER4 gene products. Also included within the scope of the present invention is a general process for synthesizing these chemical agents.

In a preferred embodiment, the new chemical agents are represented by Formulas I and II, displaying EGFR mediated signal transduction blocking and causing DNA damage. Formula I ($R_1$=Me, Et, chloroethyl; Z=NO, H; $R_2$=H, Me, 8t, chloroethyl, hydroxyethyl; X=Cl, Br, I, methyl) and Formula II ($R_1$=Me, $CH_2OY$ (Y=H, acyl, thiophenol), acyl,

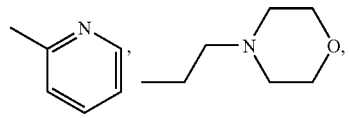

$MeOCH_2CH_2$—; $R_2$=H, Me; X=Cl, Br, I, methyl) were found to possess mixed EGFR TK and DNA targeting properties and superior antiproliferative properties when compared to their clinical counterparts TEM or BCNU.

Formula I

Formula II

Set forth below is a preferred synthesis scheme for the preparation of the molecules in accordance with the invention. The synthetic steps are set forth merely by way of example. Those skilled in the art will readily recognize alternative synthetic pathways and variations capable of producing a variety of derivatives of the compounds represented by formula I and II.

EXAMPLE 1

Process for the Preparation of Anilinoquinazolines

A reaction mixture composed of 2-amino-5-nitrobenzonitrile 1, formic acid and sulfuric acid was heated to yield cyclic compound 2. Intermediate 3 was obtained following a reaction with phosphorus pentachloiride and which was then further reacted with 3-toluidine to yield nitroanilinoquinazoline 4. The desired aminoanilinoquinazoline 5 was finally obtained via hydrogenation (Scheme 4).

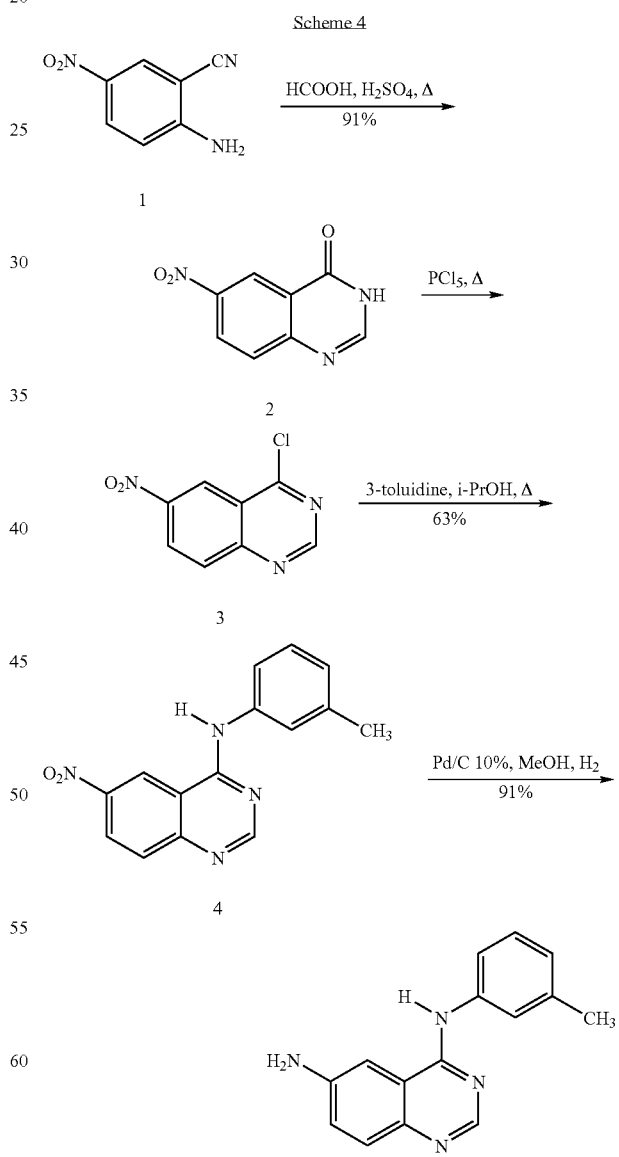

EXAMPLE 2
Process for the Synthesis of a First Series of Nitrosoureas Combi-Molecules
Aminoanilinoquinazoline 5 was treated with an 5 alkylisocyanate derivative to give the corresponding urea derivatives 6 (FD-89) and 8 (FD-141) which were subsequently nitrosylated using NOBF$_4$ in acetonitrile to provide the nitrosoureas 7 (FD-94) and 9 (FD-143).
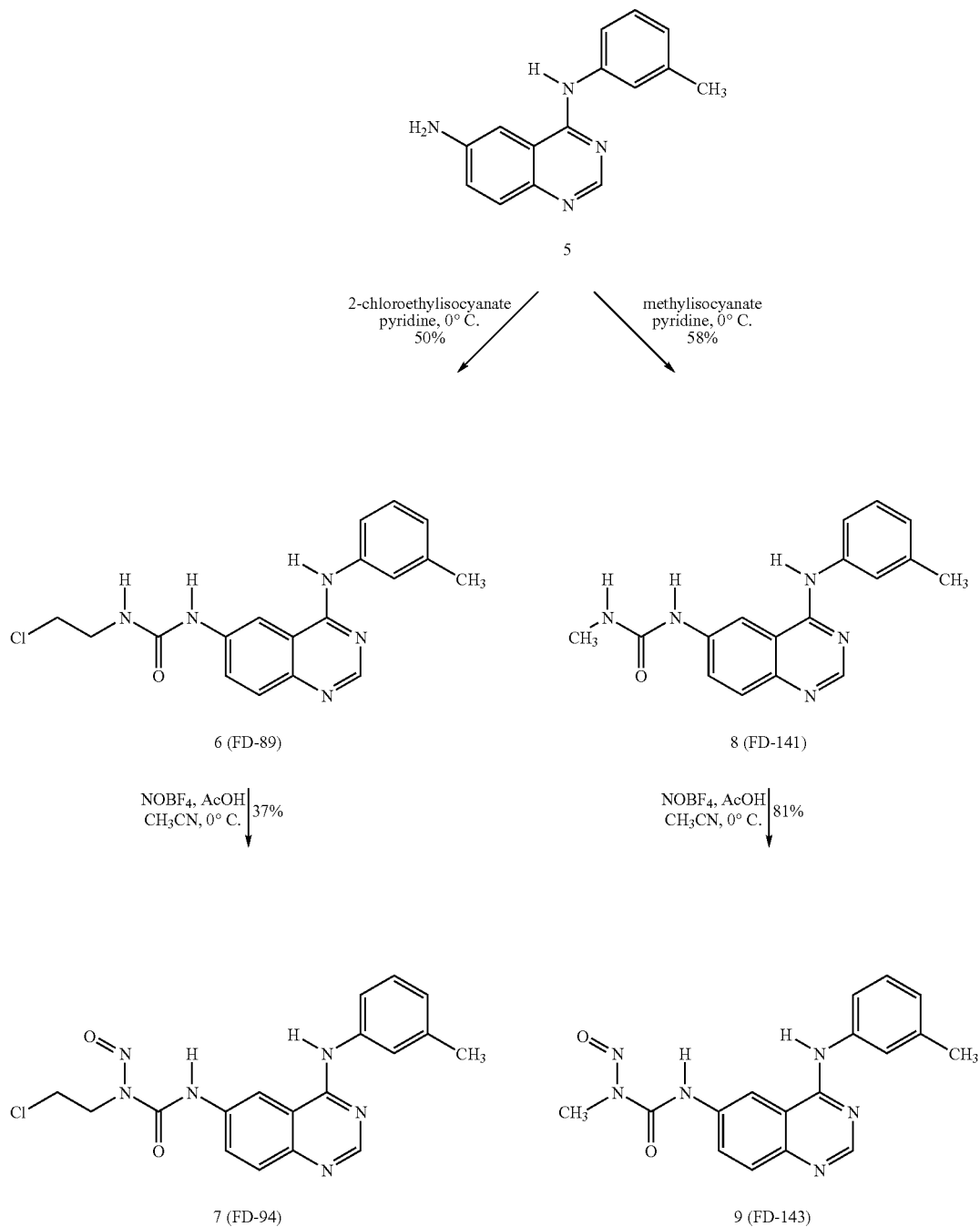
Scheme 5

EXAMPLE 3
Process for the Synthesis of a Second Series of Nitrosoureas Combi-Molecules
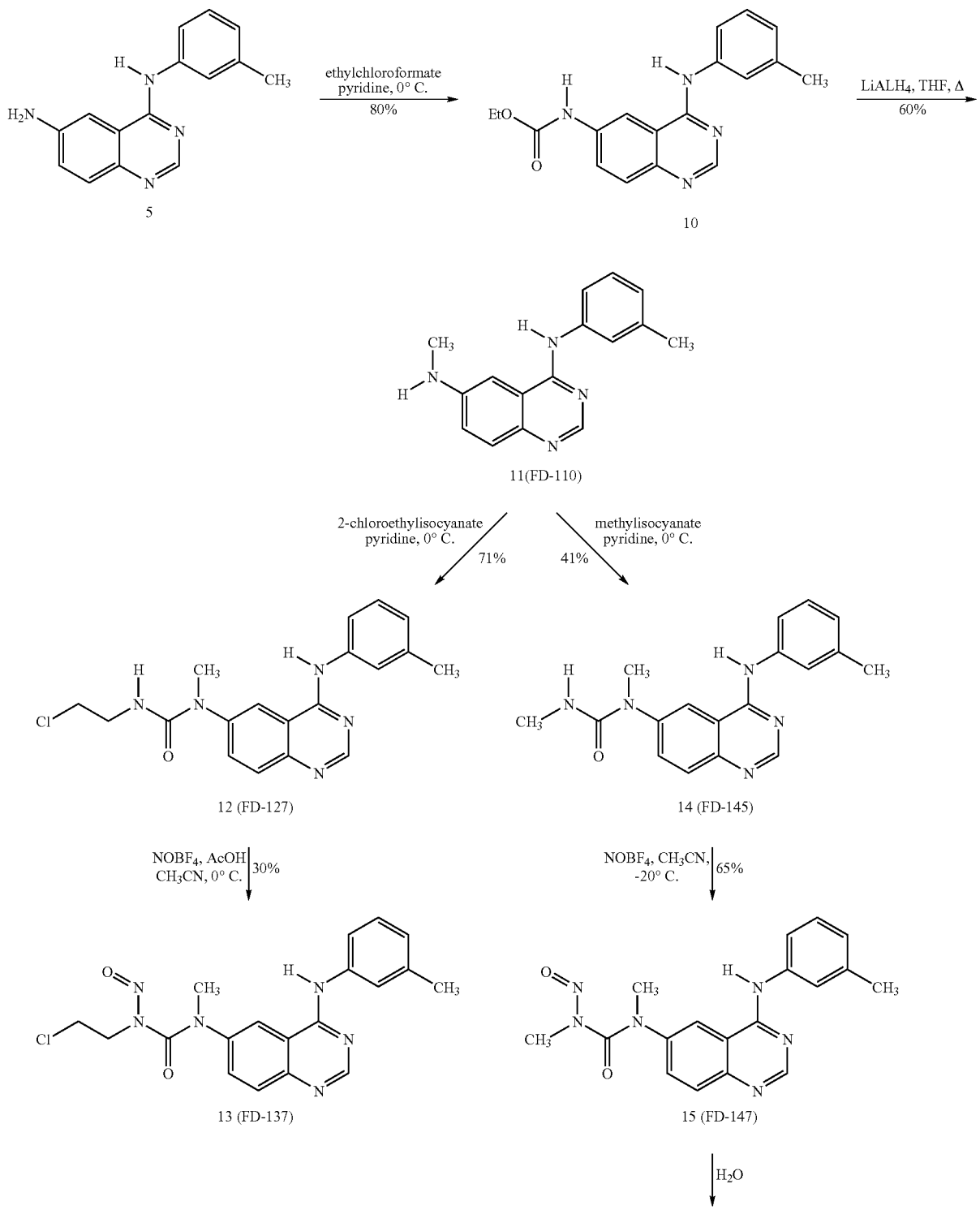
Scheme 6

-continued

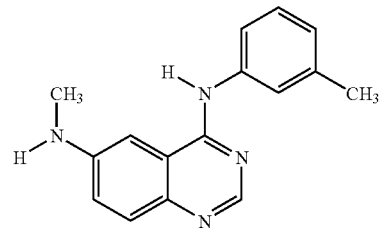

11 (FD-110)

To avoid the possible formation of isocyanates from the hydrolytic cleavage of the ureido moiety, as would occur in derivatives of types 7 and 9, the N3-methylated analogues 13 and 15 were synthesized. Standard methodology was applied to the synthesis of aminoanilinoquinazoline 11 henceforth referred to as FD110. Briefly, aminoanilinoquinazoline 5 was treated with ethylchloroformate to yield carbamate derivative 10, which was then reduced with LiAlH₄ to yield FD110.

Quinazoline 11 was reacted with an alkylisocyanate derivative to give the corresponding urea derivatives 12 (FD-127) and 14 (FD145) which were subsequently nitrosylated using NOBF₄ in acetonitrile, providing the nitrosoureas 13 (FD-137) and 15 (FD-147). HPLC studies of the decomposition of FD137 showed that it could regenerate FD110 upon hydrolysis.

EXAMPLE 4

Detailed Synthesis of FD-137

6-N-Methylaminoquinazoline 11 (0.4 g, 1.5 mmol) was dissolved in pyridine (3 ml) under argon at 0° C. After 15 min, 2-chloroethylisocyanate (0.13 ml, 1.1 equiv.) was added. The mixture was stirred overnight, and 5N HCl added. The resulting precipitate was filtered, washed with dichloromethane and further dried under vacuum to provide the N-(2-chloroethyl)-N'-methyl-N'-(4-m-tolylaminoquinazolin-6-yl)-urea 12 as a white powder (0.27 g, 48% yield): mp 150-151° C. (dec.); $^1$H NMR (DMSO) δ 9.61 (s, 1H, NH), 8.56 (s, 1H, H2), 8.45 (s, 1H, H5), 7.75 (d, 1H, H7), 7.65 (d, 2H, H8), 7.24 (d, 2H, J=8 Hz, H6', H2'), 6.95 (d, 1H, J=8 Hz, H4'), 6.63 (t, 1H, J=8 Hz, H5'), 3.57 (m, 2H, CH₂), 3.30 (s, 3H, NCH₃), 3.27 (m, 2H, CH₂), 2.33 (s, 3H, aniline CH₃); $^{13}$C NMR 158.4, 156.4, 143.2, 140., 139.2, 134.0, 130, 126.0, 124.0, 120.8, 120.4, 116.8, 44.0, 43.2, 37.6, 21.6; FABMS M+1 (I %), 369 (25), 263 (23), 154 (100), 136 (76)

The urea 12 (0.215 g, 0.6 mmol) was dissolved in acetonitrile (1 ml) and acetic acid (0.035 ml, 1 equiv) at 0° C., under argon. After 15 min, NOBF₄ (0.102 g, 1.5 equiv.) was added and the resulting red solution stirred for 4 h at 0° C. The solvent was evaporated and saturated NaHCO₃ (15 ml) was added on ice. Following extraction of the resulting cloudy solution, the organic layer was removed, dried over anhydrous potassium carbonate and evaporated under vacuum. The resulting pale yellow residue was purified on silica gel using 1% triethylamine in ethylacetate as an eluent to give N-(2-Chloroethyl)-N'-methyl-N'-(4-m-tolylaminoquinazolin-6-yl)-N-nitrosourea (FD137) as a pale yellow powder (0.07 g, 30%): mp 150-151° C. (dec); $^1$H NMR (DMSO) δ 9.80 (s, 1H, NH), 8.60 (s, 1H, H2), 8.55 (s, 1H, H5), 7.82 (d, J=8 Hz, 1H, H7), 7.76 (d, 1H, J=8 Hz, H8), 7.72 (t, 1H, J=8 Hz), 7.60 (d, 2H, J=8 Hz, H6', H2'), 6.95 (d, 1H, J=8 Hz, H4'), 4.13 (m, 2H, CH₂); 3.70 (m, 2H, CH₂), 3.60 (s, 3H, NCH3), 2.35 (s, 3H, aniline CH₃); $^{13}$C NMR 155.8, 142.5, 139.3, 134.0, 131.8, 131.1, 129.2, 125.9, 122.6, 119.1, 118.3, 115.5, 42.2, 41.7, 40.7, 21.8; FABMS M+1 (I %) 399, 263 (25), 54 (100), 136 (82).

EXAMPLE 5

Synthesis of the Combi-Triazene SMA41

To a solution of 6-amino-4-[(m-tolyl)amino]quinazoline 5 (1 g, 4 mmole) in acetonitrile (50 ml) were added 5 ml of acetic acid. The mixture was kept at 0° C. for 1 h after which a suspension of NOBF₄ (2 equiv.) in acetonitrile was added dropwise. Methyl amine was then added. The reddish solution was neutralized by addition of saturated sodium carbonate until a two-phase mixture was formed. Ethyl acetate (200 ml) was added and the aqueous layer removed. The resulting pale brown ethyl acetate solution was dried over anhydrous potassium carbonate and evaporated under vacuum to give a brown oil which was re-dissolved in a minimum volume of the same solvent. Hexane was added by portion until a persistent pale brown precipitate was formed. The mixture was filtered and the resulting precipitate collected by filtration, dried under vacuum to provide the monoalkyltriazene SMA41 as a pale brown powder (0.7, 60%): mp 75-80° C. (dec.); $^1$H NMR (DMSO) δ 10.67 (br q, 1H, NHCH₃), 9.74 (s, 1H, NH), 8.51 (s, 1H, H2), 8.47 (s, 1H, H5), 7.9 (d, 1H, J=9, H7), 7.70 (br s d, 3H, H2', H6', H8, overlap), 7.24 (t, 1H, J=7.5 Hz, H5'), 6.90 (d, 1H, J=7.5 Hz, H4'), 3.07 (d, 3H, J=4, HNCH₃), 2.31 (s, 3H, ArCH₃); $^{13}$C NMR 158.4, 154.1, 149.9, 148.7, 140, 138.1, 129.4, 128.879, 125.3, 124.8, 123.7, 123.4, 120.0, 116.4, 115.3, 31.3, 21.9; FABMS M+1 (I %) 293 (43), 250 (14), 234 (12).

EXAMPLE 6

Mixed Targeting Properties (i) Hydrolytic Conversion of the Bulky Conjugate Into a Less Bulky Inhibitor The ability of FD137 to generate the intact inhibitor was demonstrated by HPLC analysis, which showed the appearance of a peak corresponding to the known inhibitor 11 (FD110) following overnight decomposition of FD137 in a cell culture medium.

(ii) Interactions of the Conjugate with the EGF Receptor

The ability of the combi-molecules to block EGFR TK activity was determined by an ELISA assay using poly(L-glutamic acid-L-tyrosine, 4:1) PGT as a substrate and commercially available EGFR.

Nunc MaxiSorp 96-well plates were incubated overnight at 37° C. with 100μL per well of 0.25 mg/mL PGT in PBS. Excess PGT was removed and the plates were washed 3 times with Tween 20 (0.1%) in PBS. The kinase reaction was performed as previously described using 15 ng/well of EGFR, affinity-purified from A431 cells (30) (generous gift from Pfizer Inc, NJ and commercial supplies from BIOMOL, Plymouth meeting, CA). The compound was added and phosphorylation initiated by the addition of ATP (20 μM). After 8 min at room temperature with constant shaking, the reaction was terminated by the aspiration of the reaction mixture and by rinsing the plate 4 times with wash buffer (Tween 20 (0.1%) in PBS). Phosphorylated PGT was detected following a 25 min incubation with 50 μL per well of HRP conjugated PY54 antiphosphotyrosine antibody, diluted to 0.2 μg/mL in blocking buffer (3% BSA; 0.05% Tween 20 in PBS). Antibody was removed by aspiration, and the plates washed 4 times with wash buffer. The signals were developed by the addition of 50 μL per well of TMB peroxidase substrate (Kierkegaard and Perry Laboratories, Gaithersberg, Md.). Following blue color development, 50 μL of $H_2SO_4$ (0.09 M) was added per well, and the plates read at 450 nm using a Bio-Rad ELISA reader (Model 2550).

The results illustrate that combi-molecule FD137 inhibits EGFR TK ($IC_{50}$~1 μM) in a dose-dependent manner (FIG. 1). It is noteworthy that the EGFR TK binding affinity of FD137 is less than that of free ligand 11 (FD110) ($IC_{50}$~0.05 μM). This demonstrates the feasibility of a receptor-affinative conjugate TZ-I (e.g FD137) capable of degrading to a less bulky inhibitor I (FD110) possessing stronger affinity for the same receptor (as postulated for SMA41 in Scheme 2).

(iii) Generation of a Potent DNA Damaging Species

The DNA damaging properties of FD137 were determined by the comet assay in the A431 carcinoma of the vulva cell line that overexpresses EGFR and co-expresses the DNA repair enzyme 06alkylguanine DNA alkyl transferase (AGT). Cells that express AGT are resistant to BCNU. The results illustrate that FD137 could generate a dose-dependent increase in DNA single strand breaks in these cells. This indicates that FD137 is successful in overcoming the cell resistance to DNA alkylating agents.

(iv) Alkaline Comet Assay for Quantitation of DNA Damage

A modified alkaline comet assay technique (31) was used to quantitate DNA damage induced by SMA41, SMA52, and TEM. A431 cells were exposed to drugs for 30 min or 2 h, and harvested with trypsin-EDTA. The cells were subsequently collected by centrifugation and re-suspended in PBS. The resulting cell suspension was diluted to approximately $10^6$ cells, and mixed with agarose (1%) in PBS at 37° C. in a 1:10 dilution. The gels were cast on Gelbond strips (Mandel Scientific, Guelph, Canada) using gel casting chambers, as previously described (32), then immediately placed into a lysis buffer [2.5 M NaCl, 0.1 M tetra-sodium EDTA, 10 mM tris-base, 1% (w/v) N-lauryl sarcosine, 10% (v/v) DMSO and 1% (v/v) Triton X-100]. After being kept on ice for 30 min, the gels were gently rinsed with distilled water and then immersed in a second lysis buffer [2.5 M NaCl, 0.1 M tetra-sodium EDTA, 10 mM tris-base], containing 1 mg/ml proteinase K for 60 min at 37° C. Thereafter, the gels were rinsed with distilled water, incubated in alkaline electrophoresis buffer for 30 min at 37° C., and electrophoresed at 300 mA for 60 min. The gels were subsequently rinsed with distilled water and placed into 1 M ammonium acetate for 30 min. They were further soaked in 100% ethanol for 2 h, dried overnight and subsequently stained with SYBR Gold (1/10000 dilution of stock supplied from Molecular Probes, OR) for 20 min. For evaluation of comets, DNA damage was assessed using the Tail Moment parameter (i.e. the product of the distance between the barycentres of the head and the tail of the comet. A minimum of 50 cell comets were analyzed for each sample using ALKOMET v3.1 software, and values are an average of tail moments for the entire cell population.

Figure 2:
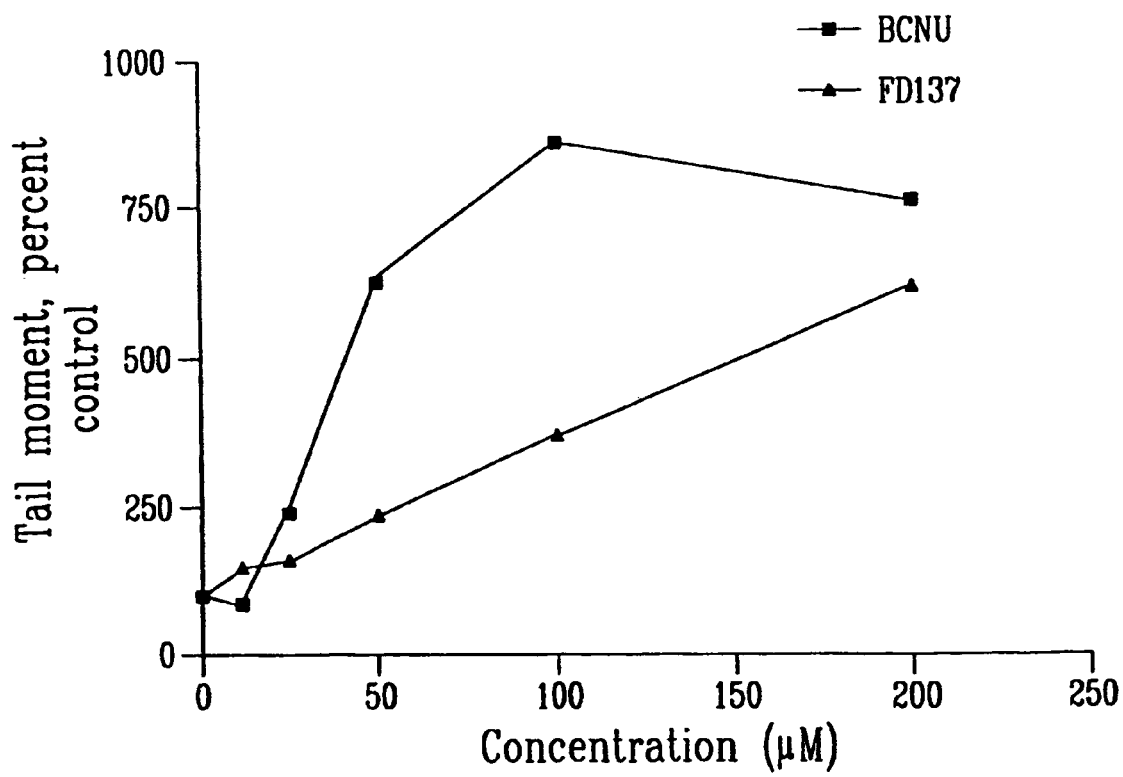
FIG. 2 illustrates a comparison between levels of DNA damage induced by BCNU and FD137 using a single-cell alkaline microelectrophoresis comet assay.
Figure 3:
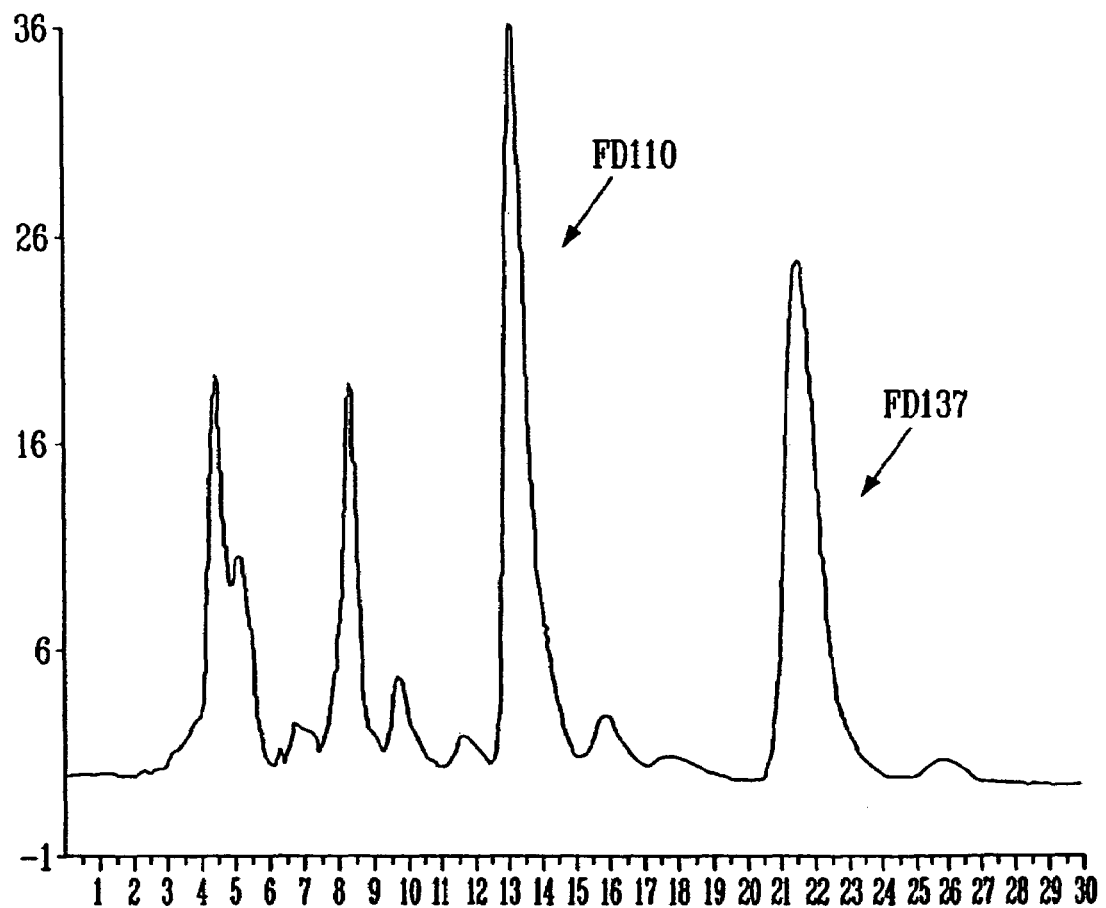
FIG. 3 shows an HPLC chromatogram of the partial conversion of FD137 into the inhibitor FD110 following incubation in serum containing media at 37° C.

The results illustrate that FD137 could generate a dose-dependent increase in DNA single strand breaks in these cells which indicates that in addition to its ability to inhibit EGFR tyrosine kinase, FD137 possesses significant DNA damaging properties (FIG. 2). In contrast to BCNU, combi-molecule FD137 appears to be a mild alkylating agent, generating lower levels of DNA lesions than BCNU (FIG. 2).

These two lines of experiments (EGFR TK inhibition) and comet assay demonstrate that FD137 possesses mixed EGFR-DNA targeting properties.

Figure 21A:
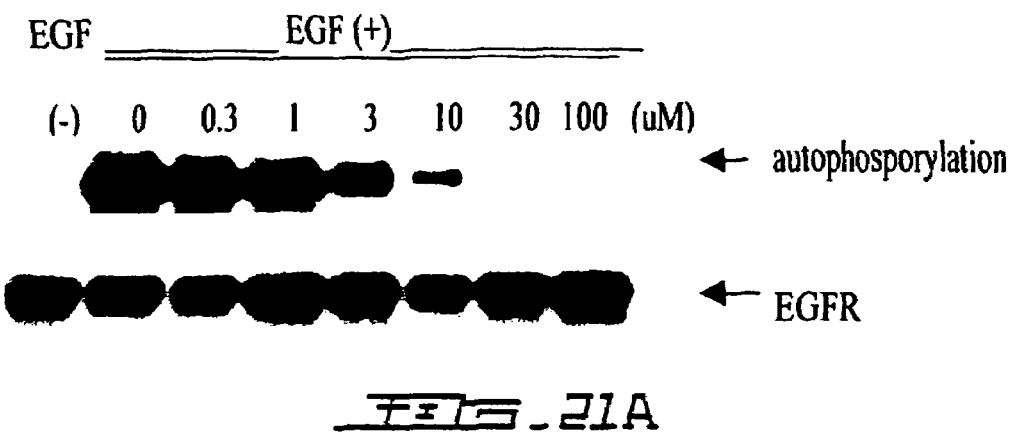
FIG. 21 is a Western blot illustrating the effect of FD137 (A) and BCNU (B) on the inhibition of EGF-stimulated EGFR autophosphorylation in A431 cells.
Figure 21B:
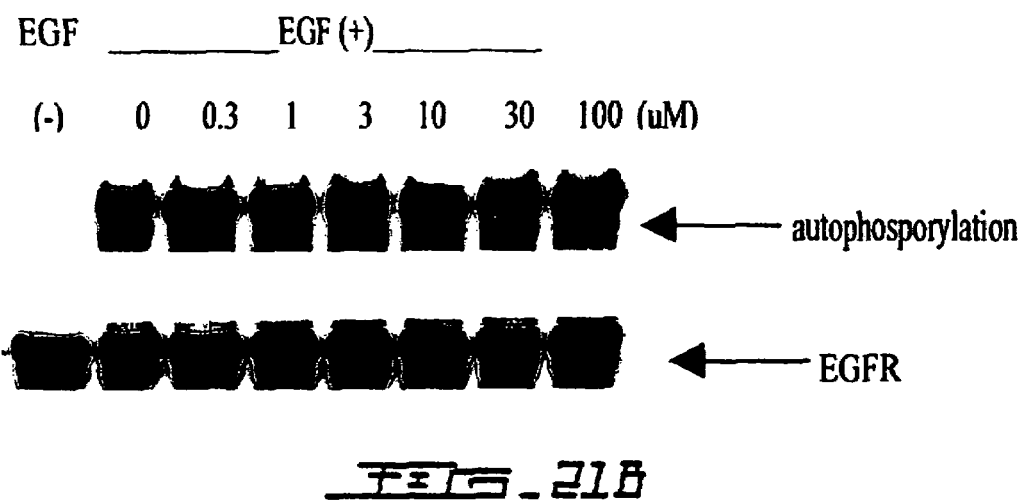

(v) Efficacy in Tumor Cell Growth Inhibition in Comparison with the Clinical Lead Drug BCNU All growth inhibitory activities were evaluated using the SRB assay (33). Briefly, following drug treatment, cells were fixed using 50 μL of cold trichloroacetic acid (50%) for 60 min at 4° C., washed five times with tap water, and stained for 30 min at room temperature with SRB (0.4%) dissolved in acetic acid (0.5%). The plates were rinsed five times with 1% acetic acid and allowed to air dry. The resulting colored residue was dissolved in 200 μL of Tris base (10 mM), and the optical density read for each well at 540 nm using a Bio-Rad microplate reader (model 2550). Each point represents the average of at least two independent experiments run in triplicate Using a 4-day sulforhodamine B assay, FD137 ($IC_{50}$, 0.8 μM) was demonstrated to be 50-fold more potent than the clinical drug BCNU ($IC_{50}$, 40 μM) in the resistant AGT-expressing A431 cell line which also co-expresses high levels of EGFR (see FIG. 1) and its ligand TGFα inducing an aggressive autocrine controlled growth. These results illustrate the potency of a nitrosourea compound possessing mixed targeting properties in the inhibition of tumor cell growth in a sulforhodamine B assay. Perhaps, the ability of FD137 and its metabolite FD110 to block TGFα-mediated signaling in these cells may down regulate DNA repair enzymes capable of reversing DNA lesions induced by the N-nitroso-N-2-chloroethyl fragment generated following the hydrolysis of FD137. This culminates in an enhanced potency of the combi-molecule when compared with its clinical nitrosourea counterpart BCNU. The enhanced potency of FD137 can also be rationalized by an additive or synergistic effect produced by its binary mechanism of action: cytostatic growth inhibition associated with blockade of EGFR-mediated signaling and cytotoxicity induced by DNA lesions. Additionally, combi-molecule FD137 in contrast to BCNU, blocked EGFR autophosphorylation in A431 cells in a dose dependent manner (FIG. 21).

EXAMPLE 7

Drug Treatment

SMA41 and SMA52 were synthesized in our laboratories according to known procedures (34). TEM, the lead drug of the triazene-containing imidazotetrazine class which is now approved in the USA for the treatment of brain tumors and in Europe for the treatment of both glioma and brain tumors (see TEM, Scheme 1). TEM was provided by Shering-Plough Inc. (Kenilworth, N.J.). In all assays, combi-molecules or TEM was dissolved in DMSO and subsequently diluted in sterile RPMI-1640 media containing 10% fetal bovine serum (Life Technologies, Burlington, Canada) immediately prior to the treatment of the cell cultures. In all assays, the concentration of DMSO never exceeded 0.2% (v/v).

BJ2000 and FD105 were synthesized in our laboratories according to known procedures (34). Temozolomide was provided by Shering-Plough Inc. (Kenilworth, N.J., USA). In all of the assays, the drug was dissolved in DMSO and subsequently diluted in sterile RPMI-1640 containing 10% fetal bovine serum (FBS) (Wisent Inc. St-Bruno, Canada) or in DMEM containing 10% bovine calf serum (GIBCO BRL, Burlington, Canada) immediately prior to treatment of the cell cultures. In all assays, the concentration of DMSO never exceeded 0.2% (v/v).

EXAMPLE 8

Cell Culture

The cell lines used in this study, the human epidermoid carcinoma of vulva A431 cells were obtained from the American Type Culture Collection (Manassas, Va., RF33613). The A431 cell line was maintained in a monolayer culture at 37° C. in a humidified environment of 5% $CO_2$-95% air. The cultures were maintained in RPMI-1640 supplemented with fetal bovine serum (10%), penicillin (50 U/mL), and streptomycin (50 mg/mL) (Life Technologies, Burlington, Canada). Cells were maintained in logarithmic growth by harvesting with a trypsin-EDTA solution containing 0.5 mg/mL of trypsin and 0.2 mg/mL of EDTA and replating before confluence. In all assays, the cells were plated for 24 h before drug administration. The mouse fibroblasts NIH3T3 and NIH3T3HER14 (NIH3T3 cells stably transfected with EGFR gene) were generous gifts from Dr. Moulay Aloui-Jamali of the Montreal Jewish General Hospital. NIH3T3 and NIH3T3HER14 cells were maintained in DMEM supplemented with 10% bovine calf serum and antibiotics.

EXAMPLE 9

Growth Inhibition Studies (i) Comparison with Free Inhibitor SMA52 and TEM

The SRB assay was used to evaluate the antiproliferative activity of different compounds in the human squamous carcinoma of the vulva cell line A431, in which EGFR constitutive activity, as reflected by tyrosine phosphorylation under basal conditions, has been shown to be sensitive to antiproliferative agents targeting the EGFR in vitro or in vivo (35). In addition, this cell line expresses detectable levels of the DNA repair enzyme MGMT (36). The MGMT status of our A431 cell line was also confirmed by western blotting using a commercially available anti-MGMT antibody (Pharmingen International, Toronto, Canada) (data not shown). After 72 h of continuous exposure, the results illustrated by FIG. 5a showed that SMA41 is 1.8-fold more potent ($IC_{50}$=36 µM) than its metabolite SMA52 alone ($IC_{50}$=59 µM) and 10-fold more potent than TEM ($IC_{50}$=366 µM) in the MGMT-proficient cell line A431.

Colonogenic assays were performed as previously described (37). Briefly, cells were plated at a density of 500 cells/well and continuously exposed to each drug for 6 days. Colonies were fixed with methanol (100%) and stained with methylene blue (0.5%) after which they were counted with the SynGene GeneTools colony counting software package (Cambridge, UK). Only colonies with pixel areas of 4 or greater were counted. Data are means and SD's of two independent determinations.

As illustrated by FIG. 5b, the antiproliferative activity of SMA41 was in the same range as that of SMA52 ($IC_{50}$ SMA41 4 µM, $IC_{50}$ SMA52 3.7 µM) but significantly greater that of TEM which showed no activity over the whole dose range.

(ii) Comparison with an SMA52+TEM Combination

For the SMA52+TEM combination, the drugs were mixed at a 1:7 (SMA52/TEM) molar ratio, serially diluted and added to the monolayers for 72 h. The nature of drug interactions was determined using Equation 1 where $CI_{50}$>1, =1 or <1 indicates antagonism, additivity, or synergism, respectively (38).

$$CI_{50} = \frac{IC_{50}(TEM \text{ in combination})}{IC_{50} \ (TEM \ \text{alone})} + \frac{IC_{50} \ (SMA52 \text{ in combination})}{IC_{50} \ (SMA52 \text{ alone})}$$

Figure 5C:
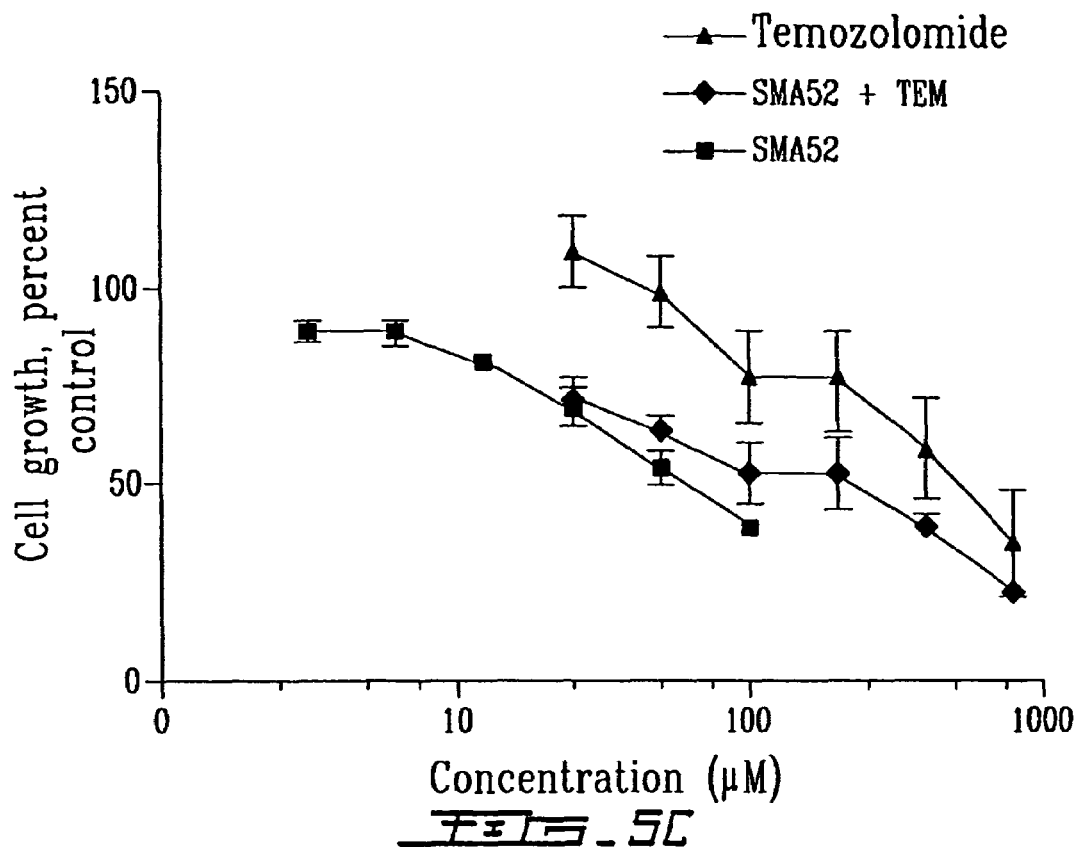
FIG. 5c shows a series of dose-response curves demonstrating the antiproliferative effects of a SMA52+TEM combination in A431 cells using the SRB assay.

In order to demonstrate the antiproliferative advantages of combining the EGFR and DNA targeting mechanisms in a single molecule, the combined effect of SMA52 (independently synthesized) with that of TEM was studied using the SRB assay (FIG. 5c). Using Equation 1 to determine the nature of the interactions between these two drugs, the results showed that the combination index at the 50% effect ($CI_{50}$) for SMA52+TEM, is approximately 0.6, indicating a subadditive interaction. However, under identical conditions the antiproliferative activity of the combi-molecule SMA41 was 4-fold more pronounced than that of the 2-drug combination, indicating that the combination of the two mechanisms of action in a single combi-molecule has a significant pharmacologic advantage.

(iii) Reversibility of the Antiproliferative Activity of SMA41

Figure 6A:
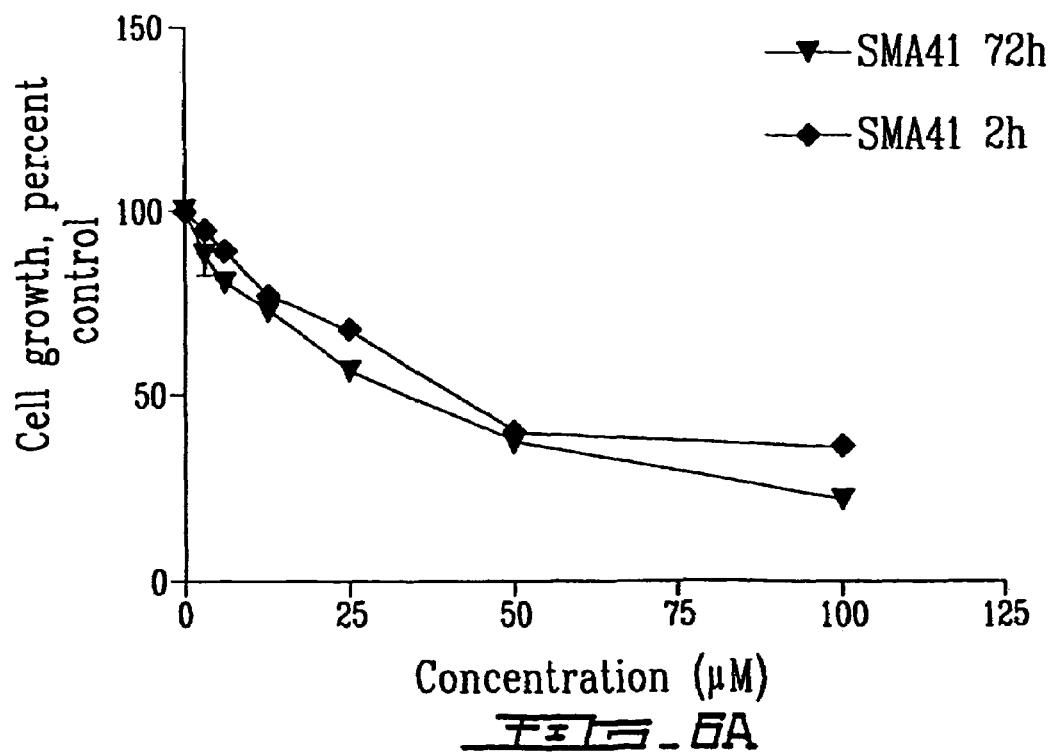
FIG. 6 shows a comparison between the reversibility of the antiproliferative effects of SMA41, SMA52 and TEM on A431 cells following a short 2 h exposure and a 3-day recovery or a continuous 72 h exposure using the SRB B assay.
Figure 6B:
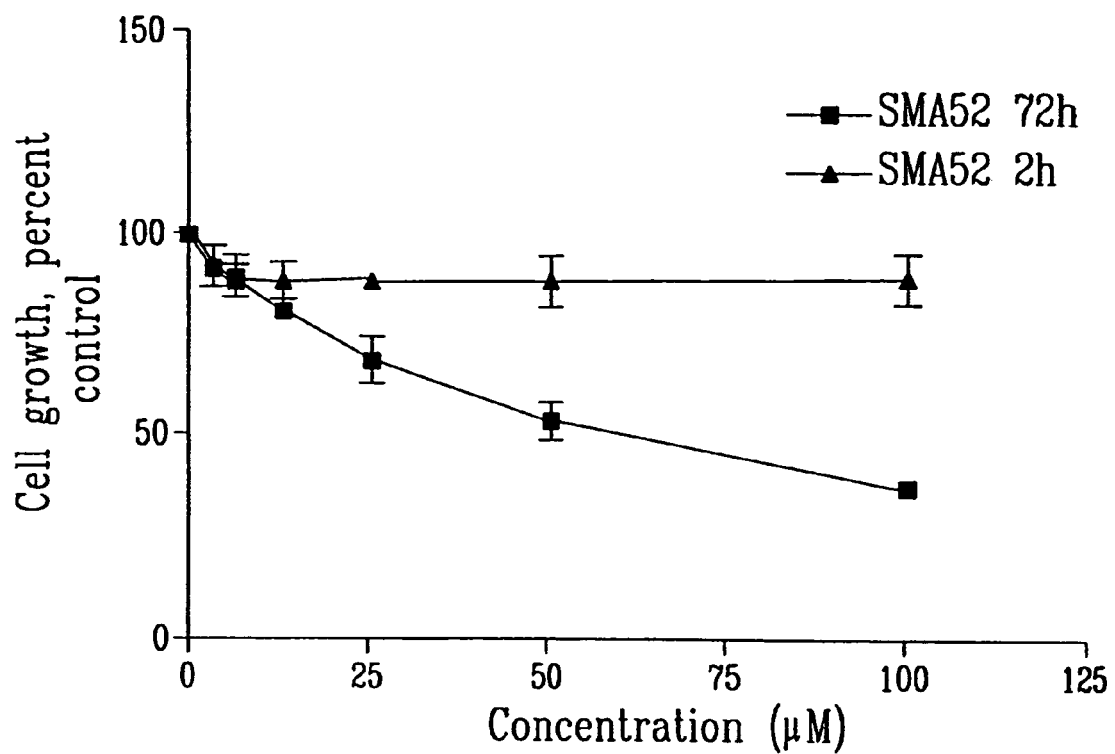
Figure 6C:
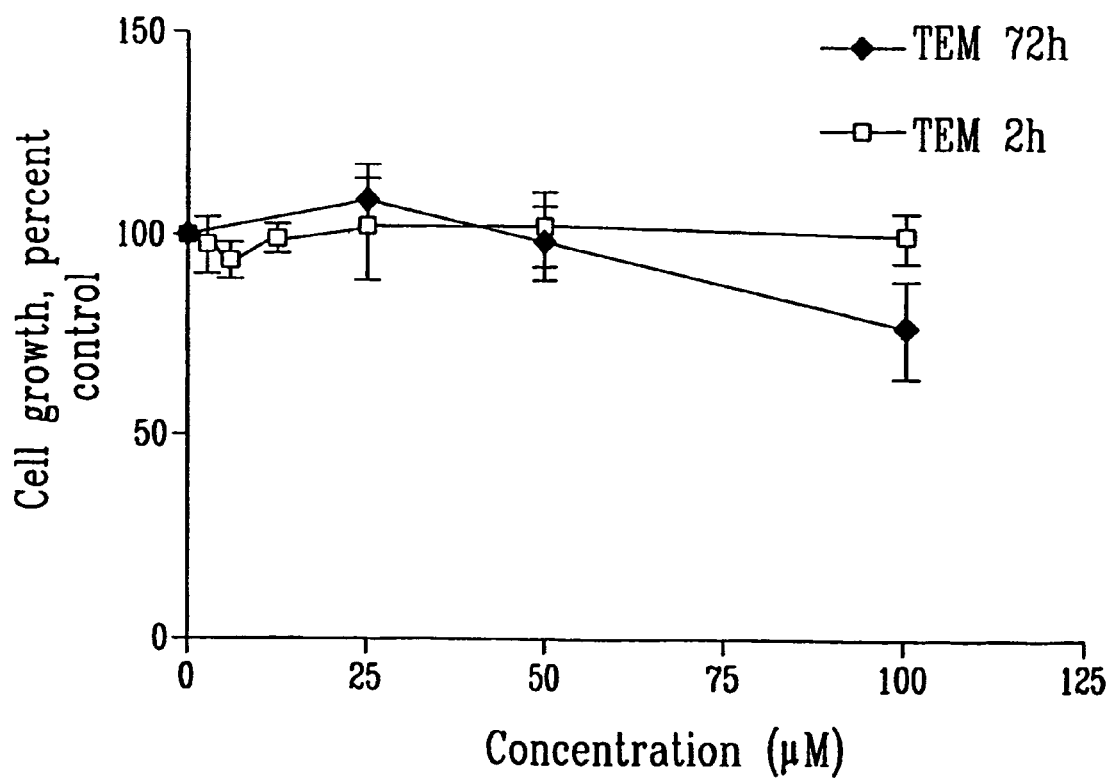

Cell monolayers were continuously exposed to different concentrations of each drug for 72 h. Under short exposure, they were treated with each drug for 2 h and allowed to recover for 72 h in drug-free medium. When the cells were treated for only 2 h and further incubated in drug-free medium, an almost complete loss of activity was observed for SMA52 ($IC_{50}$>100 µM, FIG. 6b), indicating that it induced significantly reversible growth inhibitory activities. In contrast, SMA41 showed significant retention of activity with little change in the $IC_{50}$ values [$IC_{50}$ (2 h)=36 µM, $IC_{50}$ (72 h)=~30 µM] FIG. 6a). Temozolomide was inactive under both short and continuous exposure (FIG. 6c).

EXAMPLE 10

Degradation

SMA41 (1 mg) was dissolved in DMSO (500 µL), added to RPMI with 10% fetal bovine serum (2 mL) and incubated for 24 h at 37° C. Thereafter, proteins were precipitated by the addition of acetonitrile (3.5 ml) and the supernatant collected by centrifugation. The concentration of SMA52 derived from the degradation of SMA41 was calculated using a standard curve obtained from the serial dilution of independently synthesized SMA52 incubated in serum-containing medium under identical conditions. HPLC analyses were performed on a Hewlett-Packard 1090 liquid chromatograph using a Deltapak C4 15 µm 300×3.9 mm column (reverse phase) to characterize and quantitate the products resulting from the degradation of SMA41. The operating mode was isocratic and two solutions, "A" (50% acetonitrile) and "B" (50% water), were used with a 0.5 ml/min flow rate and a 5 μL injection volume. Under these conditions, independently synthesized SMA52 and SMA41 showed retention times of 11 and 15 min, respectively. For the rapid quantitation of metabolite, a less polar acetonitrile-water (70:30) eluent was used. Under these conditions SMA52 showed a retention time of 7.49 min. For LC-MS analysis of the degradation of SMA41, the column was placed on a Spectra System P1500 HPLC coupled with a Finnigan LCQDUO mass spectrometer.

The half-life of SMA41 under physiological conditions was studied by UV spectrophotometry using an Ultrospec 2000 Pharmacia Biotech spectrophotometer. SMA41 was dissolved in a minimum volume of DMSO, diluted with RPMI medium supplemented with 10% serum and absorbances read at 340 nm in a UV cell maintained at 37° C. with a circulating water bath. The half-life was estimated by a one-phase exponential decay curve-fit method using the GraphPad software package (GraphPad Software, Inc., San Diego, Calif.).

Figure 7:
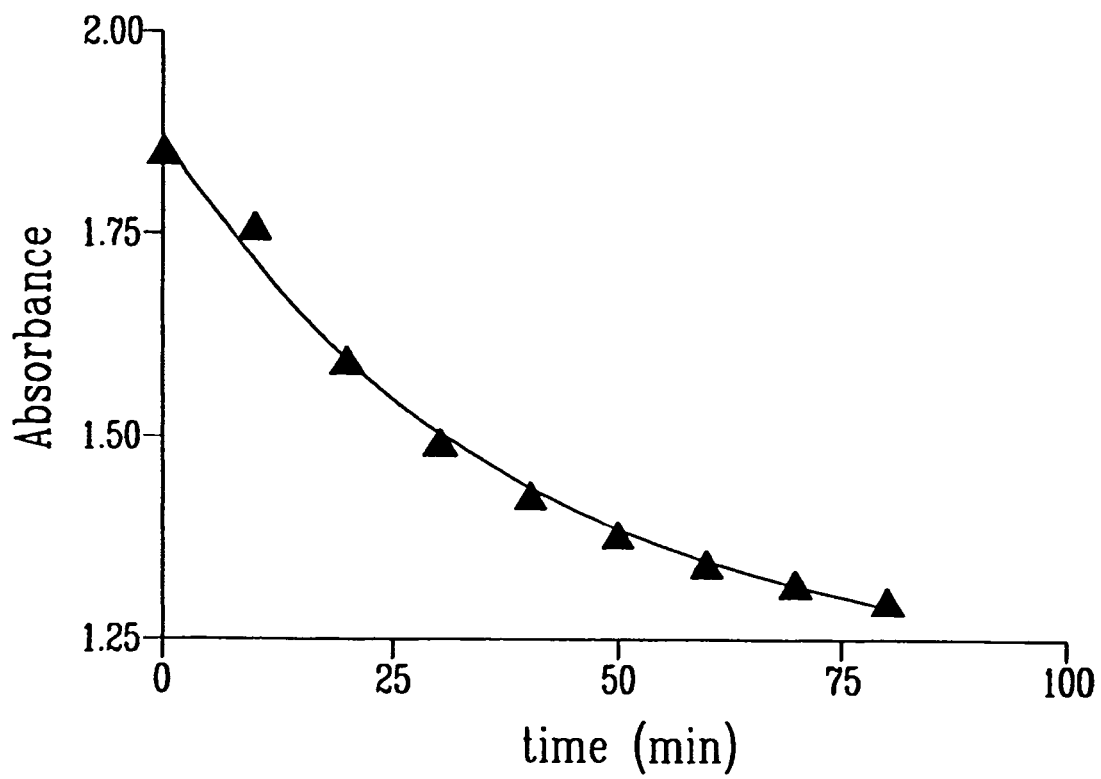
FIG. 7 shows a one-phase exponential decay curve describing the degradation of SMA41 in RPMI medium supplemented withh 10% serum at 37° C.
Figure 8:
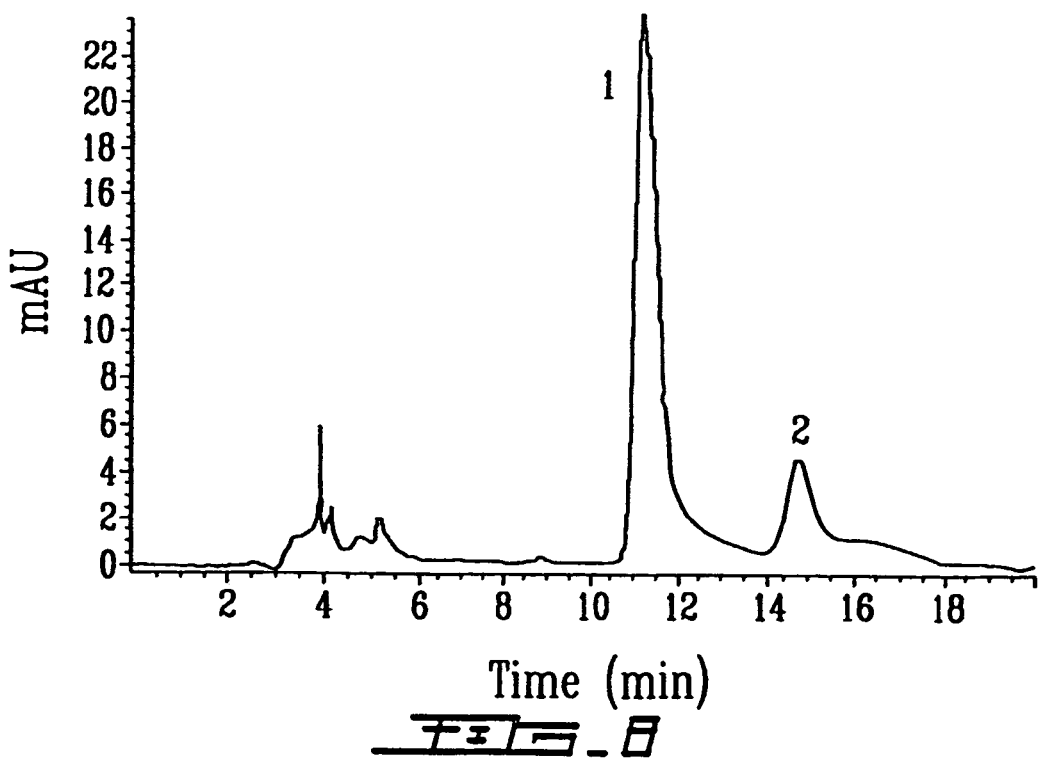
FIG. 8 shows a chromatogram of the partial conversion of SMA41 into SMA52 in RPMI medium supplemented with 10% serum at 37° C. Peak 1 representing SMA52 and peak 2 SMA41.

SMA41 was found to be significantly stable with a $t_{1/2}$ of approximately 30 min in serum-containing cell culture medium at 37° C. (FIG. 7). SMA41 decomposed almost exclusively into SMA52 (FIG. 8), the structure of which was confirmed both by HPLC analysis of independently synthesized SMA52 and by LC-MS analyses which showed a mass M+1=251 for the chromatogram peak corresponding to the retention time of SMA52. Quantification of this peak and calculations using standard curves indicated that SMA41 was converted to SMA52 in a yield of approximately 81%.

The half-life of BJ2000 under physiological conditions was studied by UV-spectrophotometry. BJ2000 was dissolved in a minimum volume of DMSO, diluted with RPMI-1640 supplemented with 10% FBS, and absorbencies read at 340 nm in a UV cell maintained at 37° C. with a circulating water bath. The half-life was estimated by a one-phase exponential decay curve-fit method, using the GraphPad software package (GraphPad software, Inc., San Diego, Calif., USA).

The HPLC study of the conversion of BJ2000 into FD105 was performed by adding BJ2000 (625 μM) to RPMI-1640 with 10% FBS (2 ml) followed by different incubating periods at 37° C. Proteins were thereafter precipitated by the addition of acetonitrile (3.5 ml), and the supernatant collected by centrifugation. The concentration of FD105 resulting from the degradation of BJ2000 was calculated using a standard curve that was obtained from the serial dilution of independently synthesized FD105, incubated in serum-containing medium under identical conditions. HPLC analyses were performed on a Hewlett Packard 1090 liquid chromatograph, using a Waters C4 15-μm 300×3.9-mm reverse phase column to characterize and quantitate the products resulting from the degradation of BJ2000. The operating mode was isocratic and two solutions, "A" (53% acetonitrile) and "B" (47% water) were used with a 0.5 ml/min flow rate and 10 μl injection volume. The peaks were detected at 250 nm. Under these conditions, independently synthesized FD105 and BJ2000 showed retention times around 10.5 and 15.2 min, respectively.

The half-life of BJ2000, measured by UV-spectrophotometry at 340 nm, was 34 min in RPMI-1640 supplemented with 10% FBS at 37° C. However it was noted that the absorbance at this wavelength reached early saturation at high absorbance units, e.g. 0.6 (FIG. 12A). The half-life study was therefore performed with HPLC analysis, whereby the decreasing and increasing peaks associated with the disappearance of BJ2000 and the appearance of FD105, could be clearly monitored. As expected, an inverse relationship was observed between the areas of the peaks associated with these two species, with an observed half-life of 75 min for BJ2000. Calculations based upon the area/concentration standard curve [Area=2.796×(concentration)−38.65; $R^2$=0.99] indicated that BJ2000 was converted to FD105 in 87% yield after a 24 h incubation in RPMI-1640, supplemented with 10% FBS at 37° C. (FIG. 12B).

EXAMPLE 11

Kinase Assays for BJ2000

(i) EGFR Kinase Assay

This assay is similar to the one previously described. Nunc MaxiSorp 96-well plates were incubated overnight at 37° C. with 100 μl/well of 25 ng/ml PGT in PBS. Excess PGT was removed and the plates were washed three times with wash buffer (Tween 20 (0.1%) in PBS). The kinase reaction was performed by using 4.5 ng/well of EGFR, affinity-purified from A431 cells (29). The compound was added and phosphorylation initiated by the addition of ATP (20 μM). After 8 min at room temperature with constant shaking, the reaction was terminated by aspirating the mixture and by rinsing the plates four times with wash buffer Tween 20 (0.1%) in PBS. Phosphorylated PGT was detected following a 25 min incubation with 50 μl/well of HRP-conjugated PY20 antiphosphotyrosine antibody (Santa Cruz Biotechnology, CA), diluted to 0.2μg/ml in blocking buffer (3% bovine serum albumin; 0.05% Tween 20 in PBS). Antibody was removed by aspiration, and the plate washed four times with wash buffer. The signals were developed by the addition of 50 μl/well of 3,3',5,5'-tetramethylbenzidine (TMB) peroxidase substrate (Kierkegaard and Perry Laboratories, Gaithersberg, Md., USA). Following blue color development, 50 μl of $H_2SO_4$ (0.09 M) was added per well, and the plates read at 450 nm using a Bio-Rad ELISA reader (Model 2550). The results illustrate that combi-molecule BJ2000 inhibits EGFR TK in a dose dependent manner (IC50=0.1 μM). It is noteworthy that the EGFR TK binding affinity of BJ2000 is less than that of free ligand (FD105) (IC50=0.2 μM). This demonstrates the feasibility of a receptor-affinative conjugate TZ-I (e.g BJ2000) capable of degrading to a less bulky inhibitor I (FD105) possessing stronger affinity for the same receptor (as postulated for BJ2000 in Scheme 2).

(ii) c-Src and Insulin Kinase Assays

Conditions for the c-src and insulin kinase assays were similar to those of the EGFR kinase assay, with the exception of the addition of 1 mM manganese chloride to the assay buffer, and a final ATP concentration of 100 μM. The reaction was terminated by the addition of 50 μl of a 250 mM solution of EDTA prior to aspiration. In experiments comparing the inhibition of EGFR with c-src-kinase or insulin receptor, Baculovirus-expressed human c-src (1.2 units/well, Upstate NY) or Baculovirus-expressed cytoplasmic domain of the insulin receptor β subunit (15 ng/ml, Biomol Research laboratories Inc., USA) was substituted for the EGFR. As positive controls, PP1 (Biomol Research Laboratories Inc.), a selective inhibitor of c-src ($IC_{50}$=170 nM) and HNPMA-(AM)$_3$ (Biomol Research Laboratories Inc.), an inhibitor of insulin receptor ($IC_{50}$=100 μM), were used.

Figure 13C:
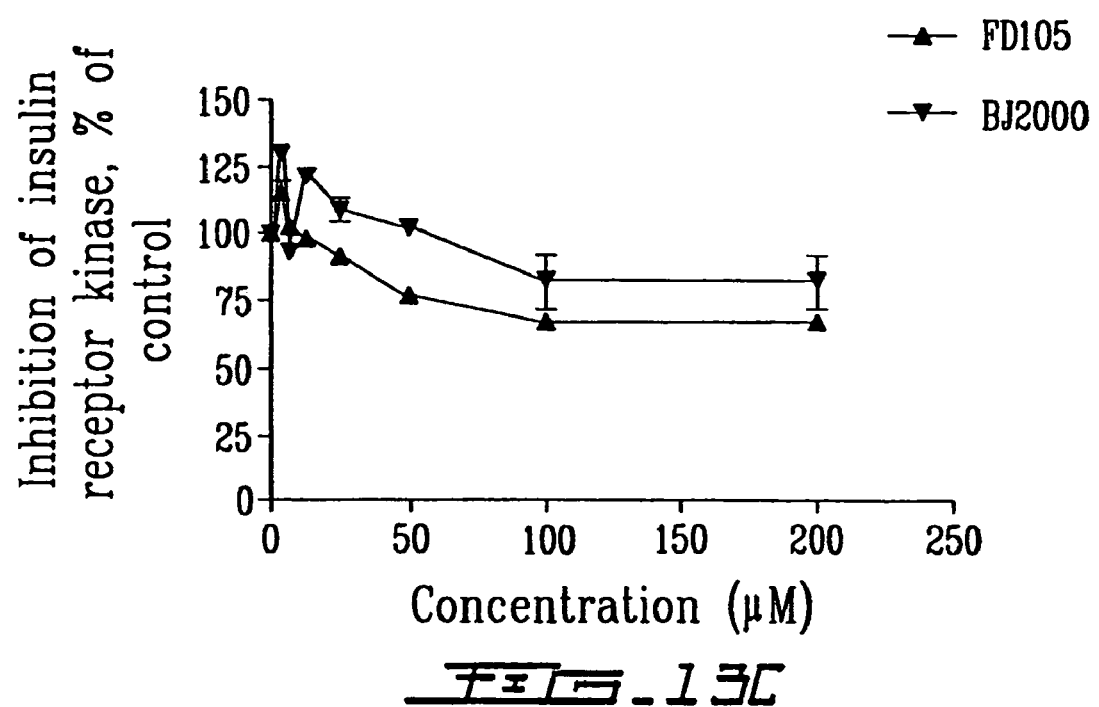
FIG. 13 shows the selectivity of BJ2000 and FD105 for EGFR TK (A); the selectivity of BJ2000 and FD105 for c-src kinase (B) and the selectivity of BJ2000 and FD105 for insulin receptor kinase (C).

In a competitive EGFR binding assay, BJ2000 ($IC_{50}$=0.1 μM) showed a 2-fold greater binding affinity than its metabolite FD105 ($IC_{50}$=0.2 μM) for the ATP site of purified EGFR. Therefore, both the drug and its corresponding pro-drugs showed significant affinity for EGFR. As previously observed, TEM did not show any effect on the tyrosine kinase activity of this receptor ($IC_{50}$>100 μM) (FIG. 13A). Further, the EGFR selectivity of these two agents was tested by comparing their EGFR inhibitory activities with those of other TKs such as c-src and the insulin receptor. In ELISA assays, BJ2000 and its metabolite FD105 did not block c-src TK activity nor did it exert any effect on insulin receptor TK in the 1-100 μM range, indicating the selectivity of these agents for EGFR (FIGS. 13B and 13C).

EXAMPLE 12

EGF-Induced Autophosphorylation Assay (SMA41 and SMA52)

The inhibition of receptor autophosphorylation in viable cells was determined by anti-phosphotyrosine Western Blots. A431 cells were pre-incubated overnight for 24 h at 37° C. in a 6-well plate (1×10$^6$) with 0.1% serum, after which they were exposed to a range of doses for each drug for 2 h and subsequently treated with 50 ng/mL EGF for 30 min at 37° C. The cells were thereafter washed with PBS and re-suspended in cold lysis buffer [50 mM Tris-HCl pH 7.5; 150 mM NaCl; 1% NP40, 1 mM EDTA; 5 mM NaF; 1 mM $Na_3VO_4$; protease inhibitor tablet (Roche Biochemicals, Laval, Canada)]. The lysates were kept on ice for 30 min and collected by centrifugation at 10 000 rpm for 20 min at 4° C. The protein concentrations were determined against a standardized control using the Bio-Rad protein assay kit (Bio-Rad Laboratories, Hercules, Calif.). Equal amounts of protein (40 μg/mL) from each lysate were added to a 12% SDS-PAGE and transferred to a PVDF membrane (Millipore, Bedford, Mass.). Non-specific binding on the PVDF membrane was minimized with a blocking buffer containing nonfat dry milk (3%) in PBS. The membrane was blotted with primary antibodies [either antiphosphotyrosine antibody (UBI, Lake Placid, N.Y.) for the detection of phosphotyrosine, or anti-EGFR (Neomarkers, Fremont, Calif.) for the determination of corresponding receptor levels], and anti-β-tubulin (Neomarkers, Fremont, Calif.) for the detection of equal loading. Thereafter, blots were incubated with HRP-goat anti-mouse antibody (1:200 dilution; Bio-Rad Laboratories, Hercules, Calif.) and the bands visualized with an enhanced chemiluminescence system (Amersham Pharmacia Biotech, Buckinghamshire, UK). Band intensities were measured using the SynGene GeneTools software package (Cambridge, UK).

EXAMPLE 13

Mixed Targeting Properties (BJ2000)

(i) Autophosphorylation Assay

The inhibition of receptor autophosphorylation in viable cells was determined by anti-phosphotyrosine Western Blots. A431 and NIH3T3 cells were grown to confluence in 6-well plates, washed twice with PBS and exposed to serum-free medium for 18 h. They were subsequently treated with the compounds for 90 min and then with EGF (100 ng/ml) for 10 min (A431 cells), or with PDGF (100 ng/ml) for 10 min (NIH3T3 cells). They were thereafter washed with PBS and re-suspended in cold lysis buffer [50 mM Tris-HCl pH 7.5; 150 mM NaCl; 1% Nonidet P-40, 1 mM EDTA; 5 mM NaF; 1 mM $Na_3VO_4$; protease inhibitor tablet (Roche Biochemicals, Laval, Canada)]. The lysates were kept on ice for 30 min and collected by centrifugation at 10,000 rpm for 20 min at 4° C. Protein concentrations were determined against a standardized control using the Bio-Rad protein assay kit (Bio-Rad Laboratories, Hercules, Calif.). Equal amounts of protein (40 μg/mL) from each cell lysate were added to an 8% SDS-polyacrylamide gel electrophoresis (SDS-PAGE) and transferred to a polyvinylidene difluoride membrane (PVDF) (Millipore, Bedford, Mass.). Non-specific binding on the membrane was minimized with a blocking buffer containing non-fat dry milk (3%) in PBS. The membrane was blotted for 1 h with primary antibodies [either antiphosphotyrosine antibody PY20 (NeoMarkers, Fremont, Calif.) or anti-EGFR antibodies (Neomarkers, Fremont, Calif.)] and anti-β-tubulin antibodies (Neomarkers, Fremont, Calif.) for the detection of equal loading. The membrane was subsequently incubated with HRP-goat anti-mouse antibody (Bio-Rad laboratories, Hercules, Calif.) and the bands visualized with an enhanced chemiluminescence system (Amersham pharmacia Biotech, Buckinghamshire, UK). Band intensities were measured using the SynGene GeneTools software package (Cambridge, UK).

For the inhibition study of mitogen-activated protein kinase (MAPK) activation by BJ2000, protein lysates were obtained as described above and a Western blot was performed (39). The membrane was incubated with anti-phosphorylated MAPK antibodies or antibodies specific for MAPK (Cell Signaling, Beverly, Mass., USA).

Figure 18:
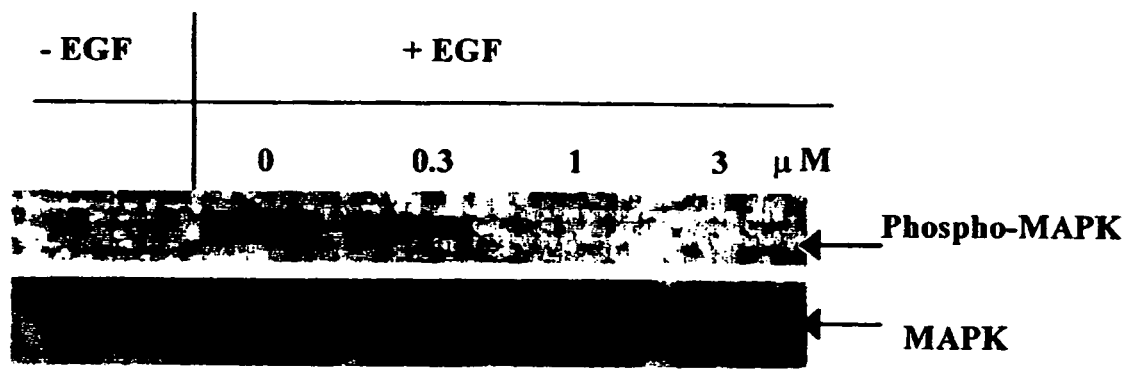

To determine whether blockade of EGFR autophosphorylation translates into inhibition of downstream signaling, the effect of the combi-molecule on EGF-induced phosphorylation of MAPK in A431 cells was analyzed. The results showed that BJ2000 induced complete inhibition of MAPK phosphorylation at concentrations as low as 1 μM without affecting the levels of MAPK, indicating that this combi-molecule may significantly block EGFR- and MAPK-dependent downstream signaling (FIG. 18).

Figure 14A:
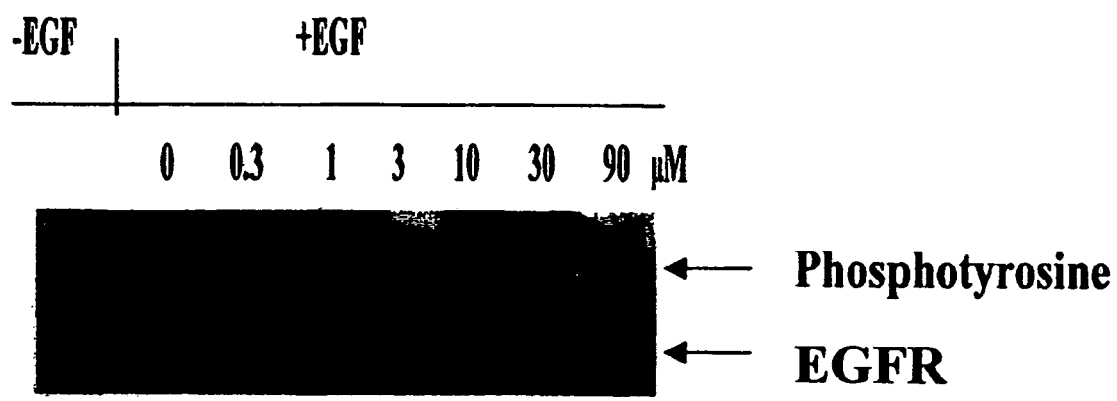
FIG. 14 shows the inhibition of EGFR and PDGFR autophosphorylation in A431 cells (A) and NIH3T3 cells (B) by BJ2000.
Figure 14B:
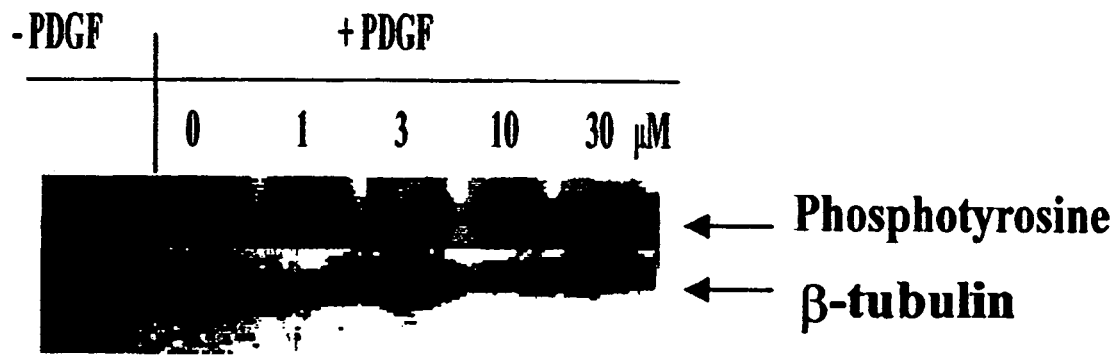
Figure 22:
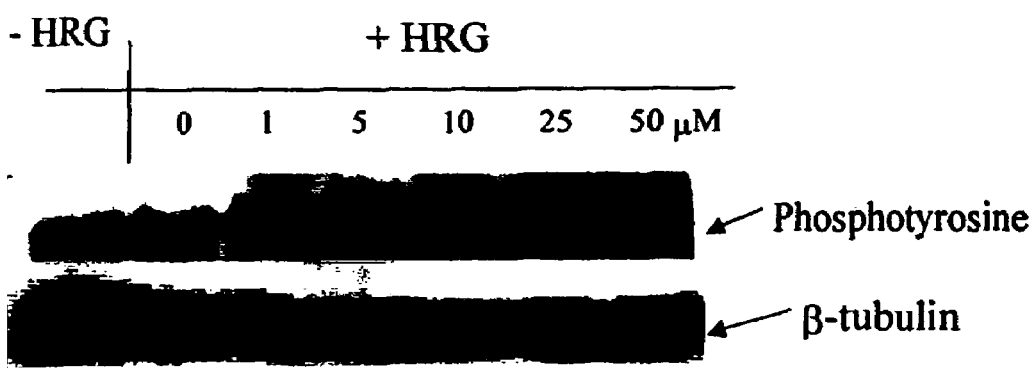
FIG. 22 illustrates the inhibition of heregulin-stimulated phosphorylation of the HER2 gene product p185$^{neu}$ by BJ2000 in the MDA-MB453 breast cancer cell line.

Western blot analysis demonstrated that BJ2000 blocked EGF-induced EGFR autophosphorylation in A431 cells, in a dose-dependent manner with an IC50≠≈6 μM, without affecting the levels of EGFR (FIG. 14A). At concentrations as high as 30 μM, it had no effect on PDGF-induced PDGFR autophosphorylation in NIH3T3 cells. These results represent further evidence of BJ2000's selectivity for EGFR (FIG. 14B). Additionally, BJ2000 is not only able to block EGF-induced EGFR TK autophosphorylation but also heregulin (HRG)-stimulated phosphorylation of the HER2 (erbB2) gene product p185$^{neu}$ (FIG. 22).

Unlike FD105, BJ2000 is a reactive molecule capable of alkylating nucleophiles. Thus, it was surmised that it might inflict some covalent damage to the ATP site of EGFR, thereby inducing irreversible inhibition. To test this hypothesis, the reversibility assay (40, 41) was used, according to which the cells are treated with the drug for 90 min after which the culture medium is repeatedly removed and replaced 3 times, followed by the measurement of EGFR autophosphorylation. As expected, BJ2000 and FD105, at 30 μM, completely suppressed EGF-dependent EGFR autophosphorylation in A431 cells immediately after drug exposure. However, at 8 h post-treatment in drug-free medium (following repeated washouts), only 40% of the EGFR autophosphorylation activity was restored in cells treated with BJ2000, indicating that the latter is capable of inducing partially irreversible inhibition of EGFR autophosphorylation. In contrast, 96% of EGFR autophosphorylation activity was restored in cells treated with FD105 at the same dose. As expected, TEM did not show any inhibitory activity immediately after the 90-min treatment, nor did it induce any effect at 8 h-post treatment (FIG. 15).

(ii) Reverse EGFR Autophosphorylation Assay

A431 cells were grown to confluence in 6-well plates and then incubated in serum-free medium for 18 h (41). Duplicate sets of cells were then treated with 30 µM of each compound for 90 min. One set of cells was then stimulated with EGF (100 ng/ml) for 10 min and extracts were made as described under the Western blotting procedure above. The other set of cells was washed free of each compound with warmed serum-free media and incubated for 2 h. Thereafter, the cells were washed, incubated for another 2 h, washed again, and then incubated for a further 4 h. This set of cells was then stimulated with EGF and extracts were prepared as for the first set.

(iii) In Vitro Growth Inhibition Assay

To study the effect of our compounds on growth factors stimulated proliferation, cells were grown to 70% confluence in 48-well plates and washed twice with PBS, after which they were exposed to serum-free medium for 18 h. The cells were then exposed to each drug and growth factors (EGF, TGFα, PDGF or serum) for 72 h and cell growth measured using the sulforhodamine B (SRB) assay (33). Briefly, following drug treatment, cells were fixed using 50 µl of cold trichloroacetic acid (50%) for 60 min at 4° C., washed five times with tap water, and stained for 30 min at room temperature with SRB (0.4%) dissolved in acetic acid (0.5%). The plates were rinsed five times with 1% acetic acid and allowed to air dry. The resulting colored residue was dissolved in 200 µl of Tris base (10 mM), and the optical density read for each well at 450 nm using a Bio-Rad microplate reader (model 2550). Each point represents the average of at least two independent experiments run in triplicate.

To study the reversibility of the antiproliferative effects of our compounds, cells were grown to 70% confluence in 96-well plates and subsequently washed twice with PBS, after which they were exposed to serum-free medium for 18 h. Under continuous exposure, the cells were exposed to different concentrations of each drug for 120 h. Under short exposure, they were exposed to each drug for 2 h, after which they were allowed to recover for 120 h in drug free medium. Growth inhibitory activities were evaluated using the SRB assay as described above.

The cytotoxic effects of our compounds were evaluated using the 3-(4,5-dimethylthiazo-2-yl)-2,5-diphenyltetrazolium bromide (MTT) assay (42) with minor modifications. Briefly, cells were grown in 24-well plates and then exposed to the compounds for 96 h. MTT (50µl) of (5 mg/ml in sterile PBS) was added to 500 µl of media and the plates were incubated for 2-3 h at 37° C. The resulting colored residue was dissolved in DMSO and the optical density read for each well at 570 nm using a Bio-Rad microplate reader (model 2550). Each point represents the average of at least two independent experiments run in duplicate.

Figure 20A:
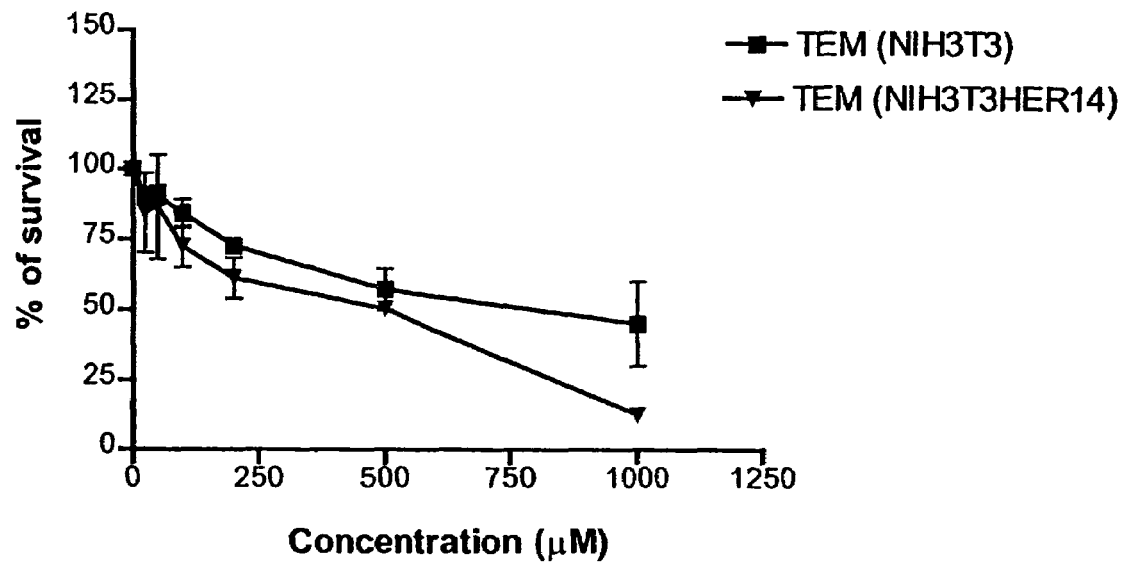
FIG. 20 illustrates the cytotoxic effect of TEM (A), BJ2000 (B) and FD105 (C) in NIH3T3 and NIH3T3HER14 cells.
Figure 20B:
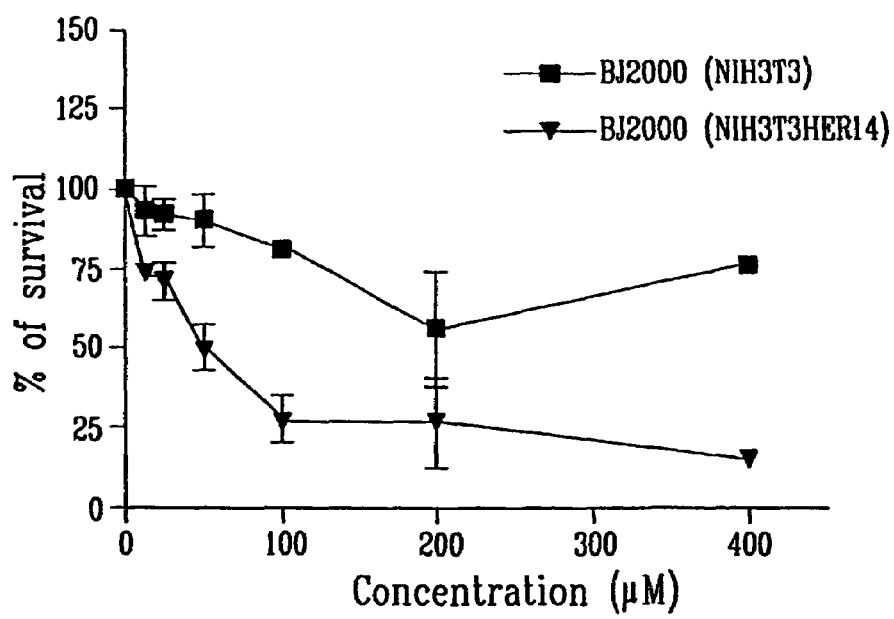
Figure 20C:
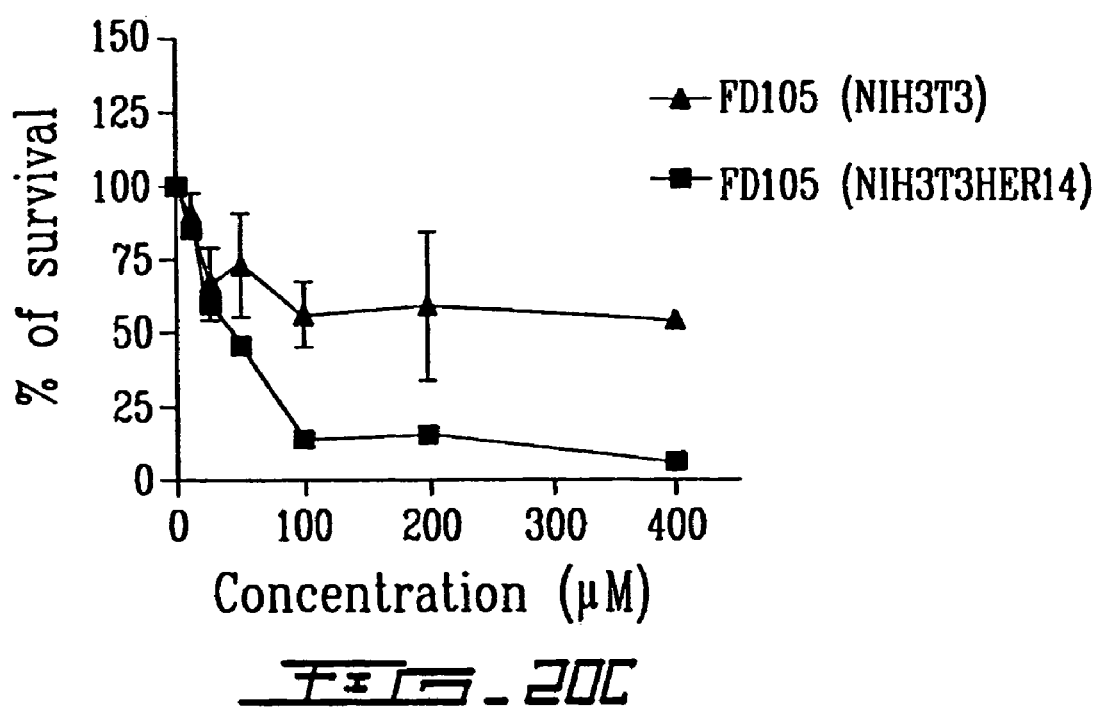

In an MTT cytotoxicity assay, TEM showed no differential cytotoxicity in the isogenic pair of cell lines NIH3T3/NIH3T3HER14 (FIG. 20A). In contrast, BJ2000 induced more than 5-fold greater cytotoxic activity in the EGFR transfectant NIH3T3HER14 (FIG. 20B). A similar differential response was also observed for its derived metabolite FD105 which was tested independently, indicating that selectivity will be maintained after complete conversion of BJ2000 to FD105 (FIG. 20C). This constitutes the first evidence of EGFR-mediated selective cytotoxicity, induced by an alkylating agent of the triazene class.

Figure 16A:
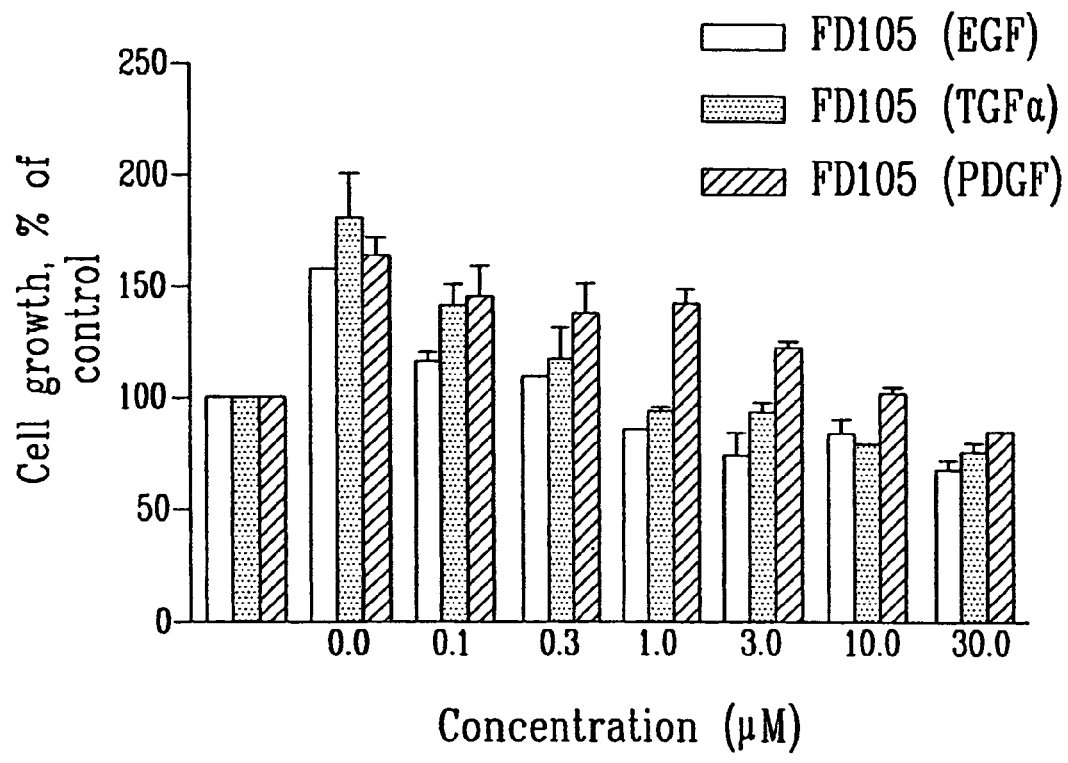
FIG. 16 shows the effect of FD105 and BJ2000 on growth factors stimulated-proliferation in NIH3T3HER14 cells: FD105+(EGF, TGFα or PDGF) (A); BJ2000+(EGF, TGFα or PDGF) (B); FD105 or BJ2000+serum (C).
Figure 16B:
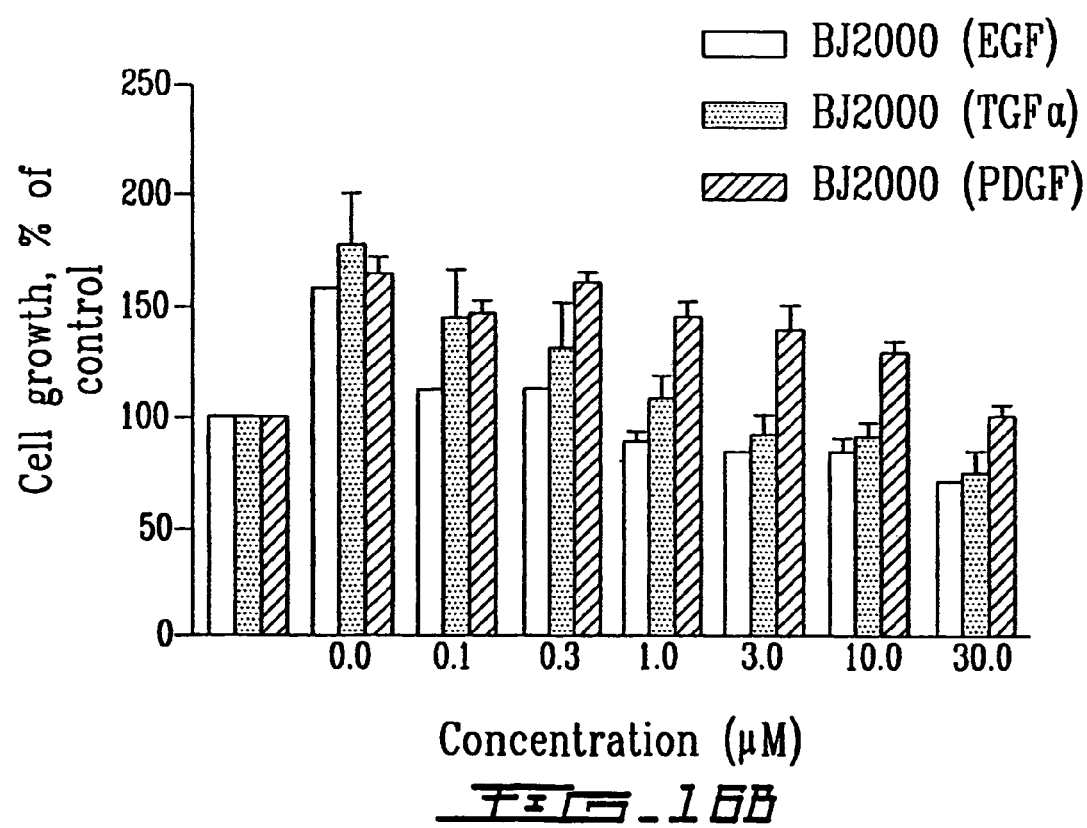
Figure 18C:
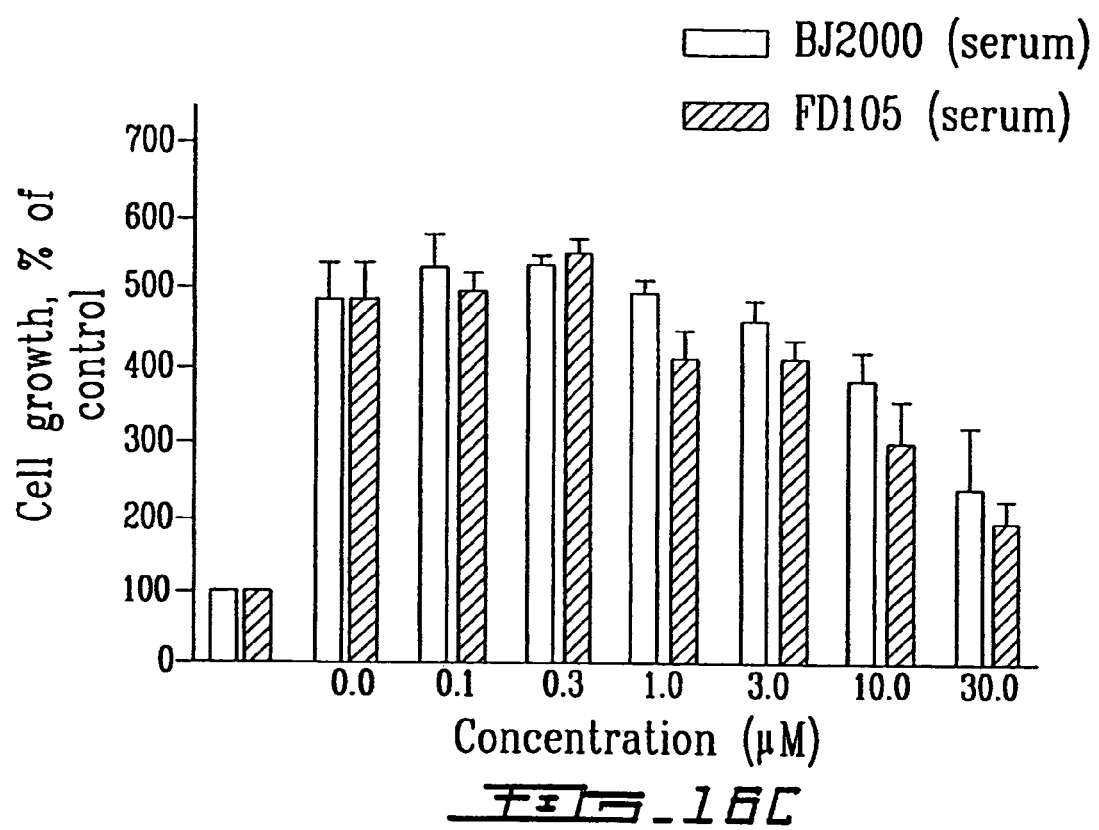
FIG. 18 is a Western blot illustrating the effect of BJ2000 on MAPK activation in A431 cells.

SRB assays demonstrated that like FD105 (FIG. 16A), BJ2000 (FIG. 16B) was capable of selectively blocking EGF or TGFα-induced proliferation in NIH3T3 cells stably transfected with the EGFR gene (NIH3T3HER14) (100% growth inhibition at 1 µM). This combi-molecule and its metabolite (BJ2000 and FD105) were approximately 30-fold less effective in inhibiting PDGF-stimulated growth (FIGS. 16A and B) (100% inhibition at around 30 µM). Similarly, these drugs exhibited a lesser effect on serum-stimulated growth in NIH3T3HER14 cells (100% growth inhibition at concentrations >30 µM) (FIG. 16C). These EGFR selective effects are in agreement with those observed from ELISA and whole cell autophosphorylation assays.

Figure 17A:
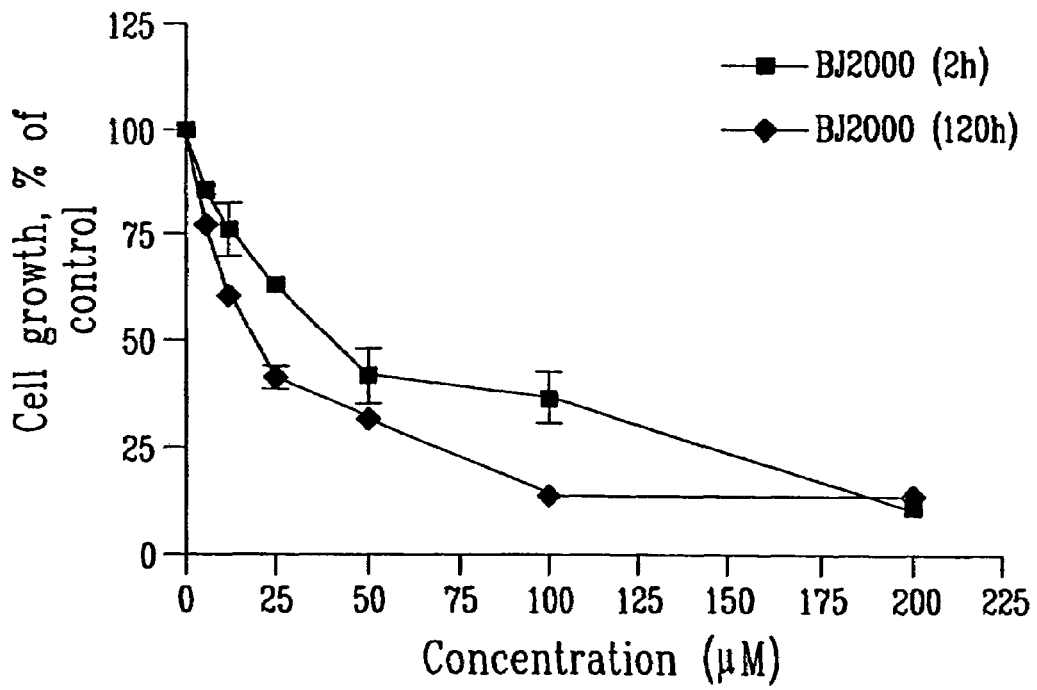
FIG. 17 shows the reversibility of the antiproloferative effect of BJ2000 (A), FD105 (B) and TEM (C) in A431 cells.
Figure 17B:
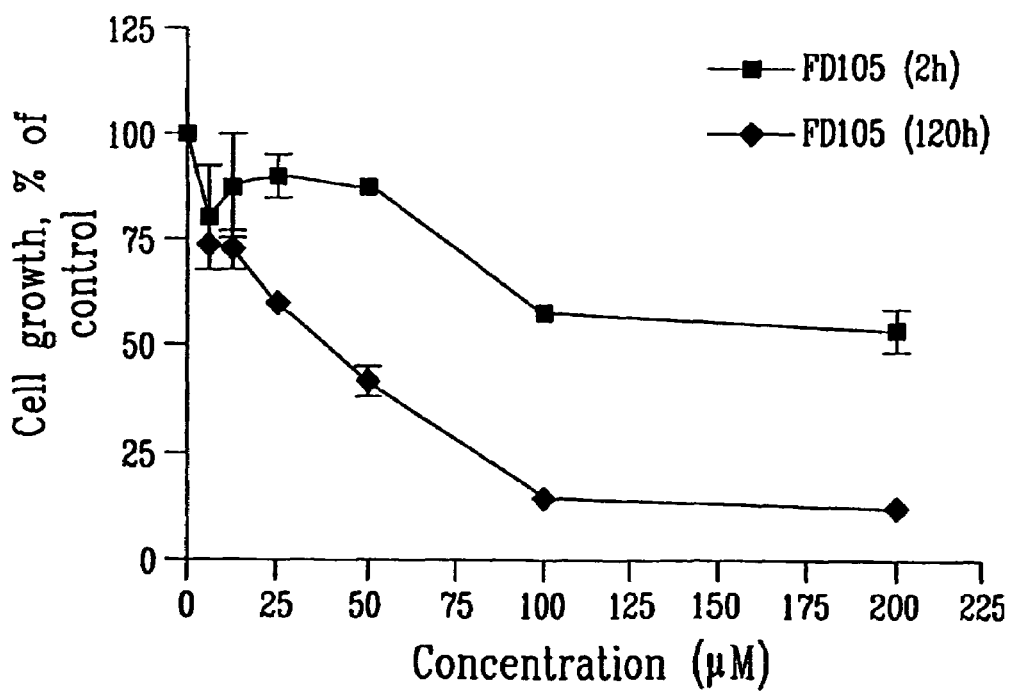
Figure 17C:
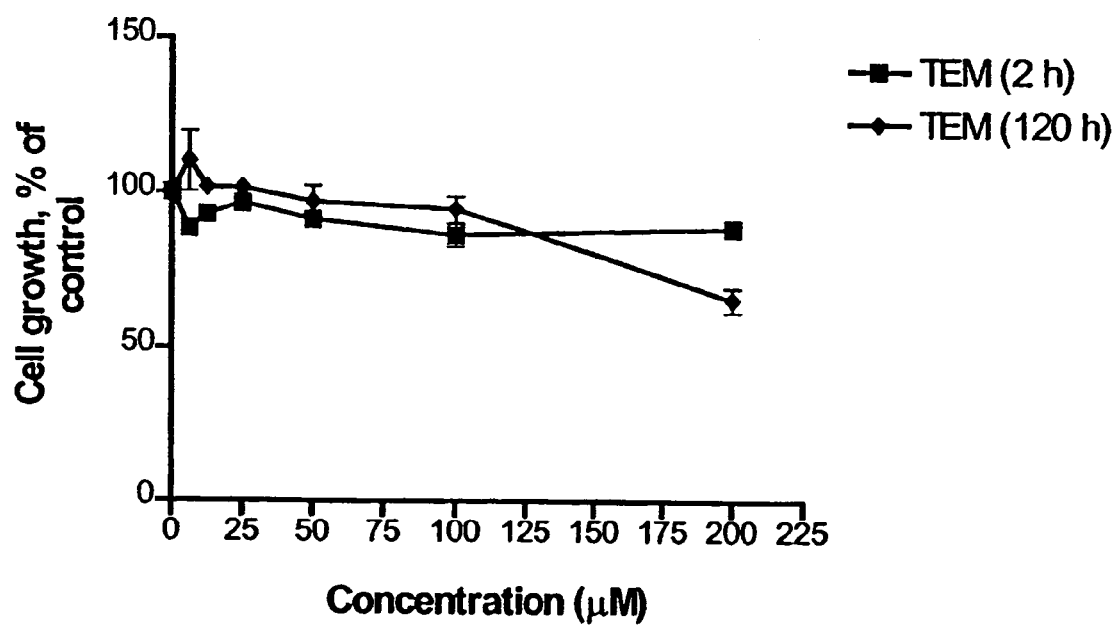

The A431 cells express TGFα and overexpress its cognate receptor EGFR, leading to an aggressive autocrine cell growth. These cells have been shown to be sensitive to antiproliferative agents targeting EGFR both in vitro or in vivo (35). Moreover, they also express the DNA repair enzyme $O^6$-alkylguanine transferase (AGT), known to be responsible for resistance to monoalkyltriazenes of the same class as BJ2000 (43). Thus, this cell line was found to be an appropriate model for testing the sustainability of the antiproliferative effects of the compounds of the present invention. After 120 h of continuous exposure, the results obtained from the SRB assay (FIG. 17A) showed that BJ2000 was≈3-fold more potent ($IC_{50}$=15 µM) than its metabolite FD105 alone ($IC_{50}$=47 µM) (FIG. 17B) in the AGT-proficient cell line A431. In contrast, TEM at concentrations as high as 200 µM, did not show any significant antiproliferative activity in these cells (FIG. 17C). More importantly, in a short exposure assay (2 h) followed by a 120 h recovery period, an almost complete loss of activity was observed for FD105 in the A431 cell line, ($IC_{50}$>100 µM) (FIG. 17B), indicating that it induced significant reversible growth inhibitory activity. In contrast, BJ2000 showed significant retention of activity ($IC_{50}$=38 µM) (FIG. 17A), indicating a more sustained effect as compared to its metabolite FD105.

(iv) Alkaline Comet Assay for Quantitation of DNA Damage

The alkaline comet assay was performed as previously described (26). The cells were exposed to the drugs (BJ2000, FD105 or TEM) for 30 min, harvested with trypsin-EDTA, and subsequently collected by centrifugation and resuspended in PBS. Cell suspensions were diluted to approximately $10^6$ cells, and mixed with agarose (1%) in PBS at 37° C. in a 1:10 dilution. The gels were cast on Gelbond strips (Mandel Scientific, Guelph, Canada) using gel casting chambers, as previously described (31), and then immediately placed in a lysis buffer [2.5 M NaCl, 0.1 M tetra-sodium EDTA, 10 mM Tris-base, 1% (w/v) N-lauryl sarcosine, 10% (v/v) DMSO, and 1% (v/v) Triton X-100, pH 10.0]. After being kept on ice for 30 min, the gels were gently rinsed with distilled water and immersed in a second lysis buffer (2.5 M NaCl, 0.1 M tetrasodium EDTA, 10 mM Tris-base) containing 1 mg/ml proteinase K for 60 min at 37° C. Thereafter, the gels were rinsed with distilled water, incubated in alkaline electrophoresis buffer for 30 min at 37° C., and electrophoresed at 300 mA for 60 min. The gels were subsequently rinsed with distilled water and placed in 1 M ammonium acetate for 30 min. They were soaked in 100% ethanol for 2 h, dried overnight, and subsequently stained with SYBR Gold (1/10000 dilution of stock supplied from Molecular Probes, Eugene, Oreg.) for 20 min. Comets were visualized at 330× magnification and DNA damage was quantitated using the Tail Moment parameter (i.e., the distance between the barycenter of the head and the tail of the comet multiplied by the percentage of DNA within the tail of the comet). A minimum of 50 cell comets were analyzed for each sample, using ALKO-MET version 3.1 image analysis software, and values are averages of tail moments for the entire cell population per sample.

Figure 19A:
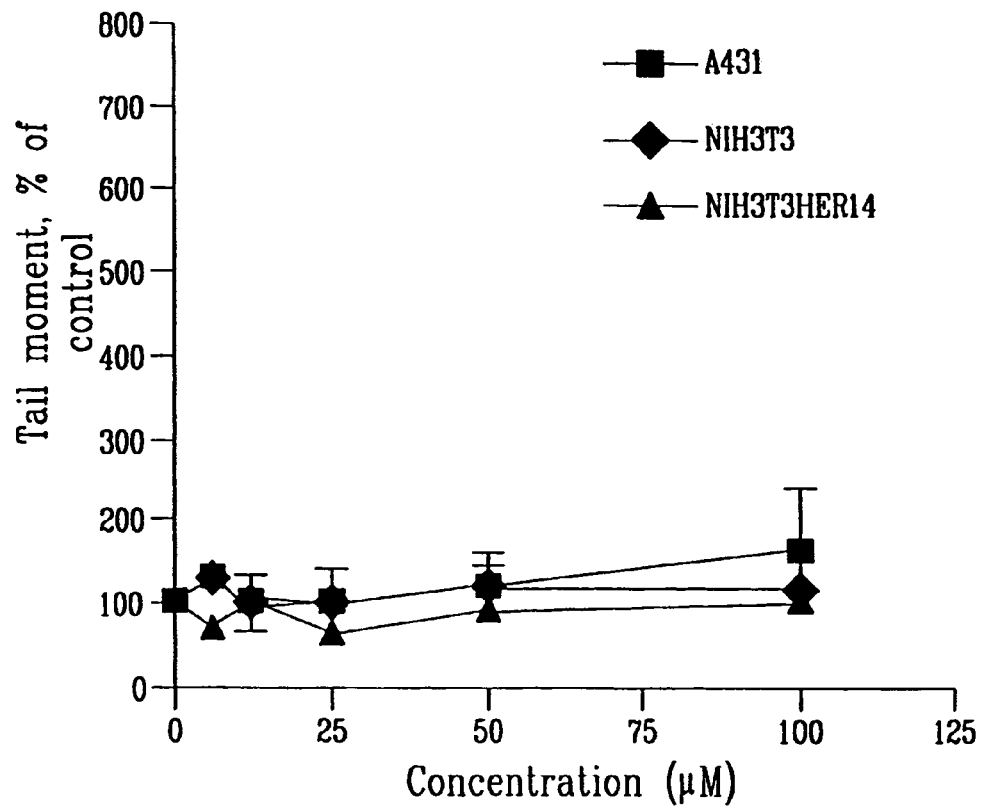
FIG. 19 illustrates a graphic quantitation of DNA damage using the alkaline comet assay. DNA damage was detected in A431, NIH3T3 and NIH3T3HER14 cells exposed to FD105 (A) and BJ2000 (B) for 30 min.
Figure 19B:
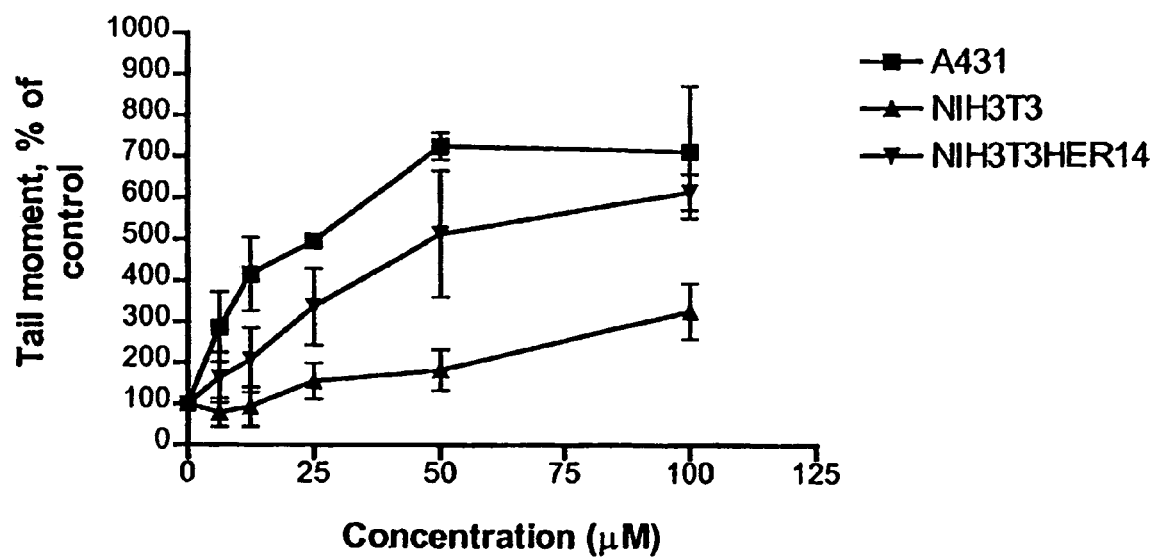

Using the alkaline comet assay, it was demonstrated that, in contrast to FD105 (FIG. 19A) and like TEM, BJ2000 induced dose-dependent DNA damage in A431 cells after.30 min to drug exposure (FIG. 19B), which constitutes indirect evidence of the formation of a metastable methyldiazonium species. Interestingly, when the assay was performed in an isogenic pair of cell lines, wherein the sole difference was the EGFR, BJ2000 induced more than 2-fold higher levels of DNA damage in the EGFR transfectant, suggesting that EGFR affinity (as predicted by path 3 in Scheme 2, EGFR+) may play a role in targeting the drug to EGFR-expressing cells (FIG. 19B).

EXAMPLE 14

Binary Targeting Properties of SMA41

The significant antiproliferative activity of SMA41 in a methyltriazene-resistant cell resulted in further studies of its binary (EGFR and DNA) targeting properties. This was achieved by two types of assays: EGF-stimulated tyrosine phosphorylation and DNA damage.

i) Inhibition of EGFR TK Activity

Figure 9:
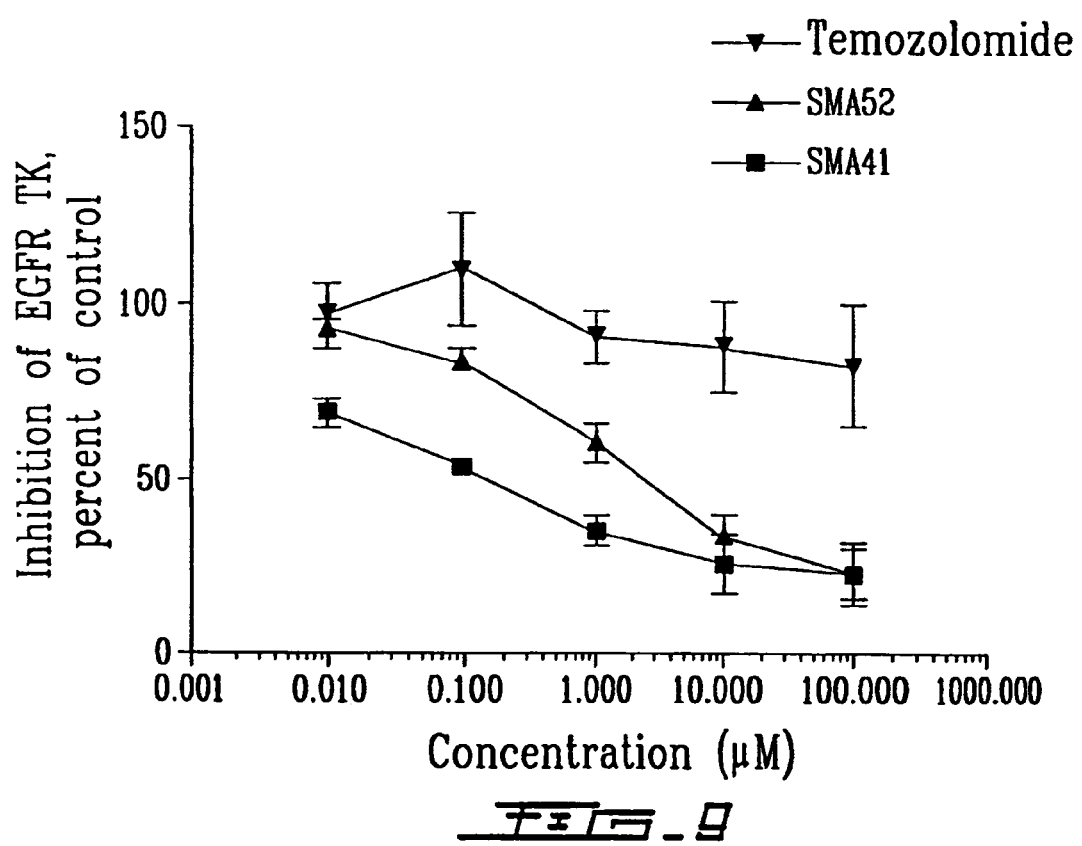
FIG. 9 shows a comparison of the EGFR TK inhibitory activities of SMA41, SMA52, and TEM in an ELISA using PGT as a substrate.

In a competitive EGFR binding assay, SMA41 ($IC_{50}$, 0.2 µM) showed a 5-fold stronger binding affinity than SMA52 (1.02 µM) for the ATP site of the purified receptor. TEM did not show any significant affinity for this receptor ($IC_{50}$>100 µM) (FIG. 9). This is an example of a conjugate CYT-I (e.g. SMA41) that has stronger affinity for its cognate receptor than its metabolite I (e.g. SMA52) (see Scheme 2).

Figure 10:
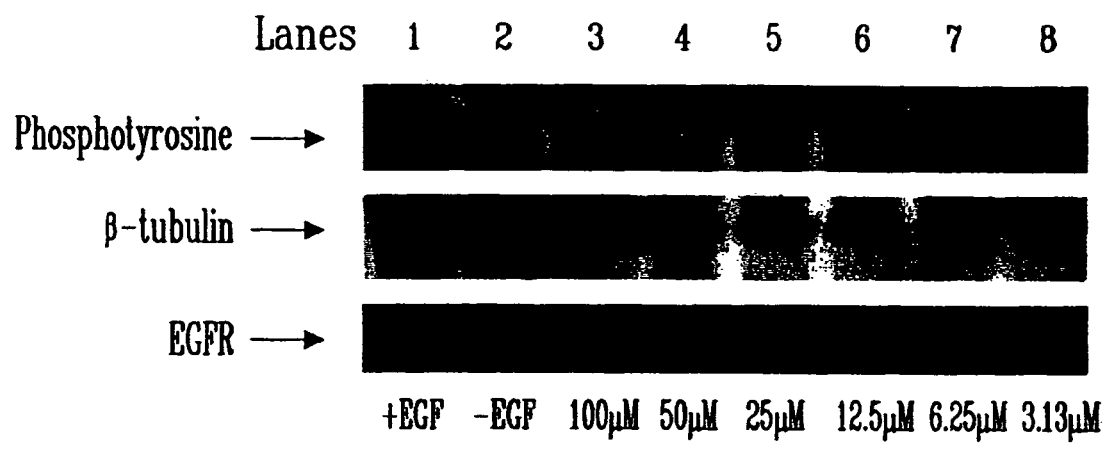
FIG. 10 shows a western blot showing the ability of SMA41 to block EGF-stimulated EGFR autophosphorylation in the A431 cell line.

Western blot analysis (FIG. 10) demonstrated that both drugs induced almost equal levels of inhibition of EGF-induced EGFR autophosphorylation [$IC_{50}$ SMA52=8.44 µM, $IC_{50}$ SMA41 12.5 µM]. In contrast to SMA41 and SMA52, TEM did not exhibit any EGFR binding affinity, nor did it inhibit EGF-induced autophoshorylation in A431 cells [$IC_{50}$>100 µM] in the specified dose ranges.

ii) Quantitation of DNA Damage

Figure 11A:
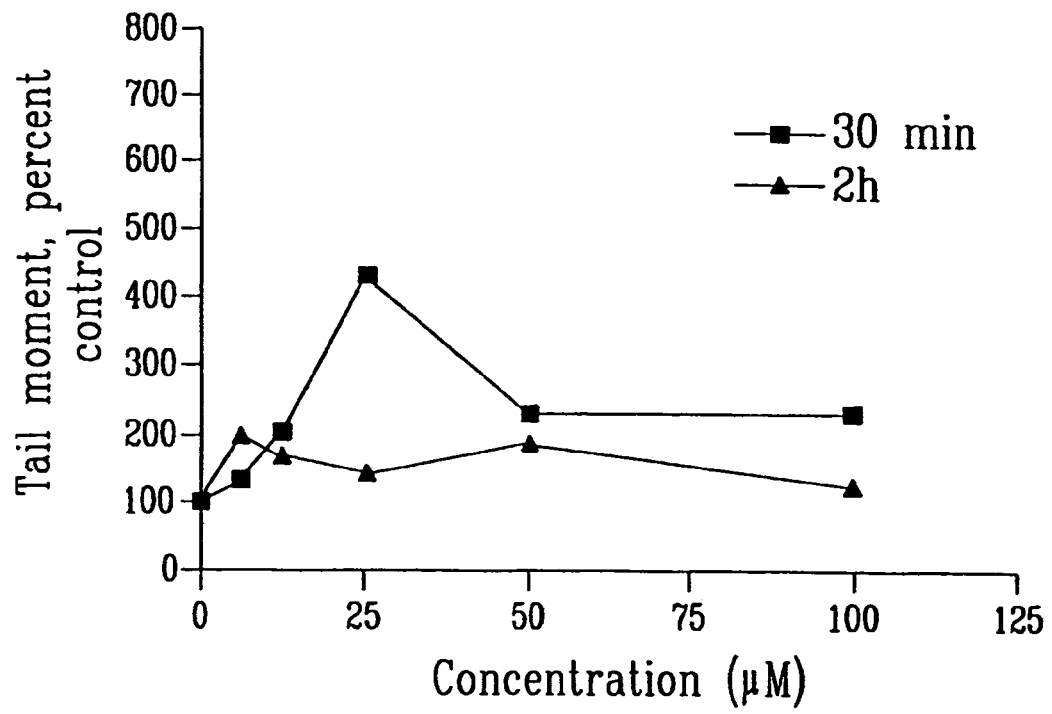
FIG. 11 shows a comparison of DNA damage induced by SMA41 (FIG. 11a), TEM (FIG. 11b) and SMA52 (FIG. 11c) after a 30-min and a 2 h-drug exposure using the alkaline comet assay.
Figure 11B:
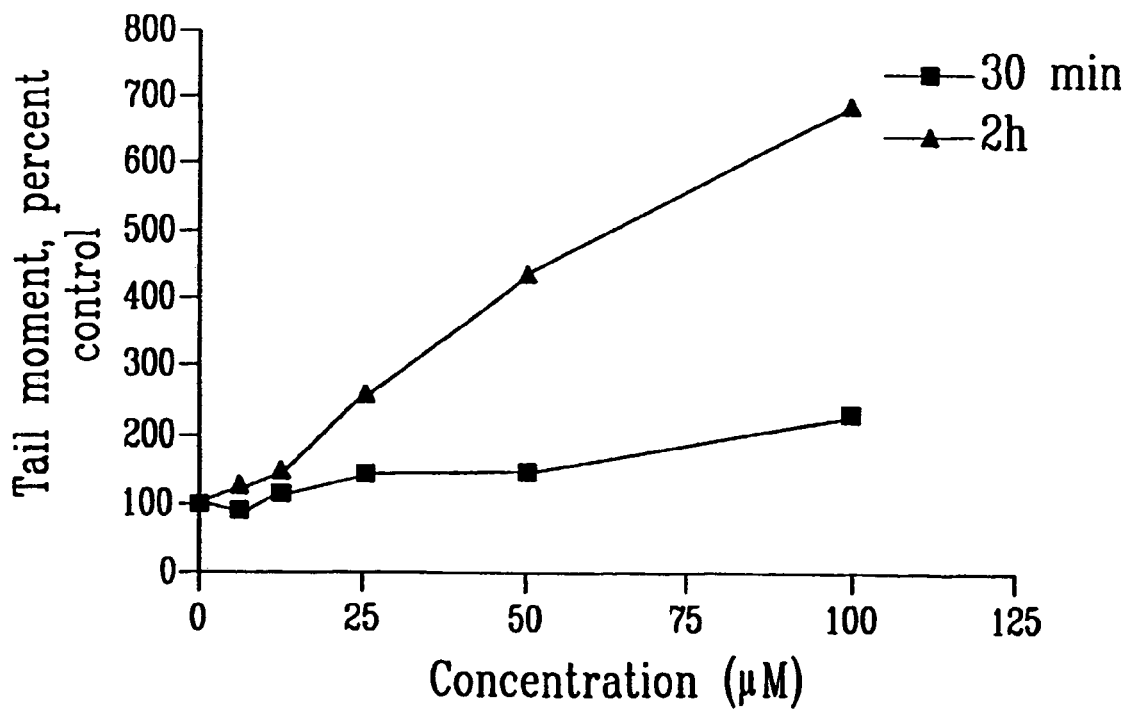
Figure 11C:
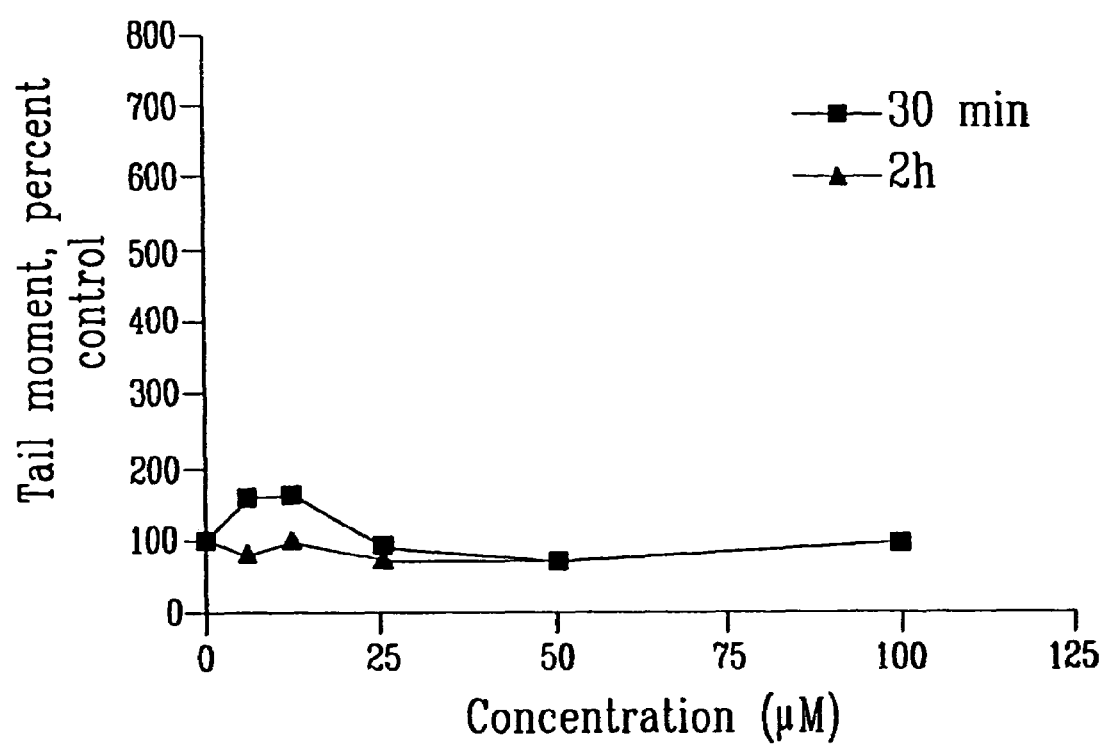

Using the alkaline comet assay, it was demonstrated that in contrast to SMA52 (FIG. 11), both SMA41 and TEM were capable of inducing DNA damage in a dose-dependent manner. However, differences were observed in the kinetics of dose-dependent DNA damage induced by SMA41 when compared with TEM. For SMA41, the trend was to induce rapid nuclear condensation at the highest doses (25-100 µM) leading to a reduction in comet tailing. For SMA41, a significant comet tail moment could only be observed in the 6-25 µM range after a short 30 min and 2 h drug exposure (FIG. 11). With a 2 h exposure, a decrease in tail moment was observed at concentrations above 6 µM, concurrent with observable nuclear condensation, likely due to a rapid onset of apoptosis. In contrast, TEM (FIG. 11) exhibited a dose-dependent increase in comet tail moment under 30 min exposure with a remarkable enhancement under the longer 2 h drug exposure (FIG. 11). This is prima facie evidence that despite the fact that they are both being methylating agents, the mechanism of action of SMA41 would appear to be markedly different from that of TEM.

Discussion

Agents targeting EGFR and its closest homologue p185$^{neu}$, the HER2 gene product, present two major advantages: 1) they induce target-selective antitumor activities, and 2) they exhibit good toxicity profiles. However, where they cannot induce apoptosis, they are cytostatic agents that induce reversible antitumor effects. For sustained antitumor activity, combinations with other cytotoxic drugs (e.g. cisplatin, doxorobucin, taxans) have proven a useful alternative (13). The lack of selectivity of the latter agents however, may negatively alter the overall toxicity profiles of these regimens. A novel approach to this problem is proposed that seeks to combine EGFR TK inhibitors with pharmacophores having known cytotoxic DNA damaging properties into single combi-molecules targeted to EGFR.

As outlined in Scheme 3, the target-mediated selectivity component of our approach is based on the strong affinity of the combi-molecule for the cytosolic domain of EGFR, which may influence the equilibria TZ-I' (extracellular compartment)/TZ-I (cytosolic) (path 1) and TZ-I (cytosolic)/TZ-I-EGFR (path 3). Both bound and unbound fractions of TZ-I will eventually degrade to generate I which may further block EGFR TK (paths 5 and 7). Fractions of unbound TZ-I may diffuse through the nucleus where the generated methyldiazonium species (TZ) may alkylate and damage DNA (path 6). Additionally, TZ-I may react with amino acid residues of the active site of the receptor, thereby irreversibly inhibiting it, leading to the formation of I-TZ-EGFR which may liberate I. If the in situ generated I loses affinity for the damaged receptor, it may bind to other non-damaged receptor molecules, leading then to a more sustained EGFR TK inhibition (path 4). More importantly, TZ-I may undergo hydrolysis resulting in the in-situ release of unreacted fractions of TZ which may diffuse away from the receptor. These postulates were supported by prima facie experimental data obtained with BJ2000.

Overexpression of EGFR is common in a wide variety of major human solid tumors of epithelial origin such as breast, colorectal, head and neck ovarian and bladder carcinomas (44). EGF binding induces receptor dimerization, autophosphorylation and activation of mitogenic signaling. The A431 cell line expresses a large number of EGF binding sites and also the high affinity EGFR ligand TGF (35). This translates into aggressive autocrine-controlled growth in vitro. Blocking A431 cell proliferation has become the standard screen for anti-proliferative inhibitors of EGFR TK activity (35, 45). This cell line also expresses the alkyltriazene resistance-associated DNA repair enzyme MGMT and is, as demonstrated herein (FIG. 5b), resistant to cyclic 1-methyl-1,2,3-triazene TEM ($IC_{50}$=366 µM). Therefore, it represents a good model for the determination of the pharmacological advantages of the simultaneous targeting of EGFR and DNA in EGF expressing refractory tumors.

Dacarbazine and TEM, two prodrugs of monomethyltriazenes, are the most active drugs in the treatment of malignant melanomas and gliomas (46). As outlined in Scheme 1, cytotoxic monoalkyltriazene MTIC degrades under physiological conditions to generate a variety of metabolites, the critical reaction being the heterolysis of the non conjugated tautomer to generate the arylamine AIC and the alkyldiazonium species (47). It has already been shown by isotopic labeling that the latter species alkylates DNA at the 6- and 7-positions of guanine or the 3-position of adenine. As demonstrated, SMA41 is able to generate, as does MTIC, a free arylamine (SMA52), and a concomitantly generated metastable methyldiazonium capable of inducing the same type of alkali labile DNA lesions as those associated with TEM or other classical triazenes. Indeed, in contrast to SMA52-exposed cells, significant levels of DNA damage were observed in those treated with SMA41 in the 6.25-25 µM range. Since this assay involved alkaline electrophoresis of the whole cell nuclei, it is believed that this fragmentation is primarily due to N7-methylguanine, a type of lesion with known alkali labile properties (48). The quantitation of this type of alkali labile DNA lesion by the classical alkaline elution assay is now well documented (49).

Single-cell microelectrophoresis (comet) assays clearly showed that, like TEM the clinical prodrug of MTIC, SMA41 possesses strong DNA damaging properties. However, the marked differences between dose-response profiles of SMA41 and TEM [DNA damage, SRB and clonogenic assays] indicate that these two methylating agents may block cell proliferation by a different mechanism. It is noteworthy that the activity of SMA41 was. approximately 8-fold greater in the clonogenic assay than in the SRB assay. This can be attributed to an increased exposure time (6-day continuous exposure).

The second target of SMA41 was first elucidated by measuring its ability to block EGFR TK phosphorylation of a PGT substrate in an ELISA assay. It should be first remembered that the design of SMA41 was primarily based upon previously identified structure activity-relationships in the quinazoline series, showing that bulky substituents are tolerated at the 6- and 7-positions. In addition, electron-donating substituents increase their binding affinity for the ATP-binding site of EGFR. Since the delocalization of electrons from the N3 of the triazene chain may confer only a slight electron-donating character to SMA41, we believe that its stronger EGFR TK inhibitory activity when compared with SMA52 (which contains a stronger electron-donating group at the 6-position (Hammett constant $\sigma_p=-0.57$, $\sigma_m=-0.09$) (50) may be due to its ability to induce methylation of nucleophilic amino acid side chains in the ATP binding site of the receptor (e.g. thiol function of a cysteine residue). It has recently been demonstrated that quinazolines bearing an acrylamide group at the 6-position are capable of alkylating cysteine 773 at the TK active site (5, 51), and that the 6-position is 4 Angstroms closer to this cysteine residue than the 7-position. The non-conjugated form of the alkyltriazene moiety, which has approximately the same length as the acrylamide moiety, and is a strong alkylator, may undergo a similar type of alkylation in the active site of EGFR. Moreover, since an exposure time (8 min) shorter than the $t_{1/2}$ was used in the ex vivo tyrosine kinase assay (FIG. 1, FIG. 9), the observed inhibitory activity would appear to be mainly due to the binding of the intact molecule with minimal contribution of the residual SMA52 metabolite.

Having demonstrated that SMA41 is able to target isolated receptors, an investigation of whether this agent could block signal transduction in A431 cells was carried out. An EGF-induced total phosphorylation assay showed that like SMA52, SMA41 is capable of inhibiting EGF-induced total TK phosphorylation in a dose-dependent manner in A431 cells. In addition, SMA41 is capable of blocking EGF-induced autophosphorylation of EGFR. It is important to mention that no detectable levels of tyrosine kinase inhibitory activity were observed with TEM over its whole dose range. The detection of autophosphorylation inhibitory activities for SMA41 and SMA52 is indirect evidence of normal transport of these compounds across the cell membrane, although it is not clear at this stage whether SMA41 is sequestered in the cells before its hydrolytic cleavage to SMA52 or whether significant extracellular cleavage occurs prior to cell penetration of these two species. However, some inference can be made in light of the macromolecular targeting results.

In contrast to the isolated enzyme assay, which showed a 5-fold superior inhibitory activity for SMA41 when compared to SMA52, the whole cell phosphorylation assays exhibited similar levels of activity for these two drugs. If no DNA damage was observed, these results could indicate a total extracellular conversion of SMA41 to SMA52 prior to cell penetration. However, the significant nuclear fragmentation and the marked retention of activity observed when SMA41 was removed after 2 h (FIG. 6a), are indirect evidence of intracellular sequestration of SMA41 since, as was demonstrated, SMA52 alone does not possess DNA damaging properties (FIG. 11). The loss of TK inhibitory activity of SMA41 when compared to SMA52 (from the isolated enzyme to the whole cell assays) may be due to differences in the intracellular distributions of these drugs. Nevertheless, the results in toto give prima facie evidence that SMA41 is a novel triazene with a significant EGFR tyrosine kinase inhibitory activity, a property that has never been observed before for any class of mono- or dialkyltriazenes.

Based upon known principles of medical oncology which suggest that rapidly proliferating cells are more sensitive to DNA damaging agents than slow-growing ones, it was feared that the cytostatic effect of EGFR TK inhibition would initially block proliferation and thereby decrease cell sensitivity to the DNA damage associated with the concomitantly generated methyldiazonium species. This would translate into a rather antagonistic effect. To test this hypothesis, the combined effect of the two mechanisms of action were mimicked by designing a 2-drug combination model involving SMA52 (an EGFR TK inhibitor) and TEM (a DNA damaging agent). The results showed a sub-additive interaction and not an antagonistic one between these two drugs. Moreover, it is noteworthy that SMA41 was more potent than the 2-drug combination. This suggests that a single molecule formulated as a masked form of these two types of agents may be more efficacious than a 2-drug combination encompassing individual monoalkyltriazenes and EGFR TK inhibitors.

Since SMA41 can both block phosphorylation induced by EGF and damage genomic DNA, its over 8-fold (SRB assay) and over 90-fold (clonogenic assay) greater potency when compared with TEM may result from the combined effects of these two distinct mechanisms of antiproliferative activities. The binary targeting may trigger signal transduction associated with the induction of apoptosis. Indeed, in contrast to SMA52 and TEM, significant nuclear condensation was observed in cells treated with SMA41 for 2 h in the 25-100 µM range.

A significant body of evidence suggests that overexpression of EGFR is a marker for poor prognosis in many solid tumors. Selective inhibitors of tyrosine phosphorylation by EGFR are now considered an important class of anticancer drugs and two members of the 4-(phenylamino)quinazoline class are now in clinical trial. Despite the significant EGFR inhibitory activity of these reversible inhibitors, the high intracellular concentrations of ATP is a major barrier to sustained inhibition of EGF-stimulated signal transduction in tumor cells. This problem was more recently addressed (5) and it was illustrated that quinazolines containing an acryloyl function at the 6-position could induce irreversible inhibition of EGFR by alkylating cysteine 773 of the enzyme. A recently synthesized water-soluble analogue of this class has now been selected for Phase I clinical trial (51). It is noteworthy that despite being an irreversible inhibitor of EGFR when apoptosis is not triggered, if the cells respond to alternative growth hormones (e.g. heregulin or PDGF) these compounds may still not induce a sustained growth inhibitory activity.

The novel SMA41 molecule of the present invention presents the advantage of being not only capable of blocking EGF-stimulated signal transduction on its own but also of generating a DNA alkylating species that may inflict irreversible cytotoxic DNA lesions. Moreover, this compound was designed to release another intact EGFR TK inhibitory molecule (e.g. SMA52) that may further enhance its growth inhibitory activity. The results illustrate that these combined properties confer increased potency to a monoalkyltriazene against an MGMT-proficient tumor cell line with marked resistance to the clinical drug TEM (IC50, 366 μM).

The current study which was primarily designed to identify the principal targets of SMA41, has conclusively demonstrated that this one-molecule combination showed superior activity when compared to a 2-drug combination involving TEM+SMA52. Based on these results, an additional combi-molecule (BJ2000) was designed and which also possesses two major components: an EGFR inhibitory component imprinted into the quinazoline moiety and a DNA damaging methyldiazonium species masked by the appended 3-methyl-1,2,3-triazene moiety. The effects of the EGFR component were demonstrated both by enzyme and by whole cell assays, whereby the ability of the combi-molecule to block substrate (ELISA) and EGFR autophosphorylation (Western blotting) was clearly shown. Furthermore, BJ2000 was shown to exhibited selectivity for EGFR in both ELISA and growth factor-stimulated proliferation assays. The most significant proof of direct interaction with EGFR was however obtained from the reversibility assay which showed only a 40% recovery of the autophosphorylation activity, eight hours after cell exposure, despite multiple washouts. In contrast, almost complete recovery of initial EGFR autophosphorylation activity was observed in cells treated with FD105 at the same dose (FIG. 15). It is presently not clear whether the partial inactivation of the EGFR TK occurred through alkylation of amino acid residues located in the active site. It was nevertheless demonstrated (40, 41) that acryloyl moieties attached to the 6-position of quinazoline, react with cysteine 773 of EGFR, leaving an irreversibly inhibited receptor.

Additional combi-molecules of the triazene class such as D and E, were designed and tested for their inhibition of EGFR tyrosine kinase activity. The inhibition of EGFR tyrosine kinase activity by compound C, which is the inhibitor moiety (I) of a combi-molecule "I-TZ" is also provided.

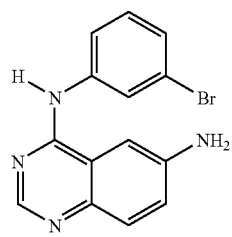

C

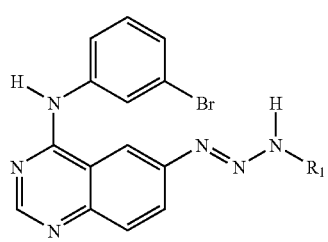

D

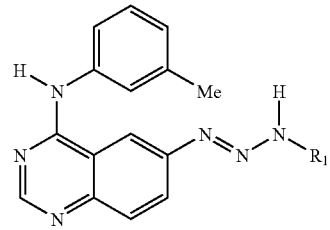

E

Table 1 shows the $IC_{50}$ values for the combi-molecules depicted by Formula D, E, the $IC_{50}$ values for compound C as well as those obtained for SMA41 and BJ2000 for comparison. The observed $IC_{50}$ results are indicative of very high binding affinity for the EGFR tyrosine kinase receptor and of the potential of this class of compounds, more specifically combi-molecules of the triazene class, in the treatment of diseases involving EGFR and family members such as the HER2, HER3 and HER4 gene products.

TABLE 1

Inhibition of EGFR tyrosine kinase activity by high affinity combimolecules

| Compounds | $R_1$ | $IC_{50}$ (μM) |
|---|---|---|
| C | — | 0.044 ± 0.013 |
| D | Me | 0.039 ± 0.0035 |
| D | $MeOCH_2CH_2$— | 0.071 ± 0.029 |
| D | —CH₂CH₂—N(morpholine) | 0.064 ± 0.0094 |
| D | 2-methylpyridyl | 0.238 ± 0.069 |
| E | $MeOCH_2CH_2$— | 0.196 ± 0.031 |
| SMA41 | | 0.200 |
| BJ2000 | | 0.100 |

Note:
Data are means and SE's of two separate experiments.

The triazene chain of the present C-(BJ2000) being appended to the same position and possessing approximately the same length as the acryloyl moiety, is likely to undergo a similar type of interaction. As depicted in Scheme 7, the non-conjugated tautomer of BJ2000 may be attacked by the cysteine 773 in an orientation similar to that reported by Smaill (40). The delayed recovery of autophosphorylation may therefore support path 4 (Scheme 3) which postulates a possible covalent inactivation of the receptor (see TZ-EGFR in Schemes 3 and 7).

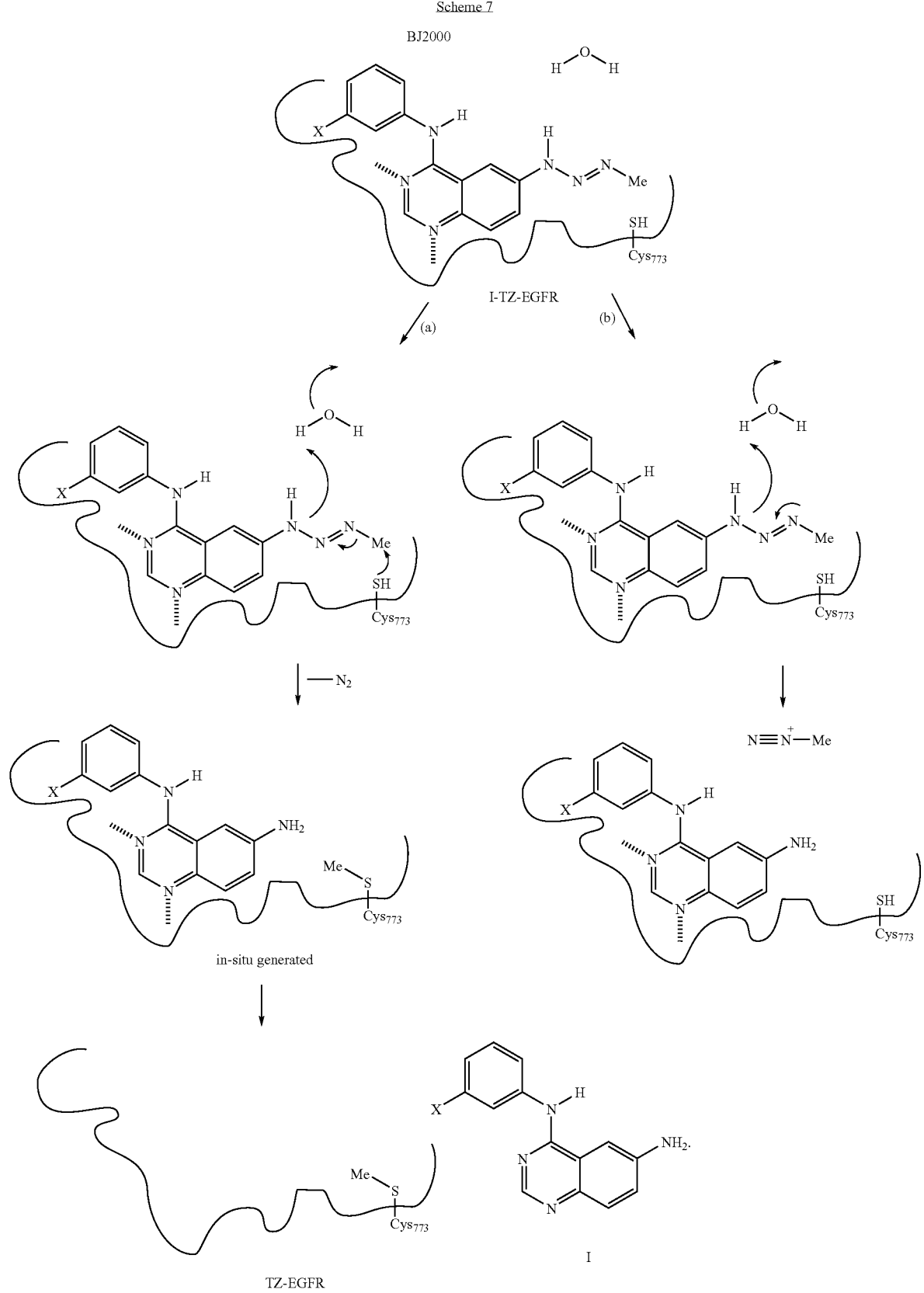

The DNA damaging properties of BJ2000 were compared with the clinical drug TEM. Like TEM, BJ2000 induced significant DNA damage in A431 cells after a 30-min drug exposure (FIG. 19B). This constitutes indirect confirmation of the generation of the DNA damaging methyldiazonium species (TZ), as postulated by path 6 (Scheme 2). Complete confirmation of the latter path (path 6), predicting the hydrolytic conversion of TZ-I into TZ+I, was provided by HPLC detection of I (FD105) and by kinetic analysis. The results clearly illustrate an inverse relationship between the degradation of BJ2000 ($t_{1/2}$=75 min) and the formation of FD105 in 87% yield, after complete degradation (4-24 h, FIG. 12B). Thus far, the results in toto lend support to almost all the postulates depicted in Scheme 3 (paths 1-7). According to Scheme 3 a TZ-I (or combi-molecule) can bind to EGFR (paths 1 and 3) or degrade to another high affinity inhibitor I (paths 2 and 5) and a reactive species that can damage DNA (path 6), or perhaps the receptor. Additionally, the combi-molecule TZ-I may directly alkylate the active site of EGFR, through the attack on the triazene moiety by cysteine 773, generating an inactivated covalently modified, irreversibly inhibited receptor I-TZ-EGFR (path 4). If I loses affinity for the damaged receptor, it is surmised to be released, whereupon it can bind to another undamaged EGFR ATP binding site providing I-EGFR (path 7). Additionally, TZ-I may undergo hydrolysis resulting in the in situ release of unreacted fractions of TZ which may diffuse away from the receptor.

On the other hand, it is predicted in Scheme 3 that EGFR-deficient cells (see EGFR⁻), due to the absence of a target, will not be growth-inhibited by TZ-I nor by the generated I. In addition, in contrast to the EGFR-proficient cells (EGFR⁺), it is postulated that EGFR⁻ cells will display inflicted DNA lesions, the antiproliferative effects of which will not be potentiated by inhibition of EGFR-mediated signaling. They are therefore expected to be less sensitive to the combi-molecules of the present invention than EGFR⁺ cells, which was confirmed by the observed 5-fold stronger cytotoxic activity induced by BJ2000 in the EGFR transfectant (NIH3T3HER14), as compared to its parental line (NIH3T3). Since the single difference between the two cell types is their EGFR content, the results suggest that the binary mechanism of EGFR TK inhibition (TZ-I+I) and DNA damage (TZ), is as predicted, significantly more effective against the target-expressing cell type. Although the contribution of DNA lesions to the mechanisms underlying this selective cytotoxicity is not clear, it is noteworthy that BJ2000 induced more than 2-fold higher levels of DNA damage in the EGFR transfectant. This apparent EGFR-mediated enhancement of DNA damage may be rationalized in light of a partial hydrolysis of the combi-molecule while bound to the ATP site of the receptor. In the ATP site of the receptor, according to previously proposed models (52), the 6-position of the quinazoline ring is located at the entrance of the binding cleft. Fractions of BJ2000-derived methyldiazonium species may therefore also freely diffuse away from the receptor and perhaps reach the nucleus. Deuterium labeling experiments have presently well established that the 1,2,3-triazene-derived methyldiazonium, which is in equilibrium with diazomethane (Scheme 8), is the reactive species alkylating DNA (53). Studies are presently ongoing aiming to elucidate the observed EGFR-mediated enhancement of DNA damage, by correlating types and levels of these lesions with the EGFR affinity of a series of combi-molecules currently being synthesized. Despite being a non-DNA damaging agent, FD105 displayed EGFR-selective cytotoxicity. Although the mechanism underlying FD105-induced cytotoxicity is under investigation, results suggest that selectivity may be maintained even after complete hydrolytic conversion of the combi-molecule to FD105.

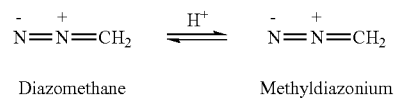

Scheme 8

Diazomethane ⇌ Methyldiazonium

The principle by which the multiple properties of BJ2000 should culminate in sustained growth inhibition, was demonstrated in comparison with its derived inhibitor FD105. In contrast to FD105, the antiproliferative activity of BJ2000 in A431 cells was partially retained as long as 5 days after a 2 h drug exposure. The complete loss of activity of FD105 and the marked inactivity of TEM, a known DNA damaging agent, in the A431 cells, suggests that the sustained antiproliferative activity of the combi-molecule (BJ2000) may result from an interactive effect between its DNA damaging component and its signal transduction inhibitory component. This assumption was further corroborated by experimental evidence illustrating the ability of the combi-molecule (BJ2000) to block MAPK phosphorylation at a concentration as low as 1 µM. Since MAPK is a critical signal transduction protein known to mediate the mitogenic effects of EGF-activated signaling (54) blockade of EGFR autophosphorylation by BJ2000 and by its derived inhibitor I may translate into inhibition of downstream signaling associated with expression of genes required to rescue the cells. A mechanism by which blockade of EGF-induced signal transduction by the TK inhibitory element down-regulates DNA repair enzymes (e.g. AGT, DNA glycosylases) or other critical proteins can thus be evoked in order to rationalize the EGFR-mediated sustained inhibition of proliferation induced BJ2000. Work aiming to verify this hypothesis, more specifically characterizing expressions of critical transcription factors (e.g. c-jun and c-fos) and specific DNA repair genes induced in response to cell exposure to BJ2000, is now in progress.

Although the present invention has been described herein above by way of preferred embodiments thereof, it can be modified, without departing from the spirit and nature of the subject invention as defined in the appended claims.

REFERENCES

1. Sinha et al., 1995; Sherwood et al., 1999; Kondapaka and Reddy, 1996; Alaoui-Jamali et al., 1997; Tsai et al., 1993.
2. Carroll et al., 1997; Deininger et al., 1997; Levitzki and Gazit, 1999.
3. Xie et al., 1999; Turner et al., 1996; Modjtahedi and Dean, 1998; Moyer et al., 1997.
4. Levitzki and Gazit, 1999; Rewcastle et al., 1997; Lanzi et al., 1997; Moyer et al., 1997; Rewcastle et al., 1995; Rewcastle et al., 1988.
5. Smaill et al., 1999.
6. Moyer, J. D., Barbacci, E. G., Iwata, K., Arnold, L., Boman, B., Cunningham, A., DiOrio, C., Doty, J., Morin, M. J., Moyer, M. J., Neveu, M., Pollak, V. A., Pustilnik, L. R., Reynolds, M. M., Sloan, D., Teleman, A., and Miller, P. Induction of apoptosis and cell cycle arrest by CP-358, 774, an inhibitor of epidermal growth factor receptor tyrosine kinase. Cancer Res. 57: 4838-4848, 1997.
7. Rewcastle, G. W., Denny, W. A., Bridges, A. J., Hairong, Z., Cody, D. R., McMichael, A., and Fry, D. W. Tyrosine kinase inhibitor. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J. Med. Chem. 38: 3482-3487, 1995.

8. Rewcastle, G. W., Murray, D. K., Elliott, W. L., Fry, D. W., Howard, C. T., Nelson, J. M., Roberts, B. J., Vincent, P. W., Showalter, H. D., Winters, R. T., and Denny, W. A. Tyrosine kinase inhibitors. 14. Structure-activity relationships for methylamino-substituted derivatives of 4-[(3-bromophenyl)amino]-6-(methylamino)-pyrido[3,4-d]pyridine (PD 158780), a potent and specific inhibitor of the tyrosine kinase activity of receptors for the EGF family of growth factors. J. Med. Chem. 41: 742-751, 1998.

9. Rewcastle, G. W., Murray, D. K., Elliott, W. L., Fry, D. W., Howard, C. T., Nelson, J. M., Roberts, B. J., Vincent, P. W., Showalter, H. D., Winters, R. T., and Denny, W. A. Tyrosine kinase inhibitors. 14. Structure-activity relationships for methylamino-substituted derivatives of 4-[(3-bromophenyl)amino]-6-(methylamino)-pyrido[3,4-d]pyridine (PD 158780), a potent and specific inhibitor of the tyrosine kinase activity of receptors for the EGF family of growth factors. J. Med. Chem. 41: 742-751, 1998.

10. Caliaro, M. J., Vitaux, P., Lafon, C., Lochon, I., Nehme, A., Valette, A., Canal, P., Bugat, R., and Jozan, S. Multifactorial mechanism for the potentiation of cisplatin (CDDP) cytotoxicity by all-trans retinoic acid (ATRA) in human ovarian carcinoma cell lines. Br. J. Cancer, 75: 333-340, 1997.

11. Modjtahedi, H. and Dean, C. The receptor for EGF and its ligands: expression, prognostic value and target for tumour therapy. Int. J. Oncol. 4: 277-296, 1998.

12. Fry, D. W.; (1999): Inhibition of the epidermal growth factor receptor family of tyrosine kinases as an approach to cancer chemotherapy: progression from reversible to irreversible inhibitors. Pharmacol Ther 82: 207-218.; Smaill et all., 2000.

13. Ciardiello, F.; Caputo, R.; Bianco, R.; Damiano, V.; Pomatico, G.; De Placido, S.; Bianco, A. R.; Tortora, G. (2000): Antitumor effect and potentiation of cytotoxic drugs activity in human cancer cells by ZD-1839 (Iressa), an epidermal growth factor receptor-sensitive tyrosine kinase inhibitor. Clin Cancer Res 6: 2053-2063.

14. Rewcastle et al., 1997; Rewcastle et al., 1995.

15. Rewcastle et al., 1997; Rewcastle et al., 1998; Rewcastle et al., 1995.

16. Rewcastle, G. W., Bridges, A., Fry, D. W., Rubin, R. R., and Denny, W. A. Tyrosine kinase inhibitors. 12. Synthesis and structure-activity relationships for 6-substituted 4-(phenylamino)pyrimidino[5,4d}pyrimidines designed as inhibitors of the epidermal growth factor receptor. J. Med. Chem. 40:1820-1826, 1997.

17. Rewcastle et al., 1995.

18. Walker, M. D. Nitrosoureas in central nervous system tumors. Cancer Chemother. Rep. 4: 21-26, 1973.

19. Walker M. D. and Hurwitz, B. S. BCNU (1,3-bis(2-chloroethyl)-1-nitrosourea; NSC-409962) in the treatment of malignant brain tumor—a preliminary report. Cancer Chemother. Rep. 54:273-281,1970.

20. Wilson, C. B., Boldrey, E. B., and Enot, K. J. 1,3-bis (2-chloroethyl)-1-nitrosourea (NSC-409962) in the treatment of brain tumors. Cancer Chemother. Rep. 54: 273-281, 1970.

21. Yarosh, D. B., Hurst-Calderone, S., Babich, M. A., and Day, R. S. Inactivation of O6-methylguanine-DNA methyltransferase and sensitization of human tumor cells to killing by chloroethylnitrosourea by O6-methylguanine as a free base. Cancer Res. 46: 1663-1668, 1986.

22. Gibson, N. W., Hartley, J. A., LaFrance, R. J., and Vaughan, K. Differential cytotoxicity and DNA-damage effects produced in human cells of the Mer+ and Mer– phenotypes by a series of 1-aryl-3-alkyltriazenes. Cancer Res. 46: 4999-5003, 1986.

23. Pegg et al., 1995; Tisdale, 1987; Bodell et al., 1985; Baer et al., 1993.

24. Ching et al., 1993b; Moyer et al., 1997b.

25. Tisdale, 1987; Mitchel and Dolan, 1993; Lee et al., 1991; Chen et al., 1993.

26. Matheson, S. L. M.; McNamee, J. P.; Jean-Claude, B. J. (2001): Design of a chimeric 3-methyl-1,2,3-triazene with mixed receptor tyrosine kinase and DNA damaging properties: a novel tumour targeting strategy. J Pharm Exp Ther 296: 832-840.

27. Baig, G. U.; Stevens, M. F. G. (1987): Antitumor imidazotetrazines. Part 12. Reactions of mitozolomide and its 3-alkyl congeners with oxygen, nitrogen, halogen, and carbon nucleophiles. J Chem Soc Perkin Trans 1, 1665-667.

Cameron, L. M.; LaFrance, R. J.; Hemens, C. M.; Vaughan, K.; Rajaraman, R.; Chubb, D. C.; Goddard, P. M.; (1985): Triazene metabolism. IV. Derivatives of hydroxymethyltriazenes: potential prodrugs for the active metabolites of the anti-tumour triazene, DTIC. Anti-Cancer Drug Des 1: 27-36.

28. Stevens, M. F. G.; Hickman, J. A.; Stone, R.; Gibson, N. W.; Baig, G. U.; Lunt, E.; Newton, C. G.; (1984): Antitumor imidazotetrazines. 1. Synthesis and chemistry of 8-carbamoyl-3-(2-chloroethyl)imidazo[5,1,-d]-1,2,3,5-tetrazin-4(3H)-one, a novel broad-spectrum antitumor agent. *J Med Chem* 27: 196-201.

Stevens, M. F. G.; Hickman, J. A.; Langdon, S. P.; Chubb, D.; Vickers, L.; Stone, R.; Baig, G.; Goddard, C.; Gibson, N. W.; Slack, J. A.; (1987): Antitumor activity and pharmacokinetics in mice of 8-carbamoyl-3-methyl-imidazo[5,1-d]-1,2,3,5-tetrazin-4(3H)-one (CCRG 81045; M&B 39831), a novel drug with potential as an alternative to dacarbazine. Cancer Res 47: 5846-5852.

29. Tsai, C. M.; Levitzki, A., Wu, L. H., Chang, K. T., Cheng, C., Gazit, A., and Perng, R. P. Enhancement of chemosensitivity by tyrphostin AG825 in High-p185 expressing non-small cell lung cancer cells. Cancer Res. 56: 1068-1074, 1996.

30. Moyer, J. D.; Barbacci, E. G.; Iwata, K. K.; Arnold, L.; Boman, B.; Cunningham, A.; DiOrio, C.; Doty, J.; Morin, M. J.; Moyer, M. P.; (1997): Induction of apoptosis and cell cycle arrest by CP-358,774, an inhibitor of epidermal growth factor receptor tyrosine kinase. Cancer Res 57: 4838-4848.;

Vincent, P. W.; Bridges, A. J.; Dykes, D. J.; Fry, D. W.; Leopold, W. R.; Patmore, S. J.; Roberts, B. J.; Rose, S.; Sherwood, V.; Zhou, H. (2000): Anticancer efficacy of the irreversible EGFr tyrosine kinase inhibitor PD 0169414 against human tumor xenografts. Cancer Chem Pharmacol 45: 231-238.

31. Singh et al., 1994.

32. McNamee, J. P.; Mclean, J. R.; Ferrarotto, C. L.; Bellier, P. V. (2000): Comet assay: rapid processing of multiple samples. Mutation Res 466: 63-69.

33. Skehan, P.; Storeng, R.; Scudiero, D.; Monks, A.; McMahon, J.; Vistica, D.; Warren, J. T.; Bokesch, H.; Kenney, S.; Boyd, M. R. (1990): New colorimetric cytotoxicity assay for anti-cancer drug screening. J Natl Cancer Inst 82: 1107-1112.

34. Cameron et al., 1985;

Manning, H. W.; Cameron, L. M.; LaFrance, R. J.; Vaughan, K.; Rajaman, R. (1985): Triazene metabolism. V. Chemical and biological properties of N,N-bis-[1-aryl-3-methyltriazen-3-yl)-methyl]-methylamines: potential prodrugs for the cytotoxic monomethyltriazenes. *Anti-cancer Drug Des* 1: 37-43.;

Rewcastle, G. W.; Denny, W. A.; Bridges, A. J.; Zhou, H.; Cody, D. R.; McMichael, A.; Fry, D. W. (1995): Tyrosine kinase inhibitors. 5. Synthesis and structure-activity relationships for 4-[(phenylmethyl)amino]- and 4-(phenylamino)quinazolines as potent adenosine 5′-triphosphate binding site inhibitors of the tyrosine kinase domain of the epidermal growth factor receptor. J Med Chem 38: 3482-3487.

35. Lanzi, C.; Pensa, T.; Cassinis, M.; Corti, C.; Gambetta, A. R.; Pratesi, G.; Menta, E.; Ardini, E.; Zunino, F. (1997): A cell and mechanism-based approach for the selection of EGF receptor inhibitors. Anti-cancer Drug Des. 12: 515-524.

36. Fornace et al., 1990.
37. Jean-Claude et al., 1999.
38. Chou et al., 1984.
39. Tari, A. M.; Lopez-Berestein, G.; (2000): Serum predominantly activates MAPK and akt kinases in EGFR- and ErbB2-overexpressing cells, respectively. Intl J Cancer 86: 295-297.
40. Smaill, J. B.; Rewcastle, G. W.; Loo, J. A.; Greis, K. D.; Chan, O. H.; Reyner, E. L.; Lipka, L.; Showalter, H. D.; Vincent, P. W.; Elliott, W. L.; (2000): Tyrosine kinase inhibitors 17. Irreversible inhibitors of the epidermal growth factor receptor: 4-(phenylamino)quinazoline and 4-(phenylamino)pyrido[3,2-d]pyrimidine-6-acrylaminde bearing additional solubilizing functions. J Med Chem 43: 1380-1397.
41. Fry, D. W.; Bridges, A. J.; Denny, W. A.; Doherty, A.; Greis, K. D.; Hicks, J. L.; Hook, K. E.; Keller, P. R.; Leopold, W. R.; Loo, J. A.; (1998): Specific irreversible inactivation of the epidermal growth factor receptor and erbB2, by a new class of tyrosine kinase inhibitor. Proc Natl Acad Science 95: 12022-12027.
42. Vistica, D. T.; Skehan, P.; Scudiero, D.; Monks, A.; Pittman, A.; Boyd, M. R. (1991): Tetrazolium-based assays for cellular viability: a critical examination of parameters affecting formazan production. Cancer Res 51: 2515-2520.
43. Mitchel, R. B.; Dolan, M. E. (1993): Effect of temozolomide and dacarbazine on O6-alkylguanine-DNA alkyltransferase activity and sensitivity of human tumor cells and xenografts to 1,3-bis(2-chloroethyl)-1-nitorsourea. Cancer Chemother. Pharmacol. 32:59-63.
44. Lanzi et al., 1997; Modjtahedi and Dean, 1998; Yaish et al., 1988; Modjtahedi and Dean, 1998.
45. Yaish et al., 1988.
46. Hill et al., 1989; Carter et al., 1976; Lee et al., 1992; Carter et al., 1994.
47. Kolar et al., 1980; Foedstad et al., 1985; Cameron et al., 1985; Manning et al., 1985.
48. Catapano et al., 1987.
49. Hartley et al., 1986; Pera et al., 1981.
50. Hammet, 1940; Andrejus, 1988; Jean-Claude and Williams, 1988.
51. Jeff et al., 2000.
52. Palmer, B. D.; Trumpp-Kallmeyer, S.; Fry, D. W.; Nelson, J. M.; Showalter, H.; Denny, W. A. (1997): Tyrosine kinase inhibitors. 11. Soluble analogues of pyrrolo- and pyrazoloquinazolines as epidermal growth factor receptor inhibitors: synthesis, biological evaluation and modeling of the mode of binding. J Med Chem 40: 1519-1529.
53. Denny, B. J.; Wheelhouse, R. T.; Stevens, M. F.; Tsang, L. L.; Slack, J. A. (1994): NMR and molecular modeling investigation of the mechanism of activation of the antitumor drug temozolomide and its interaction with DNA. Biochemistry 33: 9045-9051.
54. Davis, R. J. (1993): The mitogen-activated protein kinase signal transduction pathway. J Biol Chem 268: 14553-14556.

The invention claimed is:

1. A combi-molecule of general Formula I:

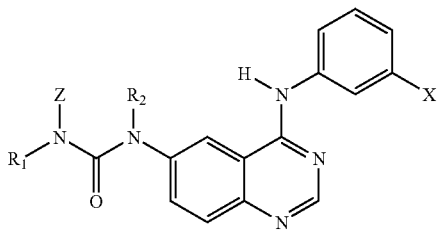

Formula I or a pharmaceutically acceptable salt thereof, wherein:
  a) $R_1$ is selected from the group consisting of: methyl, ethyl, and chloroethyl ($ClCH_2CH_2$—);
  b) $R_2$ is selected from the group consisting of: hydrogen, methyl, ethyl, chloroethyl ($ClCH_2CH_2$—) and hydroxyethyl;
  c) Z is selected from the group consisting of: nitroso and hydrogen; and
  d) X is selected from the group consisting of: methyl, chlorine, bromine and iodine.

2. The combi-molecule of claim 1, wherein $R_1$ is a chloroethyl group $R_2$ is a hydrogen, Z is a nitroso group and X is a methyl group.

3. The combi-molecule of claim 1, wherein $R_1$ is a methyl group, $R_2$ is a hydrogen, Z is a nitroso group and X is a methyl group.

4. The combi-molecule of claim 1, wherein $R_1$ is a chloroethyl group, $R_2$ is a methyl group, Z is a nitroso group and X is a methyl group.

5. The combi-molecule of claim 1, wherein $R_1$ is a methyl group, $R_2$ is a methyl group, Z is a nitroso group and X is a methyl group.

6. The combi-molecule of claim 1, wherein one part of the combi-molecule functions as a ligand to a molecule involved in cell signaling pathways and a second part of the combi-molecule functions as a DNA damaging agent.

7. The combi-molecule as defined in claim 6, wherein said molecule involved in cell signaling pathways is a receptor tyrosine kinase.

8. The combi-molecule as defined in claim 7, wherein said receptor tyrosine kinase is Epidermal Growth Factor Receptor (EGFR).

9. The combi-molecule as defined in claim 6, wherein said ligand is an inhibitor of Epidermal Growth Factor Receptor (EGFR).

10. The combi-molecule as defined in claim 6, wherein said DNA damaging agent is an alkyl diazonium species.

11. The combi-molecule as defined in claim 6, wherein said ligand is an inhibitor of EGFR and wherein said DNA damaging agent is an alkyl diazonium species.

12. A pharmaceutical composition comprising a combi-molecule as defined in claim 1 and at least one pharmaceutically acceptable carrier.

13. A method of treating EGFR expressing tumors comprising administering a therapeutically effective amount of a combi-molecule as defined in claim 1.

14. A combi-molecule of general Formula II:

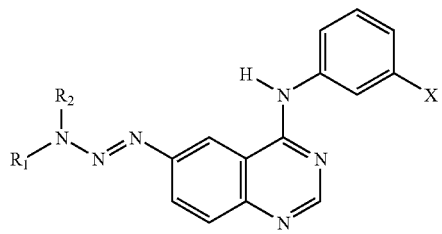

Formula II wherein:

a) $R_1$ is selected from the group consisting of: methyl, $CH_2OY$, acyl, $MeOCH_2CH_2$—,

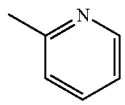 and 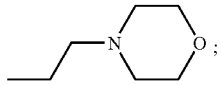 ;

wherein Y is selected from the group consisting of H, acyl and thiophenol;

b) $R_2$ is selected from the group consisting of: hydrogen and methyl; and c) X is selected from the group consisting of: chlorine, bromine, iodine and methyl.

15. The combi-molecule of claim 14, wherein $R_1$ is methyl, $R_2$ is a hydrogen and X is a methyl group.

16. The combi-molecule of claim 14, wherein $R_1$ is methyl, $R_2$ is a hydrogen and X is a chlorine.

17. The combi-molecule of claim 14, wherein $R_1$ is methyl, $R_2$ is a hydrogen and X is a bromine.

18. The combi-molecule of claim 14, wherein $R_1$ is $MeOCH_2CH_2$—, $R_2$ is a hydrogen and X is a bromine.

19. The combi-molecule of claim 14, wherein $R_1$ is $MeOCH_2CH_2$—, $R_2$ is a hydrogen and X is a methyl group.

20. The combi-molecule of claim 14, wherein $R_1$ is

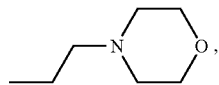

$R_2$ is a hydrogen and X is a bromine.

21. The combi-molecule of claim 14, wherein $R_1$ is

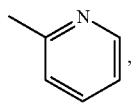

$R_2$ is a hydrogen and X is a bromine.

22. The combi-molecule of claim 14, wherein one part of the combi-molecule functions as a ligand to a molecule involved in cell signaling pathways and a second part of the combi-molecule functions as a DNA damaging agent.

23. The combi-molecule as defined in claim 22, wherein said molecule involved in cell signaling pathways is a receptor tyrosine kinase.

24. The combi-molecule as defined in claim 23, wherein said receptor tyrosine kinase is Epidermal Growth Factor Receptor (EGFR).

25. The combi-molecule as defined in claim 22, wherein said ligand is an inhibitor of Epidermal Growth Factor Receptor (EGFR).

26. The combi-molecule as defined in claim 22, wherein said ligand is a compound binding competitively to an ATP site.

27. The combi-molecule as defined in claim 22, wherein said DNA damaging agent is an alkyl diazonium species.

28. The combi-molecule as defined in claim 22, wherein said ligand is an inhibitor of EGFR and wherein said DNA damaging agent is an alkyl diazonium species.

29. A pharmaceutical composition comprising a combi-molecule as defined in claim 14 and at least one pharmaceutically acceptable carrier.

30. A method of treating EGFR expressing tumors comprising administering a therapeutically effective amount of a combi-molecule as defined in claim 14.

* * * * *

UNITED STATES PATENT AND TRADEMARK OFFICE
CERTIFICATE OF CORRECTION

| | | |
|---|---|---|
| PATENT NO. | : 7,572,798 B2 | Page 1 of 1 |
| APPLICATION NO. | : 10/469368 | |
| DATED | : August 11, 2009 | |
| INVENTOR(S) | : Jean-Claude et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this

Seventh Day of September, 2010

David J. Kappos
*Director of the United States Patent and Trademark Office*